(12) United States Patent
Mirizzi et al.

(10) Patent No.: US 10,143,476 B2
(45) Date of Patent: *Dec. 4, 2018

(54) METHOD AND APPARATUS FOR STORAGE AND/OR INTRODUCTION OF IMPLANT FOR HOLLOW ANATOMICAL STRUCTURE

(75) Inventors: Michael S. Mirizzi, San Jose, CA (US); Halil I. Karabey, San Jose, CA (US); Miranda M. Ray, San Jose, CA (US); William N. Boenig, San Mateo, CA (US)

(73) Assignee: Covidien LP, Mansfield, MA (US)

( * ) Notice: Subject to any disclaimer, the term of this patent is extended or adjusted under 35 U.S.C. 154(b) by 1586 days.

This patent is subject to a terminal disclaimer.

(21) Appl. No.: 12/642,717

(22) Filed: Dec. 18, 2009

(65) Prior Publication Data

US 2010/0160946 A1 Jun. 24, 2010

Related U.S. Application Data

(60) Provisional application No. 61/139,509, filed on Dec. 19, 2008, provisional application No. 61/230,252, (Continued)

(51) Int. Cl.
*A61M 29/00* (2006.01)
*A61B 17/12* (2006.01)
(Continued)

(52) U.S. Cl.
CPC .. *A61B 17/12022* (2013.01); *A61B 17/12109* (2013.01); *A61B 17/12181* (2013.01);
(Continued)

(58) Field of Classification Search
CPC ........ A61B 17/12022; A61B 17/12109; A61B 17/12181
(Continued)

(56) References Cited

U.S. PATENT DOCUMENTS 3,320,956 A 5/1967 Steiger
3,463,158 A 8/1969 Schmitt et al.
(Continued)

FOREIGN PATENT DOCUMENTS

EP 0 778 005 A1 6/1997
EP 0 882 428 A3 6/2000
(Continued)

OTHER PUBLICATIONS

Lord, P., Handbook of Yarn Production, 2003, Woodhead Publishing Ltd. and CRC Press LLC, pp. 12-17, 48-55, 88-115, 368-371.
(Continued)

*Primary Examiner* — Richard Louis
(74) *Attorney, Agent, or Firm* — Shumaker & Sieffert, P.A.

(57) ABSTRACT

An apparatus for introducing an implant into a hollow anatomical structure. The apparatus comprises a storage unit having an exit opening and defining a chamber in communication with the exit opening; an elongate, self-expanding vascular implant having an expanded condition and stored within the chamber in the expanded condition, proximal of the exit opening; and a pushrod having a distal end aligned with and proximal of the exit opening. The pushrod is pre-assembled to a distal end of the implant. Associated methods, and other apparatus and methods, are also disclosed.

28 Claims, 50 Drawing Sheets

Related U.S. Application Data filed on Jul. 31, 2009, provisional application No. 61/249,515, filed on Oct. 7, 2009.

(51) Int. Cl.
  *A61B 17/00* (2006.01)
  *A61B 50/30* (2016.01)
(52) U.S. Cl.
  CPC ..... *A61B 50/30* (2016.02); *A61B 2017/00004* (2013.01); *A61B 2017/1205* (2013.01); *A61B 2017/12054* (2013.01)
(58) Field of Classification Search
  USPC ........ 606/108, 200, 213; 604/41, 43, 11–18, 604/59–60, 164.04, 904; 623/1.54, 13.2
  See application file for complete search history.

(56) References Cited

U.S. PATENT DOCUMENTS

| | | | |
|---|---|---|---|
| 4,038,194 A | | 7/1977 | Luceyk et al. |
| 4,148,317 A | | 4/1979 | Loyer |
| 4,651,736 A | * | 3/1987 | Sanders ................... 128/898 |
| 4,832,055 A | | 5/1989 | Palestrant |
| 4,860,757 A | | 8/1989 | Lynch et al. |
| 4,994,069 A | | 2/1991 | Ritchart et al. |
| 5,226,911 A | | 7/1993 | Chee et al. |
| 5,258,042 A | | 11/1993 | Mehta |
| 5,275,604 A | | 1/1994 | Rheinish et al. |
| 5,304,187 A | | 4/1994 | Green et al. |
| 5,324,304 A | | 6/1994 | Rasmussen |
| 5,354,295 A | | 10/1994 | Guglielmi et al. |
| 5,370,660 A | | 12/1994 | Weinstein et al. |
| 5,382,259 A | | 1/1995 | Phelps et al. |
| 5,626,603 A | | 5/1997 | Venturelli et al. |
| 5,649,953 A | | 7/1997 | Lefebvre |
| 5,658,308 A | | 8/1997 | Snyder |
| 5,676,671 A | * | 10/1997 | Inoue ..................... A61F 2/95 604/247 |
| 5,690,671 A | | 11/1997 | McGurk et al. |
| 5,700,258 A | | 12/1997 | Mirigian et al. |
| 5,897,497 A | * | 4/1999 | Fernandez ................... 600/435 |
| 5,935,145 A | | 8/1999 | Villar et al. |
| 6,083,231 A | | 7/2000 | Van Noy et al. |
| 6,090,125 A | | 7/2000 | Horton |
| 6,136,015 A | | 10/2000 | Kurz et al. |
| 6,187,027 B1 | | 2/2001 | Mariant et al. |
| 6,338,739 B1 | | 1/2002 | Datta et al. |
| 6,368,338 B1 | | 4/2002 | Konya et al. |
| 6,432,116 B1 | | 8/2002 | Callister et al. |
| 6,544,236 B1 | * | 4/2003 | Cragg et al. ................... 604/254 |
| 6,602,261 B2 | | 8/2003 | Greene, Jr. et al. |
| 6,638,293 B1 | | 10/2003 | Makower et al. |
| 6,656,204 B2 | | 12/2003 | Ambrisco et al. |
| 6,660,020 B2 | | 12/2003 | Wallace et al. |
| 6,709,667 B1 | | 3/2004 | Lowe et al. |
| 6,818,018 B1 | | 11/2004 | Sawhney |
| 6,984,244 B2 | | 1/2006 | Perez et al. |
| 7,192,436 B2 | | 3/2007 | Sing et al. |
| 2001/0044629 A1 | | 11/2001 | Stinson |
| 2002/0143349 A1 | | 10/2002 | Gifford, III et al. |
| 2003/0004568 A1 | | 1/2003 | Ken et al. |
| 2003/0015203 A1 | | 1/2003 | Makower et al. |
| 2003/0149463 A1 | | 8/2003 | Hyodoh et al. |
| 2004/0015187 A1 | | 1/2004 | Lendlein et al. |
| 2004/0220611 A1 | | 11/2004 | Ogle |
| 2004/0254589 A1 | | 12/2004 | Darnis et al. |
| 2005/0038495 A1 | * | 2/2005 | Greenan ................... A61F 2/95 623/1.11 |
| 2005/0070952 A1 | | 3/2005 | Devellian |
| 2005/0085847 A1 | | 4/2005 | Galdonik et al. |
| 2005/0107867 A1 | | 5/2005 | Taheri |
| 2005/0165480 A1 | * | 7/2005 | Jordan et al. ..................... 623/9 |
| 2006/0009798 A1 | | 1/2006 | Callister et al. |
| 2006/0105026 A1 | | 5/2006 | Fortune et al. |
| 2006/0116713 A1 | * | 6/2006 | Sepetka ........... A61B 17/12022 606/200 |
| 2006/0224083 A1 | | 10/2006 | Clifford et al. |
| 2006/0229669 A1 | * | 10/2006 | Mirizzi ............ A61B 17/12022 606/213 |
| 2007/0056591 A1 | | 3/2007 | McSwain |
| 2007/0166345 A1 | | 7/2007 | Pavcnik et al. |
| 2007/0244439 A1 | | 10/2007 | Mujwid et al. |
| 2008/0221703 A1 | * | 9/2008 | Que et al. ................... 623/23.65 |
| 2009/0105711 A1 | | 4/2009 | Mitchell |

FOREIGN PATENT DOCUMENTS

| | | |
|---|---|---|
| EP | 1 169 969 A1 | 1/2002 |
| JP | 2002282275 | 10/2002 |
| WO | WO 03/043506 | 5/2003 |

OTHER PUBLICATIONS

International Search Report and Written Opinion for International Application No. PCT/US2006/002470, Notification dated Aug. 28, 2006.
U.S. Appl. No. 12/642,696, filed Dec. 18, 2009, Karabey et al.
U.S. Appl. No. 12/642,699, filed Dec. 18, 2009, Michael S. Mirizzi.
U.S. Appl. No. 11/339,978, filed Jan. 25, 2006, Karabey et al., 2006/0212127, Sep. 21, 2006.
U.S. Appl. No. 11/340,183, filed Jan. 25, 2006, Mirizzi et al., 2006/0229669, Oct. 12, 2006.
U.S. Appl. No. 11/339,975, filed Jan. 25, 2006, Prestezog et al., 2006/0229668, Oct. 12, 2006.
U.S. Appl. No. 11/339,927, filed Jan. 25, 2006, Karabey et al., 2006/0212055, Sep. 21, 2006.
U.S. Appl. No. 12/340,265, filed Dec. 19, 2008, Karabey et al., 2009/0159088, Jun. 25, 2009.
U.S. Appl. No. 11/407,858, filed Oct. 25, 2007, Karabey et al., 2007/0248640, Oct. 25, 2007.
International Search Report and Written Opinion for International Application No. PCT/US2009/068872, Notification dated Apr. 29, 2010.
Decision on Appeal from U.S. Appl. No. 12/642,699, dated May 19, 2016, 8 pages.
Notice of Allowance from U.S. Appl. No. 12/642,699, dated Jul. 29, 2016, 10 pages.

\* cited by examiner

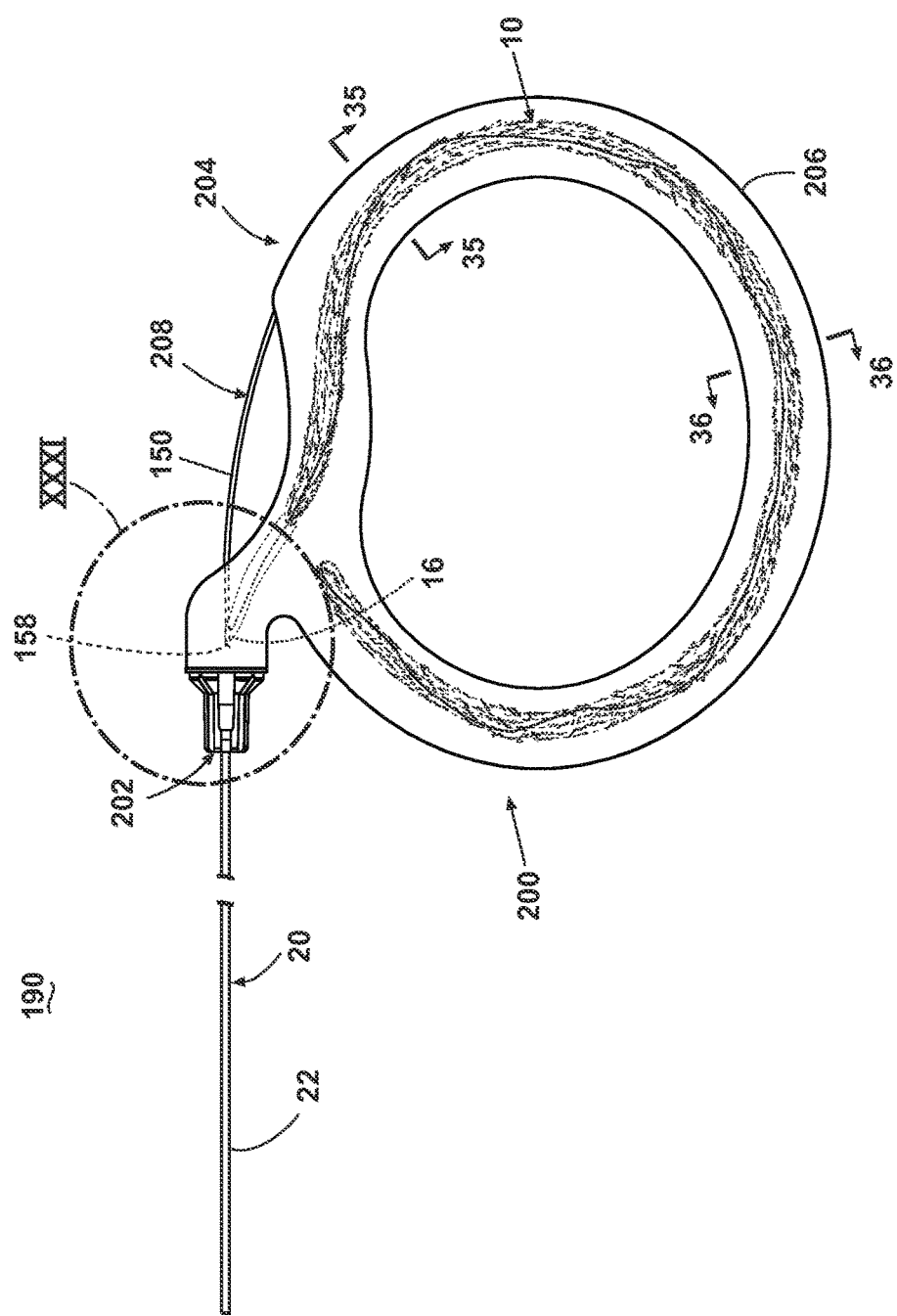

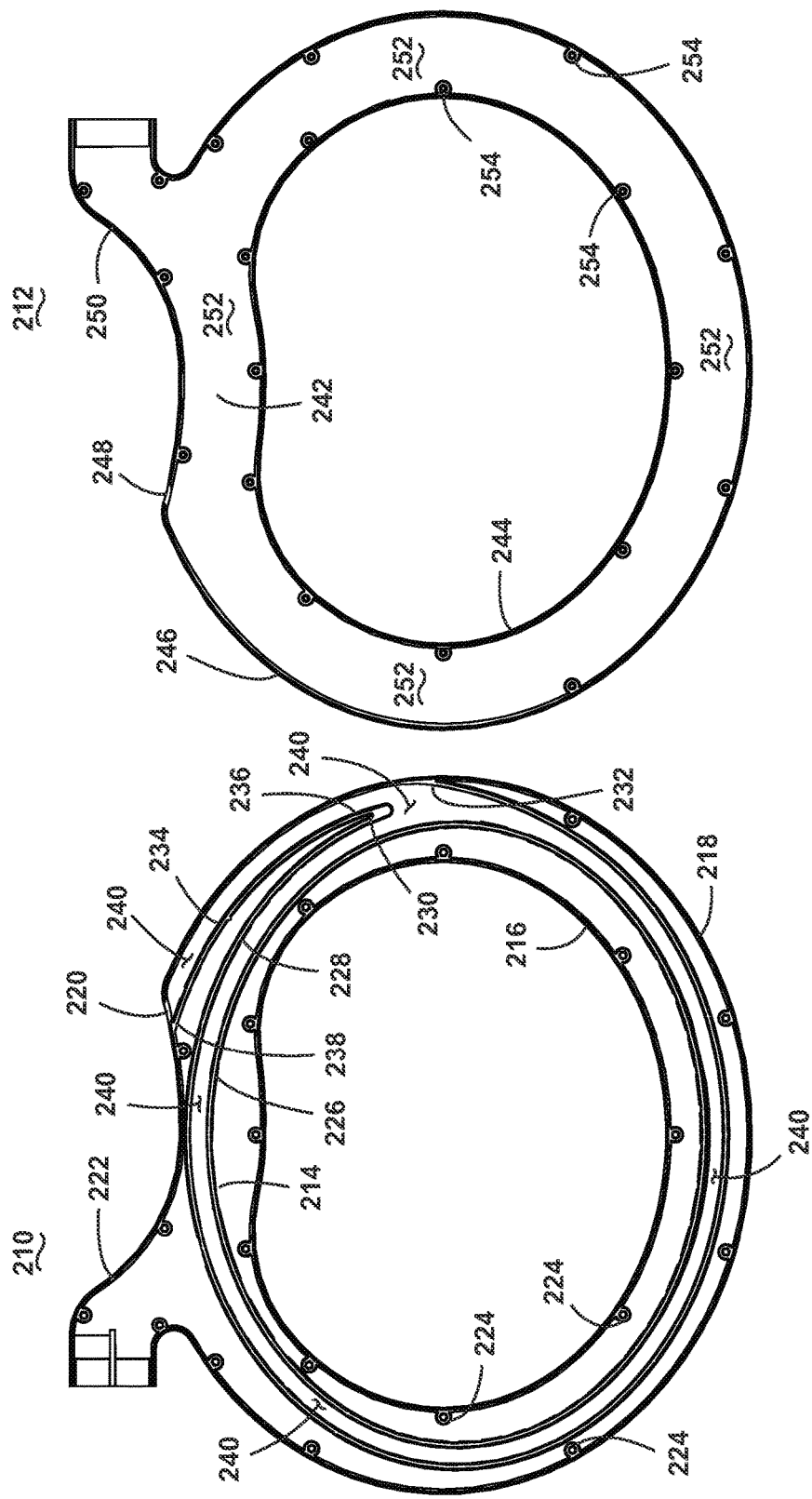

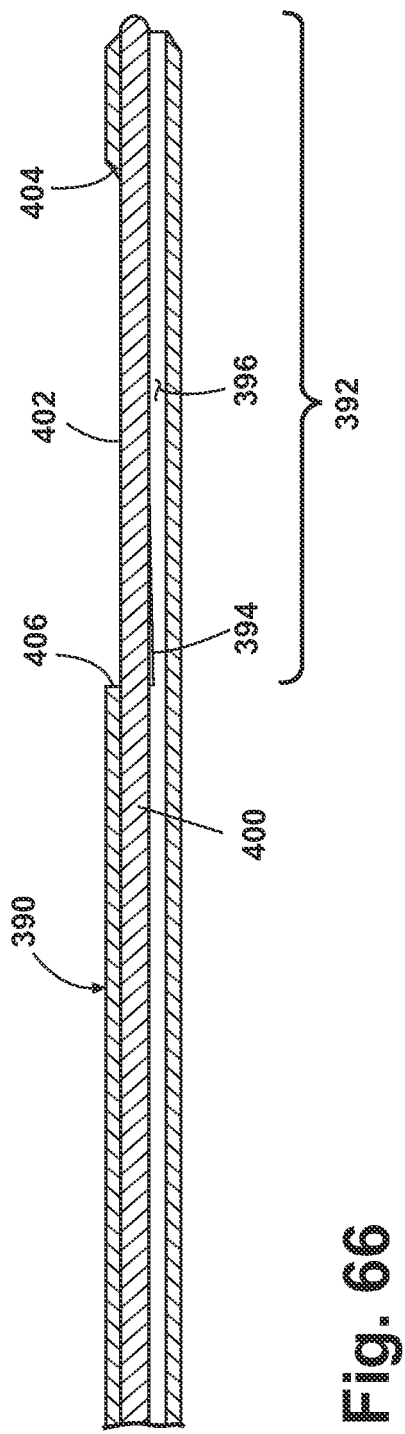
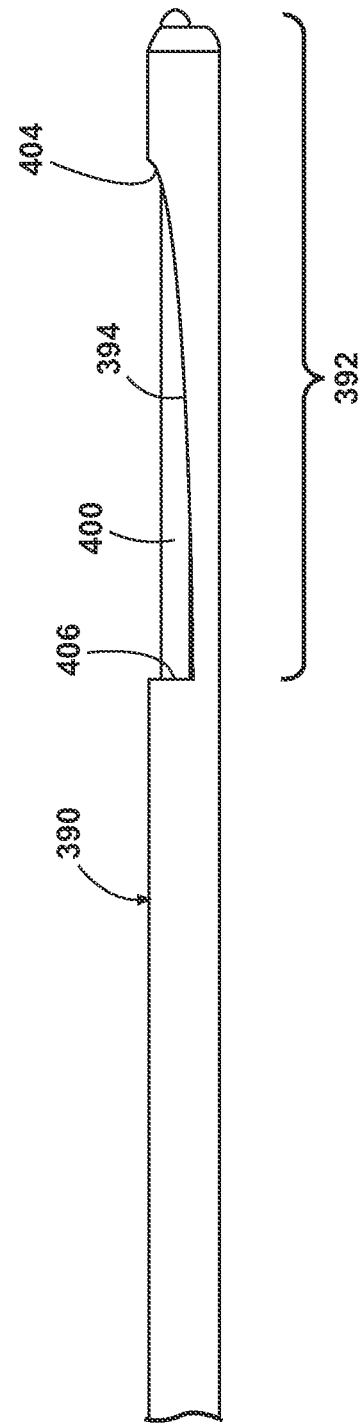

METHOD AND APPARATUS FOR STORAGE AND/OR INTRODUCTION OF IMPLANT FOR HOLLOW ANATOMICAL STRUCTURE

RELATED APPLICATIONS

This application claims priority under 35 U.S.C. § 119(e) to the following U.S. provisional patent application Ser. No. 61/139,509, filed Dec. 19, 2008, titled METHOD AND APPARATUS FOR STORAGE AND/OR INTRODUCTION OF OCCLUDING IMPLANT FOR HOLLOW ANATOMICAL STRUCTURE; Ser. No. 61/230,252, filed Jul. 31, 2009, titled METHOD AND APPARATUS FOR STORAGE AND/OR INTRODUCTION OF OCCLUDING IMPLANT FOR HOLLOW ANATOMICAL STRUCTURE; and Ser. No. 61/249,515, filed Oct. 7, 2009, titled METHOD AND APPARATUS FOR STORAGE AND/OR INTRODUCTION OF OCCLUDING IMPLANT FOR HOLLOW ANATOMICAL STRUCTURE. The entire disclosure of each of the above-mentioned provisional applications (less any material incorporated by reference therein, and less their Appendices) is incorporated by reference herein.

BACKGROUND

Field

Treatment of hollow anatomical structures such as blood vessels, hollow organs, fallopian tubes, gastric structures, etc.

Related Art

Referring to FIG. 1, the human venous system of the leg A comprises the superficial venous system, shown in white, and the deep venous system, shown in black, with perforating veins connecting the two systems. The superficial system includes the long or great saphenous vein B and the small saphenous vein C. The deep venous system includes the anterior and posterior tibial veins D, E, which unite to form the popliteal vein F, which in turn becomes the femoral vein G when joined by the short saphenous vein C. The femoral vein G and the great saphenous vein B join at the saphenofemoral junction H.

The venous system contains numerous one-way valves for directing antegrade blood flow back to the heart. When an incompetent valve is in the flow path, the valve is unable to close, and retrograde flow of the blood away from the heart cannot be stopped. When a venous valve fails, increased strain and pressure occur within the lower venous sections and overlying tissues, sometimes leading to additional, distal valvular failure. Two venous conditions or symptoms that often result from valve failure are varicose veins and more symptomatic chronic venous insufficiency. Current treatments of venous insufficiency include surgical procedures such as vein stripping, vein-segment transplant, and ligation by ablation.

Vein stripping typically consists of tying off, or ligating, and removing the saphenous vein. Vein segment transplant has been employed in certain organ transplant procedures; however, it is not generally employed in the superficial venous system in humans. Ligation by ablation involves the cauterization or coagulation of vascular lumina using thermal energy applied through a delivery device. Energy introduced into the vein lumen causes the vein wall to shrink in cross-sectional diameter or completely collapse, thereby reducing or completely blocking blood flow through the vein.

An alternative treatment involves placement of an occluding implant in the hollow anatomical structure, such as the great saphenous vein. As an example, the implant can be a fibrous body, optionally textured to impart bulk. The implant causes a partial occlusion of the hollow anatomical structure, followed by a complete or substantially complete occlusion, such as by formation of an organic fibrotic occlusion resulting from the body's natural foreign body healing response.

SUMMARY

A non-exhaustive summary of embodiments disclosed herein follows.

The present disclosure includes, in a first embodiment, a system for introducing an occluding implant into a hollow anatomical structure, such as a vein, comprising an introducer sheath and an apparatus proximally coupled to the introducer sheath. The introducer sheath comprises a shaft sized for insertion into the hollow anatomical structure and forming a lumen. A proximal opening of the introducer sheath provides access to the shaft lumen. The apparatus comprises an occluding implant, an implant storage unit forming a chamber (e.g. an elongate chamber) that houses the implant, and an introducer coupled to the implant. An exit opening of the apparatus is in communication with the implant storage unit chamber. The introducer is movable relative to the implant storage unit and the introducer sheath and has a travel direction through the implant storage unit exit opening and the introducer sheath proximal opening to thereby move the implant from the implant storage unit chamber to the introducer sheath shaft lumen.

Further optional features and variations of this first embodiment are presented in the following paragraphs. The present disclosure contemplates and includes employing these optional features and variations in the first embodiment (or in any other embodiment summarized or described herein), either alone or in any feasible combination of two or more such optional features and variations.

The introducer can comprise a pushrod stored generally in a loop configuration, and the implant can be stored (and/or the implant storage unit chamber can be located) alongside the pushrod so that it extends and curves along and next to the loop formed by the pushrod (or the pushrod housing). The implant (and/or the implant storage unit chamber) can generally conform to the shape of the loop as it extends and curves along the loop. The pushrod and the implant can be contained (and/or the implant storage unit chamber can be formed) in a common casing generally shaped like a ring. The ring can generally conform to the pushrod loop and form a radially inward deflection from the ring configuration to expose a portion of the pushrod for manual gripping. The pushrod and the implant can diverge at distal portions thereof so that the pushrod exits the implant storage unit to expose a length of the pushrod for manual gripping. The pushrod and implant can be connected to each other near the distal tip of the pushrod.

The exit opening and the proximal opening can be aligned with each other. For example, the exit opening and the proximal opening can be axially aligned. The exit opening and the proximal opening can be directly adjacent each other when the apparatus is coupled to the introducer sheath.

The apparatus can further comprise a coupler coupling the apparatus to the introducer sheath. The coupler can include a proximal coupler disposed on the apparatus, such as on the implant storage unit, and a distal coupler disposed on the introducer sheath, whereby coupling of the proximal and distal couplers effects the coupling of the apparatus to the introducer sheath. The introducer sheath can further comprise a hub located at a proximal end of the sheath and forming the proximal opening, and the distal coupler can be disposed on the hub. The apparatus exit opening can be formed by the coupler, such as by the proximal coupler. The coupler can be configured to automatically align the exit opening and the proximal opening upon coupling the apparatus to the introducer sheath.

The implant storage unit can define a storage axis, and the introducer and the implant can have a common travel direction through the exit opening and into the introducer sheath, wherein the storage axis is offset relative to the common travel direction. For example, the storage axis can be angularly offset relative to the common travel direction. The storage axis can be offset at an obtuse angle relative to the common travel direction.

The implant can comprise a fibrous body. The fibrous body can be made of a bioresorbable material. In one example, the fibrous body can have a natural expanded condition and can be compressed upon application of a compressive force. For example, when the implant is in the chamber of the implant storage unit, the implant body can assume a storage condition in which the implant body is in the naturally expanded condition, and when the implant is in the lumen of the introducer sheath shaft, the shaft can compress the implant body to an introduction condition. Further, when the implant is implanted in the hollow anatomical structure upon removal of the introducer sheath from the hollow anatomical structure, the implant body can expand from the introduction condition to an implantation condition, wherein the thickness of the implant body is greater than when in the introduction condition and less than when in the storage condition. To accommodate the implant body in the storage condition, the implant storage unit can have a gauge (or cross-sectional size, or lumen inside diameter) greater than or equal to the size or thickness of the implant body when in the naturally expanded condition. Further, the gauge (or cross-sectional size, or lumen inside diameter) of the implant storage unit can be greater than a gauge (or lumen inside diameter) of the introducer sheath shaft. The apparatus can include a guide to facilitate compression of the implant body during movement of the introducer and, thereby, the implant from the implant storage unit to the introducer sheath. The guide can be, for example, a distally tapering frustoconical wall, and the frustoconical wall can terminate at the exit opening. The guide can be formed in a coupler coupling the apparatus to the introducer sheath.

The implant can include a tether. In one example, the implant comprises an elastic fibrous body, and the tether can be inelastic. The fibrous body can comprise multiple bulked fibers, and the tether can comprise an inelastic yarn. Further, the tether can be made of a bioresorbable material, such as the same bioresorbable material as the implant body. The tether can be coupled to the fibrous body at a distal end of the fibrous body. As an example, when the implant is fully inserted into the hollow anatomical structure, a distal end of the tether is located at the distal end of the fibrous body in the hollow anatomical structure, and a proximal end of the tether is attached externally of the hollow anatomical structure to prevent distal migration of the fibrous body in the hollow anatomical structure. The proximal end of the tether can be secured to an external surface of the body, such as by adhesive tape. The proximal end of the tether can be incorporated into sutures that close an access site for the hollow anatomical structure.

The implant storage unit can further comprise an end cap closing an open proximal end of the implant storage unit. The end cap can be removable. In one example, the implant can be anchored to the proximal end of the implant storage unit by the end cap, such as by the implant body and/or the tether being disposed between the end cap and the implant storage unit.

The introducer can comprise a pushrod. The pushrod can be coupled to a distal end of the implant; for example, a distal end of the pushrod can be coupled to a distal end of the implant. The pushrod can form a lumen that houses a wire. The distal end of the pushrod can be closed, such as by a plug, and a distal end of the wire can be attached to the closed distal end. The pushrod can further include first and second openings through which the wire passes to form an implant retaining portion externally of the pushrod lumen and between the openings. The implant can be held between the implant retaining portion and the pushrod. The first opening can be located proximally of the second opening. For example, the first and second openings can be linearly arranged along the pushrod. A proximal end of the wire can project from the pushrod to enable application of a proximal force to the wire. As an example, the proximal end of the wire can extend out of an open proximal end of the pushrod. Application of the proximal force to the wire can effect detachment of the distal end of the wire from the pushrod. Continued application of the proximal force effects liberation of the implant from the introducer as the implant retaining portion of the wire retracts into the pushrod lumen via the first, proximal opening.

The pushrod can be stored externally of the implant storage unit and enter the implant storage unit near a distal end of the implant storage unit. For example, the pushrod can extend through an aperture formed near the distal end of the implant storage unit. The aperture can be aligned with the apparatus exit opening such that the distal end of the pushrod is aligned with the exit opening for movement of the pushrod in the travel direction through the exit opening. The aperture and the exit opening can be axially aligned. The apparatus can further include a container that houses the pushrod externally of the implant storage unit. For example, the container can comprise a reel, or a coiled tube mounted to the implant storage unit. An exposed portion of the pushrod between the container/tube/reel and the aperture through the pushrod can extend into the implant storage unit provides a gripping area for a user to grasp and move the pushrod.

The apparatus comprising the implant, the implant storage unit, the coupler, and the introducer can be provided as an assembled kit wherein the implant is assembled in the implant storage unit and coupled to the introducer. When the coupler comprises the proximal and distal couplers, the proximal and distal couplers can be provided in a decoupled condition or a coupled condition. When the proximal and distal couplers are provided in the coupled condition, the user decouples the distal coupler from the proximal coupler prior to use of the apparatus. As one alternative, the kit can further include the introducer sheath. When the kit includes the introducer sheath, the introducer sheath and the apparatus can be provided as coupled or decoupled.

In a second embodiment, an apparatus for introducing an occluding implant into a hollow anatomical structure, such as a vein, comprises an occluding implant, an implant storage unit forming a chamber (e.g. an elongate chamber) that houses the implant, and an introducer coupled to the implant. An exit opening of the apparatus is in communication with the implant storage unit chamber. The introducer is movable relative to the implant storage unit and has a travel direction through the implant storage unit exit opening to thereby move the implant from the implant storage unit chamber to externally of the apparatus.

The present disclosure contemplates and includes optionally employing in the second embodiment, the optional features and variations of the first embodiment identified above, either alone or in any feasible combination of two or more such optional features and variations.

The introducer can comprise a pushrod stored generally in a loop configuration, and the implant can be stored (and/or the implant storage unit chamber can be located) alongside the pushrod so that it extends and curves along and next to the loop formed by the pushrod (or the pushrod housing). The implant (and/or the implant storage unit chamber) can generally conform to the shape of the loop as it extends and curves along the loop. The pushrod and the implant can be contained (and/or the implant storage unit chamber can be formed) in a common casing generally shaped like a ring. The ring can generally conform to the pushrod loop and form a radially inward deflection from the ring configuration to expose a portion of the pushrod for manual gripping. The pushrod and the implant can diverge at distal portions thereof so that the pushrod exits the implant storage unit to expose a length of the pushrod for manual gripping. The pushrod and implant can be connected to each other near the distal tip of the pushrod.

The present disclosure also includes methods of storing and/or introducing an occluding implant into a hollow anatomical structure, such as a vein. In a third embodiment, a method employs a system comprising an introducer sheath and an apparatus. The introducer sheath comprises a shaft sized for insertion into the hollow anatomical structure and forming a lumen. A proximal opening of the introducer sheath provides access to the shaft lumen. The apparatus comprises an occluding implant, an implant storage unit forming an elongate chamber that houses the implant, and an introducer coupled to the implant. An exit opening of the apparatus is in communication with the implant storage unit chamber. The method can optionally comprise inserting the introducer sheath shaft into the hollow anatomical structure. The method can further comprise coupling the apparatus to a proximal end of the introducer sheath, thereby arranging the implant storage unit exit opening and the introducer sheath proximal opening to establish a travel direction of the introducer therethrough, and distally advancing the introducer along the travel direction to move the implant from the implant storage unit, through the implant storage unit exit opening, through the introducer sheath proximal opening, and into the introducer sheath shaft lumen.

Further optional features and variations of this third embodiment are presented in the following paragraphs. The present disclosure contemplates and includes employing these optional features and variations in the third embodiment (or in any other embodiment summarized or described herein), either alone or in any feasible combination of two or more such optional features and variations.

The method can further include continuing the distal advancement of the introducer and the implant into the introducer sheath shaft lumen. For example, the advancement of the introducer and the implant can continue until the introducer reaches a distal end of the introducer sheath shaft. In the case where the hollow anatomical structure is the greater saphenous vein, the advancement of the introducer and the implant continues until a distal end of the implant is located below the sapheno-femoral junction. As an example, the distal end of the implant can be located just below, for example about 2.5 cm below, the sapheno-femoral junction.

The method can further include compressing the implant during the distal advancement of the introducer along the travel direction. For example, the implant can be compressed in the apparatus while moving the implant through the exit opening. The apparatus can include a guide in the form of a distally tapering frustoconical wall that terminates at the exit opening, and the compression of the implant further includes moving the implant through the guide to gradually compress the implant from a storage condition when in the implant storage unit to an introduction condition when the implant moves through the exit opening. When the implant is in the storage condition, the implant can assume a naturally expanded condition.

The method can further include removing the introducer sheath from the hollow anatomical structure. Further, the method can continue with removing the introducer from the hollow anatomical structure. Prior to removing the introducer, the method can include decoupling the implant from the introducer, thereby leaving the implant in the hollow anatomical structure following removal of the introducer sheath. The introducer can comprise a pushrod having an implant retaining wire attached to the pushrod, wherein the wire facilitates coupling the implant to the pushrod, and the decoupling of the implant from the introducer comprises detaching the wire from the pushrod. For example, the detaching of the wire from the pushrod can comprise applying a proximal force to the wire.

The method can include expanding the implant during the removing of the introducer sheath from the hollow anatomical structure. For example, the expanding of the implant can comprise expanding the implant from an introducing condition when the implant is in the introducer sheath shaft to an implantation condition when the implant is in the hollow anatomical structure. Thus, following the example provided above, the method can comprise compressing the implant from a storage condition when in the implant storage unit to the introduction condition when the implant moves through the exit opening and into the introducer sheath shaft, and the compression can be followed by the expanding of the implant from the introduction condition to the implantation condition. The thickness of the implant in the implantation condition can be smaller than in the storage condition.

The method can further comprise decoupling the apparatus from the introducer sheath prior to the removing of the introducer sheath from the hollow anatomical structure. The decoupling of the apparatus from the introducer sheath can comprise trimming the implant proximally of the introducer sheath.

The implant can comprise a fibrous body and a tether coupled to the body, and the method can comprise attaching the tether externally of the hollow anatomical structure to prevent distal migration of the body in the hollow anatomical structure. The attaching of the tether can occur after the removing of the introducer sheath and the introducer from the hollow anatomical structure. The attaching of the tether can comprise securing a proximal end of the tether to an external surface of the body, such as by adhesive tape. The attaching of the tether can comprise incorporating the proximal end of the tether into sutures that close an access site for the hollow anatomical structure.

A fourth embodiment comprises an apparatus for delivering an implant. The apparatus comprises a pushrod, a distal exit opening, and a pushrod passage receiving the pushrod and located proximal of the distal exit opening. The pushrod passage and the distal exit opening are located on a delivery path. The apparatus further comprises an elongate vascular implant stored in the apparatus. A portion of the implant is positioned at a first location on the delivery path, and the implant extends from the first location in a direction divergent from the delivery path.

Further optional features and variations of this fourth embodiment are presented in the following paragraphs. The present disclosure contemplates and includes employing these optional features and variations in the fourth embodiment (or in any other embodiment summarized or described herein), either alone or in any feasible combination of two or more such optional features and variations.

The pushrod can be stored in the apparatus generally in a loop configuration, and the implant can be stored (and/or an implant chamber can be located) in the apparatus alongside the pushrod so that the implant/chamber extends and curves along and next to the loop formed by the pushrod (or the pushrod housing). The implant (and/or the implant chamber) can generally conform to the shape of the loop as it extends and curves along the loop. The apparatus can include a casing generally shaped like a ring which contains the stored pushrod and the implant/chamber. The ring can generally conform to the pushrod loop and implant/chamber, and form a radially inward deflection from the ring configuration to expose a portion of the pushrod for manual gripping. The pushrod and the implant can diverge at distal portions thereof so that the pushrod exits the casing to expose a length of the pushrod for manual gripping. The pushrod and implant can be connected to each other near the distal tip of the pushrod.

The implant can comprise a bioabsorbable fibrous implant. The apparatus can further comprise an implant storage unit, and the implant can be stored in the unit in an expanded condition. At least a proximal portion of the implant can be stored in the unit with substantially no longitudinal bunching or folding.

The implant can be coupled to the pushrod at the first location.

A system can comprise the apparatus, and an introducer sheath coupled to the apparatus, wherein a proximal opening of the introducer sheath is aligned with the distal exit opening and located on the delivery path. The introducer sheath can be removably coupled to the apparatus.

The apparatus can further comprise an implant storage chamber which extends in a direction divergent from the delivery path, wherein the implant is stored in the storage chamber. The implant storage chamber can have a generally straight configuration. The implant storage chamber can have a curved configuration.

The pushrod can extend proximally from the pushrod passage to an exterior of the apparatus to facilitate gripping the pushrod at a location proximal of the passage. The apparatus can further comprise a pushrod container, wherein the pushrod extends further proximally from the pushrod passage into the pushrod container. The apparatus can further comprise an implant storage unit containing the implant, wherein the pushrod container is connected to the implant storage unit.

The apparatus can further comprise an implant chamber in which the implant is located. The implant chamber can have a proximal end and a distal end, wherein a portion of the pushrod is exposed to permit manual gripping at a grip location distal of the proximal end of the implant chamber. The grip location can be closer to the distal end of the implant chamber than to the proximal end thereof.

A fifth embodiment comprises a method of facilitating delivery of a vascular implant. The method can comprise the following acts, in any feasible order: (a) providing a delivery device comprising an implant chamber and a pushrod, the delivery device defining a delivery path passing through an exit opening of the delivery device; (b) holding the implant in the implant chamber; (c) connecting a distal end of the implant to a distal tip region of the pushrod; (d) positioning the distal tip region of the pushrod and the distal end of the implant on the delivery path, aligned with the exit opening, so that a distal movement of the pushrod causes the pushrod and the implant to advance through the exit opening; and (e) facilitating rapid connection of an introducer sheath to the delivery device and alignment of a proximal opening of the introducer sheath with the exit opening via a coupler, separate from the introducer sheath, configured to receive a proximal portion of the introducer sheath and connect to the delivery device distal of the exit opening.

Further optional features and variations of this fifth embodiment are presented in the following paragraphs. The present disclosure contemplates and includes employing these optional features and variations in the fifth embodiment (or in any other embodiment summarized or described herein), either alone or in any feasible combination of two or more such optional features and variations.

The method can further comprise sterilizing the delivery device including the pushrod and the implant chamber as an assembled unit, with the implant in the implant chamber.

The method can further comprise packaging the delivery device including the pushrod and the implant chamber as an assembled unit, with the implant in the implant chamber.

The method can further comprise providing to a medical practitioner the delivery device including the pushrod and the implant chamber as an assembled unit, with the implant in the implant chamber.

Holding the implant in the implant chamber can comprise holding the implant in an expanded state. The implant can tend toward the expanded state in the absence of external forces.

Holding the implant in the implant chamber can comprise holding at least a proximal portion of the implant with substantially no longitudinal bunching or folding.

The implant can comprise a bioabsorbable fibrous implant.

The delivery device can comprise a pushrod container and the method can further comprise storing a proximal portion of the pushrod in the pushrod container.

The method can further comprise arranging the implant chamber along a direction that diverges from the delivery path, and still further comprise locating the distal tip region of the pushrod on the delivery path.

The method can further comprise exposing a portion of the pushrod to permit manual gripping at a grip location distal of a proximal end of the implant chamber. The grip location can be closer to a distal end of the implant chamber than to the proximal end thereof.

The coupler can comprise a longitudinal opening formed therethrough, that aligns with the exit opening upon connection of the coupler to the delivery device. The coupler can further comprise a slot formed along a side of the coupler and communicating with the longitudinal opening to allow sideways entry of the introducer sheath into the coupler.

A sixth embodiment comprises method of facilitating delivery of an elongate, expandable, bioabsorbable vascular implant. The method can comprise the following acts, in any feasible order: (a) providing a delivery device comprising an implant chamber and a pushrod, the delivery device defining a delivery path passing through an exit opening of the delivery device; (b) holding the elongate, expandable, bioabsorbable vascular implant in the implant chamber in an expanded state; (c) connecting a distal end of the implant to a distal tip region of the pushrod; (d) positioning the distal tip region of the pushrod and the distal end of the implant on the delivery path, aligned with the exit opening, so that a distal movement of the pushrod causes the pushrod and the implant to advance through the exit opening; and (e) exposing a portion of the pushrod to permit manual gripping at a grip location proximal of a distal end of the implant chamber.

Further optional features and variations of this sixth embodiment are presented in the following paragraphs. The present disclosure contemplates and includes employing these optional features and variations in the sixth embodiment (or in any other embodiment summarized or described herein), either alone or in any feasible combination of two or more such optional features and variations.

The grip location can be closer to a proximal end of the implant chamber than to a distal end thereof. Exposing the portion of the pushrod can comprise arranging the implant chamber along a direction that diverges from the delivery path.

The method can further comprise sterilizing the delivery device including the pushrod and the implant chamber as an assembled unit, with the implant in the implant chamber.

The method can further comprise packaging the delivery device including the pushrod and the implant chamber as an assembled unit, with the implant in the implant chamber.

The method can further comprise providing to a medical practitioner the delivery device including the pushrod and the implant chamber as an assembled unit, with the implant in the implant chamber.

The implant can tend toward the expanded state in the absence of external forces.

Holding the implant in the implant chamber can comprise holding at least a proximal portion of the implant with substantially no longitudinal bunching or folding.

The delivery device can comprise a pushrod container, and the method can further comprise storing a proximal portion of the pushrod in the pushrod container.

The method can further comprise locating the distal tip region of the pushrod on the delivery path.

A seventh embodiment comprises an apparatus for introducing an implant into a hollow anatomical structure. The apparatus comprises a storage unit, an elongate vascular implant stored inside the storage unit and having a distal end, and a pushrod at least partially stored inside the storage unit and having a distal end coupled to the distal end of the implant. The implant diverges from adjacency with the pushrod as the implant extends away from the distal end of the pushrod, such that the pushrod forms a force application region near the distal end of the pushrod, the force application region being accessible for force application but separated from the implant.

Further optional features and variations of this seventh embodiment are presented in the following paragraphs. The present disclosure contemplates and includes employing these optional features and variations in the seventh embodiment (or in any other embodiment summarized or described herein), either alone or in any feasible combination of two or more such optional features and variations.

The storage unit can comprise a wall separating the force application region from the implant. The pushrod can be partially located exteriorly of the storage unit to expose a length of the pushrod, which forms the force application region, for gripping and can pass through the wall near a distal end of the storage unit.

The storage unit can comprise an exit opening, and the implant can diverge from adjacency with the pushrod in a proximal direction from the exit opening and can converge with the pushrod proximally of the exit opening as the pushrod is advanced toward and through the exit opening. The implant can be drawn toward and through the exit opening by the pushrod as the pushrod is so advanced. The storage unit can define a storage axis, the pushrod and the implant can have a common travel direction through the exit opening, and the storage axis can be offset relative to the common travel direction. The storage axis can be non-linear.

The storage unit is generally shaped like a ring.

The implant can comprise an occluding implant.

The implant can comprise a bioresorbable implant.

An eighth embodiment comprises an apparatus for introducing an implant into a hollow anatomical structure. The apparatus comprises a storage unit comprising an exit opening, an implant storage portion, and a pushrod storage portion spaced from the implant storage portion and converging with the implant storage portion at the exit opening, an elongate vascular implant stored inside the implant storage portion and having a distal end, and a pushrod at least partially stored inside the pushrod storage portion and having a distal end coupled to the distal end of the implant. The pushrod forms a force application region near the distal end of the pushrod. The implant and the pushrod continually converge proximally of the exit opening as the pushrod is advanced toward and through the exit opening.

Further optional features and variations of this eighth embodiment are presented in the following paragraphs. The present disclosure contemplates and includes employing these optional features and variations in the eighth embodiment (or in any other embodiment summarized or described herein), either alone or in any feasible combination of two or more such optional features and variations.

The implant can be drawn toward and through the exit opening by the pushrod as the pushrod is so advanced.

The implant storage portion and the pushrod storage portion can be physically separated from each other.

The storage unit can comprise a common casing defining the implant storage portion and the pushrod storage portion. The common casing can be generally shaped like a ring.

The pushrod can be partially located exteriorly of the pushrod storage portion to expose a length of the pushrod for gripping and can enter the storage unit near a distal end of the storage unit.

The implant can comprise an occluding implant.

The implant can comprise a bioresorbable implant.

A ninth embodiment comprises a method for introducing an implant into a hollow anatomical structure. The method can comprise the following acts, in any feasible order: (a) inserting an introducer sheath into the hollow anatomical structure; (b) coupling a delivery apparatus to a proximal end of the introducer sheath, the delivery apparatus storing a pushrod and an implant along divergent directions; (c) converging the pushrod and the implant along a common axis defining a travel direction within the delivery apparatus; and (d) distally advancing the converged pushrod and implant along the travel direction through an exit opening of the delivery apparatus and into the introducer sheath.

Further optional features and variations of this ninth embodiment are presented in the following paragraphs. The present disclosure contemplates and includes employing these optional features and variations in the ninth embodiment (or in any other embodiment summarized or described herein), either alone or in any feasible combination of two or more such optional features and variations.

The implant can comprise an occluding implant.

Converging the pushrod and the implant can comprise distally advancing the pushrod to draw the implant toward the common axis.

Distally advancing the converged pushrod and implant can comprise compressing the implant from an expanded condition to a compressed condition. The method can further comprise distally advancing the converged pushrod and implant through the introducer sheath and into the hollow anatomical structure and expanding the implant in the hollow anatomical structure from the compressed condition to the expanded condition.

Distally advancing the converged pushrod and implant can comprise gripping an exposed portion of the pushrod proximal of the converged pushrod and implant.

The hollow anatomical structure can comprise a blood vessel. The method can further comprise occluding a lumen of the blood vessel with the implant. The implant can be bioresorbable.

The hollow anatomical structure can comprise a vein in a leg.

A tenth embodiment comprises an apparatus for introducing an implant into a hollow anatomical structure. The apparatus comprises a storage unit having an exit opening and defining a chamber in communication with the exit opening, an elongate, self-expanding vascular implant having an expanded condition and stored within the chamber in the expanded condition, proximal of the exit opening, and a pushrod having a distal end aligned with and proximal of the exit opening. The pushrod is pre-assembled to a distal end of the implant.

Further optional features and variations of this tenth embodiment are presented in the following paragraphs. The present disclosure contemplates and includes employing these optional features and variations in the tenth embodiment (or in any other embodiment summarized or described herein), either alone or in any feasible combination of two or more such optional features and variations.

The pushrod and the implant can have a common travel direction through the exit opening such that the implant is drawn toward and through the exit opening by the pushrod as the pushrod is advanced toward and through the exit opening.

The apparatus can further comprise a guide proximal of the exit opening for facilitating compression of the implant from the expanded condition to a compressed condition as the pushrod is advanced toward and through the exit opening.

The pushrod can be stored within the chamber.

The chamber can be generally shaped like a ring.

The pushrod can be partially located exteriorly of the storage unit to expose a length of the pushrod for gripping and can enter the storage unit near a distal end of the storage unit.

The implant can comprise an occluding implant.

The implant can comprise a bioresorbable implant.

An eleventh embodiment comprises an apparatus for introducing an implant into a hollow anatomical structure. The apparatus comprises a storage unit having an exit opening and defining a chamber in communication with the exit opening, an elongate vascular implant having a first configuration in which the implant is larger than the exit opening and a second configuration in which the implant is smaller than the exit opening, and a pushrod having a distal end aligned with and proximal of the exit opening. The pushrod is pre-assembled to a distal end of the implant and the implant is stored within the chamber in the first configuration and proximal of the exit opening.

Further optional features and variations of this eleventh embodiment are presented in the following paragraphs. The present disclosure contemplates and includes employing these optional features and variations in the eleventh embodiment (or in any other embodiment summarized or described herein), either alone or in any feasible combination of two or more such optional features and variations.

The pushrod and the implant can have a common travel direction through the exit opening such that the implant is drawn toward and through the exit opening by the pushrod as the pushrod is advanced toward and through the exit opening.

The apparatus can further comprise a guide proximal of the exit opening for facilitating compression of the implant from the first configuration to the second configuration as the pushrod is advanced toward and through the exit opening.

The pushrod can be stored within the chamber.

The chamber can be generally shaped like a ring.

The pushrod can be partially located exteriorly of the storage unit to expose a length of the pushrod for gripping and can enter the storage unit near a distal end of the storage unit.

The implant can comprise an occluding implant.

The implant can comprise a bioresorbable implant.

A twelfth embodiment comprises a method for introducing an implant into a hollow anatomical structure. The method can comprise the following acts, in any feasible order: (a) inserting an introducer sheath into the hollow anatomical structure; (b) coupling a delivery apparatus to a proximal end of the introducer sheath, the delivery apparatus storing a vascular implant in an expanded condition, proximally of an exit opening of the delivery apparatus; and (c) compressing the implant to a size sufficient to fit through the exit opening while distally advancing the implant through the exit opening and into the introducer sheath.

Further optional features and variations of this twelfth embodiment are presented in the following paragraphs. The present disclosure contemplates and includes employing these optional features and variations in the twelfth embodiment (or in any other embodiment summarized or described herein), either alone or in any feasible combination of two or more such optional features and variations.

The implant can comprise an occluding implant.

Compressing the implant can further comprise compressing the implant to a size sufficient to fit in the introducer sheath.

Distally advancing the implant can comprise distally advancing a pushrod coupled to the implant. For example, distally advancing the implant can comprise gripping an exposed portion of the pushrod proximal of the converged pushrod and implant.

Distally advancing the implant through the exit opening can cause the compression of the implant.

The method can further comprise expanding the implant after distally advancing the implant into the hollow anatomical structure. For example, expanding the implant can comprise withdrawing the introducer sheath and allowing the implant to self-expand.

The implant can be radially larger than the exit opening in the expanded condition.

The hollow anatomical structure can comprise a blood vessel. The method can further comprise occluding a lumen of the blood vessel with the implant. The implant can be bioresorbable.

The hollow anatomical structure can comprise a vein in a leg.

A thirteenth embodiment comprises an elongate vascular implant for a hollow anatomical structure. The implant comprises a body formed by a number of generally parallel, longitudinally extending elongate fibers and having a distal end, multiple spaced bands coupled to and encircling the body, and a tether coupled with respect to the body and interacting with the bands to form multiple force application points acting on the body such that application of a proximal force to the tether causes the distance between the bands to decrease and the body to shorten and one of expand radially between the bands and increase in density between the bands.

Further optional features and variations of this thirteenth embodiment are presented in the following paragraphs. The present disclosure contemplates and includes employing these optional features and variations in the thirteenth embodiment (or in any other embodiment summarized or described herein), either alone or in any feasible combination of two or more such optional features and variations.

At least one of the body, the bands, and the tether can comprise a bioresorbable material.

The body can be elastic and the tether can be inelastic. For example, the tether can comprise an inelastic yarn.

The tether can be coupled to a distal end of the body.

The implant can further comprise an adjustably-sized loop passing through or coupled to the bands and coupled to or formed by the tether, such that applying a proximal force to the tether reduces the size of the loop and relatively draws the bands toward each other to decrease the distance between the bands. For example, the multiple spaced bands can comprise a proximal band and a distal band spaced distally from the proximal band, and the tether can sequentially extend from the body through the proximal band, reverse direction a first time and extend through the distal band, and reverse direction a second time to form the loop with the tether.

An apparatus for introducing an implant into a hollow anatomical structure can comprise the elongate vascular implant and a pushrod coupled to the implant, such that proximal movement of the implant is prevented by the pushrod when a proximal force is applied to the tether. A distal end of the pushrod can be coupled to the distal end of the implant.

A fourteenth embodiment comprises an elongate vascular implant for a hollow anatomical structure. The implant comprises a body formed by a number of generally parallel, longitudinally extending elongate fibers, multiple force application points coupled to the body, an adjustably-sized loop passing through or coupled to the force application points, and a tether, the loop being coupled to or formed by the tether. Application of a proximal force to the tether causes the loop to reduce in size, which relatively draws the force application points toward each other to shorten the body and one of expand radially the body between the force application points and increase the density of the body between the force application points.

Further optional features and variations of this fourteenth embodiment are presented in the following paragraphs. The present disclosure contemplates and includes employing these optional features and variations in the fourteenth embodiment (or in any other embodiment summarized or described herein), either alone or in any feasible combination of two or more such optional features and variations.

At least one of the body, the force application points, and the tether comprises a bioresorbable material.

The body can be elastic and the tether can be inelastic. For example, the tether can comprise an inelastic yarn.

The tether can be coupled to a distal end of the body.

An apparatus for introducing an implant into a hollow anatomical structure can comprise the elongate vascular implant and pushrod coupled to the implant, such that proximal movement of the implant is prevented by the pushrod when a proximal force is applied to the tether. A distal end of the pushrod can be coupled to a distal end of the implant.

A fifteenth embodiment comprises a method for treating a vein. The method can comprise the following acts, in any feasible order: (a) inserting an implant through an introducer sheath into the vein, the implant having a body and multiple spaced bands coupled to and encircling the body; (b) expanding the implant from a compressed condition to an expanded condition in the vein; and (c) moving the bands relative to each other with the implant in the expanded condition to shorten the body between the bands and one of further expand radially between the bands and increase in density between the bands.

Further optional features and variations of this fifteenth embodiment are presented in the following paragraphs. The present disclosure contemplates and includes employing these optional features and variations in the fifteenth embodiment (or in any other embodiment summarized or described herein), either alone or in any feasible combination of two or more such optional features and variations.

Inserting the implant through the introducer sheath can comprise compressing the implant from the expanded condition to the compressed condition.

Inserting the implant through the introducer sheath can comprise distally advancing a pushrod coupled with the implant through the introducer sheath. The method can further comprise preventing proximal movement of the implant with the pushrod during shortening of the body.

Expanding the implant can comprise withdrawing the introducer sheath from the implant within the vein.

Moving the bands relative to each other can comprise applying a proximal force to a tether coupled with respect to the body and interacting with the bands.

Shortening the body can comprise shortening a distal portion of the body. The vein can comprise the saphenous vein, and shortening the distal portion of the body can occur in a portion of the saphenous vein nearest the saphenofemoral junction.

A sixteenth embodiment comprises an apparatus for delivering an implant. The apparatus comprises a pushrod stored in the apparatus, the pushrod having a distal tip; and an elongate vascular implant stored in the apparatus, the implant being connected to the pushrod near the distal tip of the pushrod. The pushrod is stored in the apparatus generally in a loop configuration. The implant is stored in the apparatus alongside the pushrod so that the implant extends and curves along and next to the loop formed by the pushrod.

Further optional features and variations of this sixteenth embodiment are presented in the following paragraphs. The present disclosure contemplates and includes employing these optional features and variations in the sixteenth embodiment (or in any other embodiment summarized or described herein), either alone or in any feasible combination of two or more such optional features and variations.

The implant can generally conform to the shape of the loop as it extends and curves along the loop.

The apparatus can further comprise a casing generally shaped like a ring which contains the stored pushrod and implant. The ring can generally conform to the pushrod loop and implant, and the casing can form a radially inward deflection from the ring configuration to expose a portion of the pushrod for gripping. The pushrod and the implant can diverge at distal portions thereof so that the pushrod exits the casing to expose a length of the pushrod for gripping.

The apparatus can further comprise a distal exit opening, and a pushrod passage receiving the pushrod and located proximal of the distal exit opening, wherein the pushrod passage and the distal exit opening are located on a delivery path. A portion of the implant can be positioned at a first location on the delivery path, and the implant can extend from the first location in a direction divergent from the delivery path.

The apparatus can further comprise an inward-tapering channel located distal of the pushrod distal tip and aligned therewith, such that a distal movement of the pushrod advances the pushrod tip, and draws the implant, through the inward-tapering channel while the channel compresses the implant.

The apparatus can further comprise a distal exit opening, wherein the distal tip of the pushrod is aligned with and proximal of the exit opening so that a distal movement of the pushrod effects a distal advancement of both the pushrod and implant toward and through the exit opening.

The implant can be radially self-expanding, and be stored in the apparatus in an expanded state.

The pushrod can be stored in a pushrod housing, and the implant can be stored next to but outside of the pushrod housing.

The implant can be a bioabsorbable occluder.

A seventeenth embodiment comprises an apparatus for delivering an implant into a patient via a catheter. The apparatus comprises an exit opening configured for juxtaposition and communication with the catheter; a pushrod contained in the apparatus, the pushrod having a distal tip; and an elongate vascular implant contained in the apparatus. The implant is connected to the pushrod near the distal tip of the pushrod. The pushrod is contained in the apparatus generally in a loop configuration. The implant is contained in the apparatus alongside the pushrod so that the implant extends and curves along and next to the loop formed by the pushrod. The distal tip of the pushrod is aligned with the exit opening such that a distal advancement of the pushrod causes the distal tip to pass through the exit opening and the implant to be drawn through the exit opening along with the pushrod.

Further optional features and variations of this seventeenth embodiment are presented in the following paragraphs. The present disclosure contemplates and includes employing these optional features and variations in the seventeenth embodiment (or in any other embodiment summarized or described herein), either alone or in any feasible combination of two or more such optional features and variations.

The implant can generally conform to the shape of the loop as it extends and curves along the loop.

The apparatus can further comprise a casing generally shaped like a ring which contains the stored pushrod and implant. The ring can optionally generally conform to the pushrod loop and implant, and the casing can optionally form a radially inward deflection from the ring configuration to expose a portion of the pushrod for gripping. The pushrod and the implant can optionally diverge at distal portions thereof so that the pushrod exits the casing to expose a length of the pushrod for gripping.

The apparatus can further comprise the catheter, and the catheter can be coupled with respect to, and in communication with, the exit opening such that the pushrod and implant pass into a lumen of the catheter upon distal advancement of the pushrod.

The implant can be radially self-expanding, and is stored in the apparatus in an expanded state. The apparatus can optionally further comprise an inward-tapering channel located proximal of the exit opening and aligned therewith, such that a distal movement of the pushrod advances the pushrod tip, and draws the implant, through the inward-tapering channel while the channel compresses the implant.

The pushrod can be stored in a pushrod housing, and the implant can be stored next to but outside of the pushrod housing.

The implant can be a bioabsorbable occluder.

An eighteenth embodiment comprises a method. The method comprises holding a pushrod in a loop configuration; holding a self-expanding elongate vascular implant in an expanded state, alongside the pushrod in a curved configuration that conforms generally to the loop; receiving a distal tip of the pushrod together with a distal portion of the implant in an inward-tapering channel and compressing the implant with the channel as the pushrod advances into the channel and draws the implant through the channel; and conducting the pushrod and compressed implant with a lumen of a catheter in a distal direction beyond the channel.

Further optional features and variations of this eighteenth embodiment are presented in the following paragraphs. The present disclosure contemplates and includes employing these optional features and variations in the eighteenth embodiment (or in any other embodiment summarized or described herein), either alone or in any feasible combination of two or more such optional features and variations.

In the method, conducting the implant can comprise conducting the implant toward a blood vessel lumen. In the method, conducting the implant can comprise conducting the implant toward a vein lumen.

In the method, holding the pushrod and implant can comprise holding the pushrod and implant in a casing generally shaped like a ring.

In the method, holding the pushrod can comprise holding the distal tip of the pushrod in a position aligned with the channel such that distal advancement of the pushrod causes the distal tip to enter the channel.

A nineteenth embodiment comprises an apparatus for advancing a vascular implant into a blood vessel. The apparatus comprises a first elongate member, the first elongate member having sufficient column strength to function as a pusher member; and a second elongate member, the second elongate member being thinner than the first elongate member and extending to a distal end located at a first point which is at or near a distal end of the first elongate member. The elongate members form an implant retaining portion while the distal end of the second elongate member is located at the first point, the implant retaining portion being located proximal of the first point. The implant retaining portion comprising a space located between the elongate members and configured for receiving an implant portion, with the first elongate member on one side of the space and the second elongate member on another side. The implant retaining portion further comprises a proximal side and a distal side which further circumscribe the space, the proximal and distal sides being effective to prevent an implant received in the retaining portion from moving out of engagement with the retaining portion as the first elongate member is moved distally and proximally. The implant retaining portion is removable by withdrawing the second elongate member in a proximal direction with respect to the first elongate member, thereby moving the distal end of the elongate member proximally beyond the former location of the implant retaining portion.

Further optional features and variations of this nineteenth embodiment are presented in the following paragraphs. The present disclosure contemplates and includes employing these optional features and variations in the nineteenth embodiment (or in any other embodiment summarized or described herein), either alone or in any feasible combination of two or more such optional features and variations.

The apparatus can further comprise an elongate vascular implant having a distal portion retained within the retaining portion. The elongate vascular implant can optionally extend proximally from the implant retaining portion. The implant retaining portion can optionally grip the implant sufficiently to permit the first elongate member to push and pull the implant through a confined space.

The second elongate member can be not configured for tissue penetration.

The second elongate member can extend proximally beyond a proximal end of the first elongate member. The implant retaining portion can optionally be removable by manipulating a proximal portion of the second elongate member that extends proximally beyond the proximal end of the first elongate member. The implant retaining portion can optionally be removable by distally pulling a proximal portion of the second elongate member that extends proximally beyond the proximal end of the first elongate member, to withdraw the distal end of the second elongate member proximally from the first point.

The first elongate member can comprise a pushrod having an internal lumen that receives the second elongate member. The second elongate member can optionally extend proximally from the first point, pass radially outward of the pushrod to form the implant retaining portion, and then radially inward into the pushrod lumen proximal of the implant retaining portion, and then proximally within the pushrod lumen toward a proximal end of the pushrod. A distal portion of the second elongate member can be within the pushrod lumen, proximal of the former location of the implant retaining portion, when the implant retaining portion is removed. The second elongate member can optionally extend proximally from the first point, and be substantially straight as it extends through and forms the implant retaining portion, and then extend proximally within the pushrod lumen toward a proximal end of the pushrod.

The first elongate member can have an insertable shaft portion with a maximum radial profile that defines a circle, and the radial profile can define the outermost radial extent of the apparatus along the insertable length of the apparatus when the implant retaining portion is removed.

The second elongate member can be metallic.

The implant retaining portion can be located at a sidewall opening of the first elongate member, and the sidewall opening can face radially outward in a direction transverse to the longitudinal axis of the first elongate member.

The second elongate member can be removably connected to the first elongate member at the first point.

A twentieth embodiment comprises an apparatus. The apparatus comprises an elongate rod sized for insertion into a blood vessel lumen, the rod having a distal end, at least one sidewall opening near the distal end and an internal lumen extending proximally of the sidewall opening; an elongate member positioned in the rod and extending to an elongate member endpoint at or near the distal end of the rod; and an implant grip located proximal of the elongate member endpoint and comprising a space between the rod and the elongate member that is bounded on at least four sides thereof and is configured to prevent disengagement of an implant portion secured in the space when the rod is moved distally and proximally within a constraining lumen. The elongate member extends proximally within the lumen of the rod, proximal of the implant grip. The implant grip can be removable by withdrawing the elongate member in a proximal direction with respect to the rod, thereby moving the distal end of the elongate member proximally beyond the former location of the implant grip.

Further optional features and variations of this twentieth embodiment are presented in the following paragraphs. The present disclosure contemplates and includes employing these optional features and variations in the twentieth embodiment (or in any other embodiment summarized or described herein), either alone or in any feasible combination of two or more such optional features and variations.

The implant grip can be formed at least in part by a portion of the elongate member that extends radially outward from the elongate rod via the sidewall opening.

The apparatus can further comprise an elongate vascular implant having a distal portion gripped by the implant grip. The elongate vascular implant can optionally extend proximally from the implant grip.

The implant grip can grip the implant sufficiently to permit the elongate rod to push and pull the implant through a confined space.

The elongate member can be not configured for tissue penetration.

The elongate member can extend proximally beyond a proximal end of the elongate rod. The implant grip can optionally be removable by manipulating a proximal portion of the elongate member that extends proximally beyond the proximal end of the elongate rod. The implant grip can optionally be removable by distally pulling a proximal portion of the elongate member that extends proximally beyond the proximal end of the elongate rod, to withdraw the distal end of the elongate proximally.

The elongate member can extend proximally from the elongate member endpoint, pass radially outward of the elongate rod to form the implant grip, and then radially inward into the elongate rod lumen proximal of the implant grip, and then proximally within the elongate rod lumen toward a proximal end of the elongate rod.

A distal portion of the elongate member can be within the elongate rod lumen, proximal of the former location of the implant grip, when the implant grip is removed.

The elongate member can extend proximally from the elongate member endpoint, and be substantially straight as it extends through and forms the implant grip, and then extend proximally within the elongate rod lumen toward a proximal end of the elongate rod.

The elongate rod can have an insertable shaft portion with a maximum radial profile that defines a circle, and the radial profile can define the outermost radial extent of the apparatus along the insertable length of the apparatus when the implant grip is removed.

The elongate member can be metallic.

The sidewall opening can face radially outward in a direction transverse to the longitudinal axis of the rod.

The elongate member can be removably connected to the rod at the elongate member endpoint.

A twenty-first embodiment comprises a method. The method comprises inserting an introducer sheath into a blood vessel; pushing an elongate, bioresorbable vascular implant into the vessel through the sheath via a pushrod. The pushrod holds the distal end of the implant in an implant grip formed on one side by the pushrod and on another side by a retractable elongate flexible member received within a lumen of the pushrod proximal of the implant grip and extending to a flexible member endpoint distal of the implant grip. The elongate flexible member passes through or along a sidewall opening of the pushrod as the flexible member extends from the pushrod lumen to the flexible member endpoint. The method further comprises releasing the implant from the pushrod by retracting the elongate flexible member proximally of the sidewall opening and into the lumen of the pushrod; and reducing the chance of snagging or displacing the portion of the implant positioned in the vessel when withdrawing the pushrod, by causing the pushrod to take on a maximum radial profile no larger than that of a proximal insertable shaft portion of the pushrod once the elongate flexible member has been withdrawn into the lumen of the pushrod.

Further optional features and variations of this twenty-first embodiment are presented in the following paragraphs. The present disclosure contemplates and includes employing these optional features and variations in the twenty-first embodiment (or in any other embodiment summarized or described herein), either alone or in any feasible combination of two or more such optional features and variations.

The method can further comprise pulling a portion of the implant proximally with the pushrod and implant grip, after pushing the implant into the vessel but before releasing the implant from the implant grip.

The method can further comprise expanding or increasing the density of a distal portion of the implant by pulling the distal portion of the implant proximally with the pushrod and implant grip, after pushing the implant into the vessel but before releasing the implant from the implant grip.

The blood vessel can comprise a vein in a leg. The method can optionally further comprise occluding the vein with the implant.

The method can further comprise withdrawing the introducer sheath from the blood vessel while leaving the implant in position in the vessel. The method can optionally further comprise holding the implant in position in the vessel with the pushrod while withdrawing the sheath. The method can optionally further comprise allowing the implant to self-expand within the vessel by virtue of withdrawing the sheath.

The sidewall opening can face radially outward in a direction transverse to the longitudinal axis of the pushrod.

The elongate flexible member can be removably connected to the pushrod at the flexible member endpoint, and releasing the implant can comprise disconnecting the flexible member from the pushrod.

A twenty-second embodiment comprises an apparatus for inserting an implant into a blood vessel. The apparatus comprises an elongate rod sized for insertion into a blood vessel lumen, the rod having a sidewall, a distal end, at least one sidewall opening near the distal end and an internal lumen extending proximally of the sidewall opening; and an elongate member positioned in the rod and extending to an elongate member endpoint located distal of the sidewall opening, the elongate member extending proximally along or through the sidewall opening and into the elongate rod lumen, proximally of the sidewall opening. The sidewall opening has an upper edge, and the sidewall opening extends into the rod to a first depth. The upper edge extends distally from the first depth while sloping upward so that the sidewall opening gradually becomes shallower as it extends distally, the upper edge thereby forming a distal slope. The sidewall opening is configured, by virtue of the distal slope, to gently urge outward from the opening any implant material located in the sidewall opening as the rod is retracted, thereby reducing snagging.

Further optional features and variations of this twenty-second embodiment are presented in the following paragraphs. The present disclosure contemplates and includes employing these optional features and variations in the twenty-second embodiment (or in any other embodiment summarized or described herein), either alone or in any feasible combination of two or more such optional features and variations.

The apparatus can further comprise an elongate vascular implant with a portion received and secured between the rod and the elongate member. The received portion of the implant can optionally traverse from one side of the rod and elongate member through a space between the rod and elongate member to the other side of the rod and elongate member. The implant can optionally form two legs which extend proximally from the received portion of the implant. The implant can optionally comprise a bundle of bioresorbable fibers. The rod and the elongate member can optionally grip the fibers therebetween. The rod and the elongate member can optionally form an implant grip located proximal of the elongate member endpoint and comprising a space between the rod and the elongate member that is bounded on at least four sides thereof and is configured to prevent disengagement of the implant portion when the rod is moved distally and proximally within a constraining lumen.

The upper edge of the sidewall opening can extend proximally from the first depth while sloping upward so that the sidewall opening gradually becomes shallower as it extends proximally, the upper edge thereby forming a proximal slope. The sidewall opening can optionally be configured, by virtue of the proximal slope, to gently urge any material of the implant found to be in the sidewall opening outward therefrom as the rod is pushed distally with the apparatus in the release configuration.

The distal slope can be angled or curved.

The elongate member can extend radially outward from the sidewall opening and the rod to form an implant grip. The elongate member can optionally no longer extend radially outward from the sidewall opening and the rod when the apparatus is in the release configuration.

The rod can have an insertable shaft portion with a maximum radial profile that defines a circle, and said radial profile can define the outermost radial extent of the apparatus along the insertable length of the apparatus when the apparatus is in the release configuration.

The elongate member can be substantially straight as it extends from the elongate member endpoint to the elongate rod lumen proximal of the sidewall opening.

The sidewall opening can face radially outward in a direction transverse to the longitudinal axis of the rod.

The elongate member can be removably connected to the rod at the elongate member endpoint.

A twenty-third embodiment comprises an apparatus. The apparatus comprises an elongate vascular implant; an elongate rod sized for insertion into a blood vessel lumen, the rod having a sidewall, a distal end, at least one sidewall opening near the distal end and an internal lumen extending proximally of the sidewall opening; and an elongate member positioned in the rod and extending to an elongate member endpoint located distal of the sidewall opening, the elongate member extending proximally along or through the sidewall opening and into the elongate rod lumen, proximally of the sidewall opening, the elongate member being retractable into the elongate rod lumen proximal of the sidewall opening to form a release configuration of the apparatus. The sidewall opening has an upper edge, and the sidewall opening extends into the rod to a first depth. The upper edge extends distally from the first depth while sloping upward so that the sidewall opening gradually becomes shallower as it extends distally, the upper edge thereby forming a distal slope. A portion of the implant is received and secured between the elongate rod and the elongate member. The sidewall opening is configured, by virtue of the distal slope, to gently urge any material of the implant found to be in the sidewall opening outward therefrom as the rod is retracted with the apparatus in the release configuration.

Further optional features and variations of this twenty-third embodiment are presented in the following paragraphs. The present disclosure contemplates and includes employing these optional features and variations in the twenty-third embodiment (or in any other embodiment summarized or described herein), either alone or in any feasible combination of two or more such optional features and variations.

The received portion of the implant can traverse from one side of the rod and elongate member through a space between the rod and elongate member to the other side of the rod and elongate member. The implant can optionally form two legs which extend proximally from the received portion of the implant. The implant can optionally comprise a bundle of bioresorbable fibers. The rod and the elongate member can optionally grip the fibers therebetween.

The upper edge of the sidewall opening can extend proximally from the first depth while sloping upward so that the sidewall opening gradually becomes shallower as it extends proximally, the upper edge thereby forming a proximal slope. The sidewall opening can optionally be configured, by virtue of the proximal slope, to gently urge any material of the implant found to be in the sidewall opening outward therefrom as the rod is pushed distally with the apparatus in the release configuration.

The distal slope can be angled or curved.

The elongate member can extend radially outward from the sidewall opening and the rod to form an implant grip. The elongate member can optionally no longer extend radially outward from the sidewall opening and the rod when the apparatus is in the release configuration.

The rod can have an insertable shaft portion with a maximum radial profile that defines a circle, and the radial profile can define the outermost radial extent of the apparatus along the insertable length of the apparatus when the apparatus is in the release configuration.

The elongate member can be substantially straight as it extends from the elongate member endpoint to the elongate rod lumen proximal of the sidewall opening.

The rod and the elongate member can form an implant grip located proximal of the elongate member endpoint and comprising a space between the rod and the elongate member that is bounded on at least four sides thereof and is configured to prevent disengagement of the implant portion when the rod is moved distally and proximally within a constraining lumen.

The sidewall opening can face radially outward in a direction transverse to the longitudinal axis of the rod.

The elongate member can be removably connected to the rod at the elongate member endpoint.

A twenty-fourth embodiment comprises a method. The method comprises inserting an introducer sheath into a blood vessel; pushing an elongate, bioresorbable vascular implant into the vessel through the sheath via a pushrod. The pushrod holds the distal end of the implant in an implant grip formed on one side by the pushrod and on another side by a retractable elongate flexible member received within a lumen of the pushrod proximal of the implant grip and extending to a flexible member endpoint distal of the implant grip. The elongate flexible member passes through or along a sidewall opening of the pushrod as it extends from the pushrod lumen to the flexible member endpoint. The method further comprises releasing the implant from the pushrod by retracting the elongate flexible member proximally of the sidewall opening; and withdrawing the pushrod proximally from the portion of the implant positioned in the blood vessel while gently urging any implant material found to be in the sidewall opening outward therefrom.

Further optional features and variations of this twenty-fourth embodiment are presented in the following paragraphs. The present disclosure contemplates and includes employing these optional features and variations in the twenty-fourth embodiment (or in any other embodiment summarized or described herein), either alone or in any feasible combination of two or more such optional features and variations.

In the method, gently urging any implant material comprises doing so with a sloping portion of the sidewall opening.

The method can further comprise avoiding snagging or displacing the portion of the implant positioned in the vessel when withdrawing the pushrod by virtue of the gently urging.

The method can further comprise reducing the chance of snagging or displacing the portion of the implant positioned in the vessel when withdrawing the pushrod, by causing the pushrod to take on a maximum radial profile no larger than a proximal insertable shaft portion of the pushrod once the elongate flexible member has been drawn into the lumen of the pushrod.

The method can further comprise pulling a portion of the implant proximally with the pushrod and implant grip, after pushing the implant into the vessel but before releasing the implant from the implant grip.

The method can further comprise expanding or increasing the density of a distal portion of the implant by pulling the distal portion of the implant proximally with the pushrod and implant grip, after pushing the implant into the vessel but before releasing the implant from the implant grip.

In the method, the blood vessel can comprise a vein in a leg. The method can optionally further comprise occluding the vein with the implant.

The method can further comprise withdrawing the introducer sheath from the blood vessel while leaving the implant in position in the vessel. The method can optionally further comprise holding the implant in position in the vessel with the pushrod while withdrawing the sheath. The method can optionally further comprise allowing the implant to self-expand within the vessel by virtue of withdrawing the sheath.

In the method, the sidewall opening can face radially outward in a direction transverse to the longitudinal axis of the pushrod.

The elongate member can be removably connected to the pushrod at the flexible member endpoint, and releasing the implant can comprise disconnecting the flexible member from the pushrod.

Certain objects and advantages of the disclosed embodiments are described herein. Of course, it is to be understood that not necessarily all such objects or advantages may be achieved in accordance with any particular embodiment. Thus, for example, an embodiment may be practiced or carried out in a manner that achieves or optimizes one advantage or group of advantages as taught herein without necessarily achieving other objects or advantages as may be taught or suggested herein.

Despite the foregoing discussion of certain embodiments, only the appended claims, and such other claims as may be presented in the future based on the disclosure herein (and not the present Summary), are intended to define the invention(s) protected hereby. The summarized embodiments, and other embodiments, are presented in the following detailed description having reference to the attached figures.

BRIEF DESCRIPTION OF THE DRAWINGS

In the drawings:

FIG. 15 illustrates the leg of FIG. 1 with a shaft of the introducer sheath of FIG. 3 located in the greater saphenous vein of the leg.

FIG. 16 is a view similar to FIG. 15 with the distal coupler of the apparatus of FIG. 5 mounted to the introducer sheath.

FIG. 17 is a view similar to FIG. 16 with the apparatus of FIG. 5 mounted to the distal coupler and introducer sheath.

FIG. 18 is a view similar to FIG. 15A with the introducer of FIG. 11 and the implant of FIG. 2 fully advanced into the introducer sheath in the greater saphenous vein.

FIG. 19 is a view similar to FIG. 16 during removal of the apparatus from the distal coupler and the introducer sheath.

FIG. 20 is a view similar to FIG. 19 after removal of the apparatus from the distal coupler and the introducer sheath and trimming of the implant.

FIG. 21 is a view similar to FIG. 18 after removal of the distal coupler and the introducer sheath from the greater saphenous vein.

FIG. 22 is a view similar to FIG. 19 illustrating release of the implant from the introducer.

FIG. 23 is a view similar to FIG. 22 illustrating the implant in the greater saphenous vein after removal of the introducer from the greater saphenous vein.

FIG. 24 illustrates the leg after implantation of the implant in the greater saphenous vein.

FIG. 24A is a plan view of the exterior region of the leg labeled "XXIV-A" in FIG. 24.

FIG. 26 is an elevation view of a system according to another embodiment comprising the introducer sheath of FIG. 3 and an embodiment of an apparatus for storage and/or introduction of the implant of FIG. 2.

FIG. 28 is a side view of a right housing shell of the apparatus.

FIG. 29 is a side view of a left housing shell of the apparatus.

FIG. 66 is an enlarged sectional view of another embodiment of an introducer, particularly the proximal end of the introducer.

FIG. 67 is an enlarged top view of the introducer from FIG. 66.

DETAILED DESCRIPTION

The disclosed embodiments relate generally to a method and apparatus for storage and/or introduction of an implant into a hollow anatomical structure (HAS). The term "hollow anatomical structure" is a broad term and is used in its ordinary sense, including, without limitation, veins, arteries, gastric structures, coronary structures, pulmonary structures, tubular structures associated with reproductive organs such as fallopian tubes, uteri, hollow organs and the like. Hollow anatomical structures particularly suited to treatment or occlusion by the methods and apparatuses of the disclosed embodiments include veins, such as veins of the lower extremities, for example, veins in the leg, and fallopian tubes.

Figure 1:
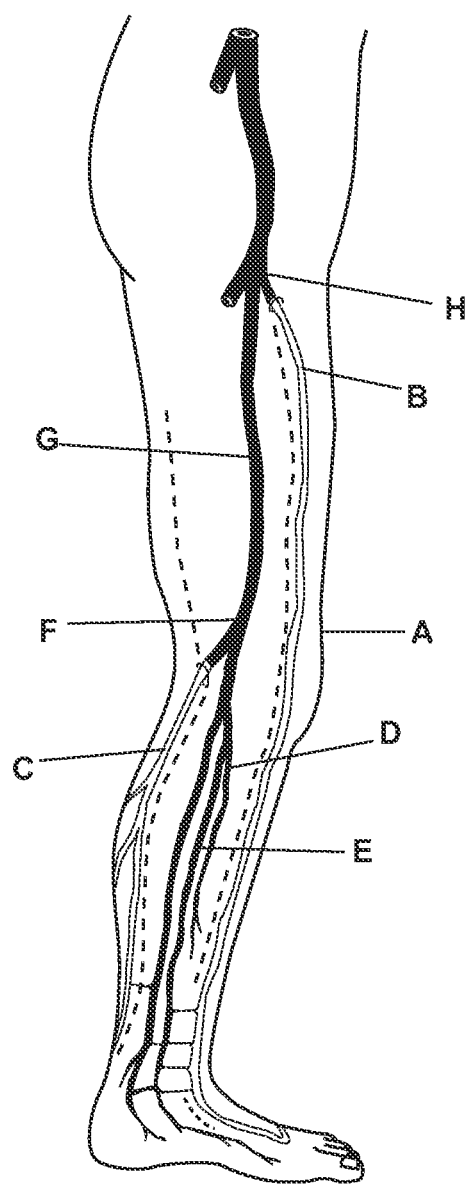
FIG. 1 is a schematic view of a human leg and portions of the deep and superficial venous systems.

Methods, systems, and apparatuses for occluding a hollow anatomical structure, such as the veins shown in FIG. 1, in a patient or subject using an implant such as occluding device or occluding material are disclosed. The terms "subject" and "patient" as used herein, refer to animals, such as mammals. For example, mammals contemplated by one skilled in the art include humans, primates, dogs, cats, sheep, cattle, goats, pigs, horses, mice, rats, rabbits, guinea pigs, and the like. The terms "subject" and "patient" are used interchangeably.

The terms "occluding device," "occluding implant," and "occluding material" as used herein are broad terms and are used in their ordinary sense, including, without limitation, a substance or device that is capable of occluding or causing occlusion of a HAS. Occluding materials or occluding devices can be formed or fabricated ex situ or formed in situ (e.g., by curing of a prepolymer or uncured polymer). The term "occluding material" as employed herein, includes prepolymers, uncured polymers, unsolidified materials, as well as occluding materials inserted into a patient in polymerized, procured, or solidified form. Biologic materials, e.g., gelatin and thrombin, can also be used separately or in combination with the occlusive materials. Bioresorbable materials are exemplary occluding materials, although other materials can also be used as desired. For example, in one embodiment, the occluding implant can include fibers and/or other components formed from polylactides (PLA) and/or polyglycolides (PGA) or copolymers thereof.

Occluding can include, but is not limited to, blocking by insertion of a plug or other structure into the HAS, such as any one or combination of the veins shown in FIG. 1, that prevents or inhibits flow therethrough, adhering opposite walls of the HAS together so as to prevent or inhibit flow therethrough, compressing the walls of the HAS together so as to prevent or inhibit flow therethrough, or initiating a physiological reaction to an applied force or substance (e.g., energy, chemicals, drugs, physical contact, pressure or the like) that causes flow through the HAS to be inhibited or prevented (e.g., formation of a fibrotic plug or growth of connective tissue). Occlusion can be immediate, or onset of occlusion can be delayed. Occlusion can be partial (i.e., permitting a reduced flow through the HAS) or complete (i.e., permitting no or substantially no flow through the HAS). Occlusion can be permanent or temporary. Occlusion can be affected by resorption characteristics of the material. Occlusion can result in physical change or damage to the HAS (e.g., tissue fibrosis or necrosis) or can block the HAS without substantial physical change (e.g., a biocompatible plug). The mechanisms by which occlusion can occur include but are not limited to formation of an organized fibrotic occlusion resulting from the body's natural foreign body healing response, formation of a wound or damage to tissue, expansion of the occluding device or occluding material, release of a chemical or bioactive agent (e.g., a sclerosant, inflammatory agent, cytokine, growth factor, clotting factor, tissue attachment factor, or other agent) from the occluding device or occluding material, venoconstriction, compression, and ligation.

Figure 2:
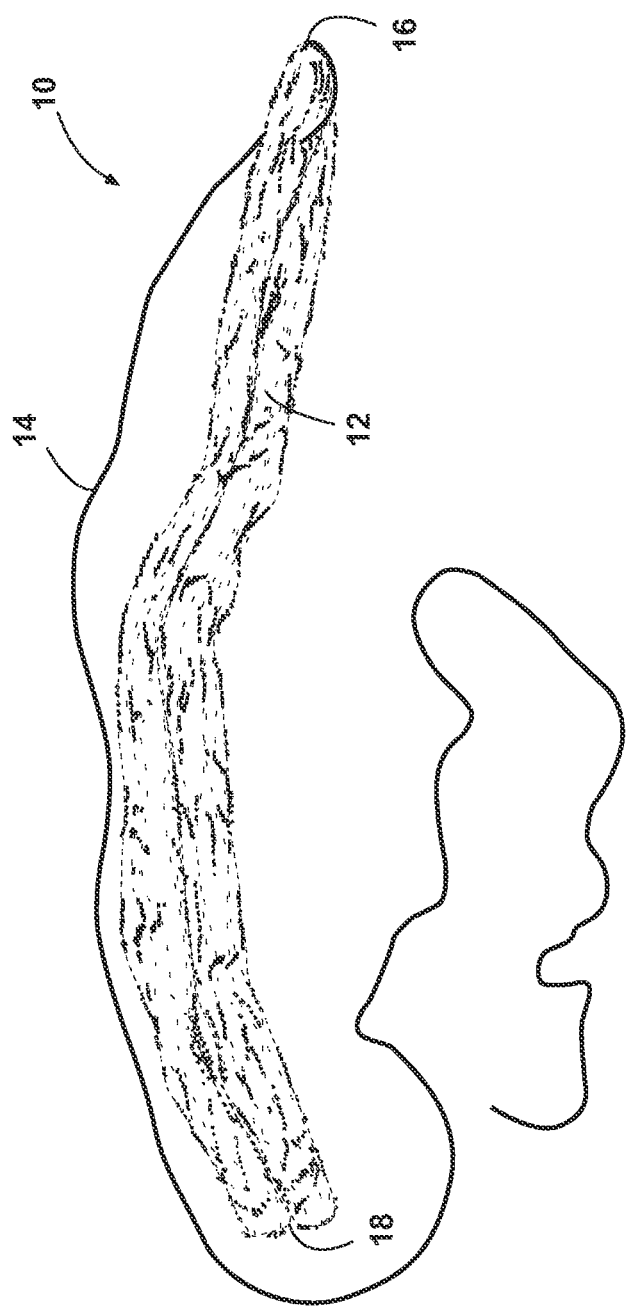
FIG. 2 is an elevation view of an embodiment of an implant for occluding a hollow anatomical structure, such as a vein in the venous systems shown in FIG. 1.

Referring to FIG. 2, an implant 10 according to one embodiment for occlusion of a hollow anatomic structure comprises a bioresorbable body 12. In one embodiment, the body 12 comprises a bioresorbable material in fibrous form, which can comprise a collection of individual fibers that can be spun into multi-filament yarns. The fibers or yarns can be textured to impart bulk. In one embodiment, multiple fibers or yarns can be assembled together to form the body 12. The textured fibers or yarns can be made wavy to prevent adjacent yarns from lying closely together; some fibers or yarns may tangle together. The fibers can be treated and/or agglomerated in any suitable manner to achieve a desired texture, density, geometry, etc. The fibers can be made or treated such that the body 12 can be compressible and/or expandable. For example, as shown in the illustrated embodiment, the body 12 can naturally assume an expanded condition and convert to a compressed condition upon application of a compressive force. Alternatively, the body 12 can naturally assume a compressed condition and convert to an expanded condition upon application of an expansive force. The bioresorbable material can be any suitable bioresorbable material, such as a material from the family of alpha hydroxy acids, for example polylactide (PLA) and/or polyglycolide (PGA).

Suitable forms and materials for the bulked fibrous bioresorbable body (and/or individual yarns or fibers) are disclosed in U.S. Patent Application Publication No. 2006/0212127, published Sep. 21, 2006, and entitled, "Structures for Permanent Occlusion of a Hollow Anatomical Structure," and in U.S. Patent Application Publication No. 2007/0248640, published Oct. 25, 2007, and entitled, "Occlusive Implant and Methods for Hollow Anatomical Structure." Of those publications, the following is incorporated herein by reference: paragraphs 0010-0171 of Publication No. 2007/0248640 and the drawings referenced in those paragraphs.

In the embodiment of FIG. 2, the implant further includes a tether 14 coupled to the body 12. As one example, the body 12 can be generally elongated with a distal end 16 and a proximal end 18, the distance between the distal end 16 and the proximal end 18 (i.e., the length of the body 12) optionally being greater than the cross-sectional diameter of the body 12, and the tether 14 is coupled near or to the distal end 16 of the body 12. The tether 14 can be coupled to the body 12 in any suitable manner, examples of which include tying or stitching the tether 14 to the body 12, employing a coupling agent, such as a bioresorbable or non-bioresorbable adhesive, and making the tether 14 integral with the body 12. In the embodiment of FIG. 2, the tether 14 is coupled to the body 12 by tying the tether 14 around the body 12 near a center of the length of the body 12, and the body 12 is bent or turned where the tether 14 is coupled to the body 12 such that the body 12 is folded upon itself. As a result of this configuration, the coupling location of the tether 14 forms the distal end 16 of the body 12, and the free ends of the body 12 folded upon each other form the proximal end 18 of the body 12. The tether 14 can have any suitable length relative to the length of the body 12. For example, the length of the tether 14 can be greater than, equal to, or less than that of the body 12.

The tether 14 can be bioresorbable and made of the same material as the body 12 or of a material different than that of the body 12. Alternatively, the tether 14 can be non-bioresorbable. Further, the tether 14 can be inelastic or elastic. In the illustrated embodiment of FIG. 2, the tether 14 is made of the same bioresorbable material as the body 12; the body 12 comprises multiple fibers processed and textured such that the body 12 is bulked, elastic, and compressible, and the tether 14 comprises multiple fibers spun into a single, relatively smooth, and inelastic yarn, wherein the cross-sectional diameter of the body 12 in its natural expanded condition is significantly greater than the cross-sectional diameter of the tether 14.

The implant 10 can be positioned in a HAS to occlude the HAS such that blood flow through the HAS is reduced or prevented. While the implant 10 can be positioned in the HAS in any suitable manner, such as the manners disclosed in the above-incorporated material from a patent application publication, additional or alternative techniques and/or apparatus can be employed, as discussed herein.

In one embodiment, the implant body 12 has an overall linear mass density of 7200 denier, and is formed from 48 plies of 75 denier, 30 filament, 100% polyglycolide (PGA) yarns. The PGA material has a molecular weight (Mn) over 12,750 and a polydispersity (PDI) between 1.1 and 1.8. A 30 cm length of the collected 48 plies has a breaking load between 30 and 50 lbf. Among the 48 plies, 24 are "S" twisted and 24 are "Z" twisted, all with a false twist texture of 90 twists per inch. The yarns are false twisted individually using pin twist texturing. The 48 plies are doubled over once at the distal end 16 of the body 12 to create a 7200 denier implant body 12. The tether 14 is formed from 16 plies of 75 denier, 30 filament, 100% polyglycolide (PGA) yarns. The filament denier is 2.5, or about 2.5. All 16 plies are "Z" twisted between 3 and 4 twists per inch and heat set. A 40 cm length of the collected 16 plies has a breaking load between 10 and 17 lbf.

The 48-ply yarn is preferably cleaned by passing it in "reel to reel" fashion through an ultrasonic cleaning bath filled with >99% isopropyl alcohol at a temperature maintained below 85 degrees Fahrenheit. The alcohol is replaced at a rate sufficient to clean no more than 100 grams of yarn per gallon of alcohol. After the cleaning bath the yarn is dried by running it past one or more drying air jets.

After cleaning and drying, the yarn can be further bulked by heating. From a supply reel, the yarn is passed through a roller set and then downward in a generally vertical orientation from the roller set, and through a vertically oriented cylindrical heating chamber positioned below the roller set. A takeup reel positioned below and to the side of the lower end of the heating chamber takes up the yarn after it moves through and past the heating chamber. The roller set above the heating chamber pulls the yarn from the supply reel and pushes it downward through the heating chamber. The takeup reel is driven at a speed or speeds that leave the yarn fairly slack between the roller set and the takeup reel, and the yarn passes through the heating chamber in this slack condition so that the filaments separate somewhat for heating. The heating chamber is 4 inches long and 2 inches in inside diameter and the yarn is fed into the heating chamber at a feed speed of 0.0124 meters per second. The heating chamber heats the passing yarn with a circumferential hot air flow directed inwardly at the yarn, which travels approximately along the central vertical axis of the chamber. Air is flowed at a pressure of 60 PSI (+/−5 PSI) through a heater operated at a temperature of 250-350 degrees Fahrenheit, preferably 275 degrees. The heated, pressurized air then flows into the chamber via a circumferential opening or "slit" formed in the chamber inner wall. The temperature inside the chamber, measured at the chamber inner wall next to the circumferential slit (and the incoming airflow) is 155-165 degrees Fahrenheit. The circumferential arrangement of the hot air inflow helps to prevent asymmetric inward airflows which can tend to blow the yarn off-axis and induce tension in the yarn and thereby disrupt the bulking.

The dried and heat-bulked yarn can then be cut to the appropriate length (preferably 50 cm) and the tether 14 is tied to the midpoint. The two halves of the yarn are folded against each other to form the implant body 12 with the tether 14 tied at the distal end of the body 12.

The above specified parameters for the implant body 12 and tether 14 can be varied or disregarded in other embodiments. The implant body 12 can have a linear mass density between 6000 and 8000, or between 4000 and 10,000. Between 60 and 120, or between 40 and 140, or between 20 and 200 twists per inch can be employed in texturing the plies/fibers/filaments of the implant body 12. The number and size of the plies can be varied, or a single ply can be employed. Where multiple plies are employed in the body 12, half can be "S" twisted and half can be "Z" twisted. Bioabsorbable materials other than PGA, such as polylactic acid (PLA), or any other suitable bioabsorbable or bioresorbable material specified herein can be employed, either alone or in combination with other such materials. For example, a mixture of PGA and PLA plies/fibers/filaments can be used. Non-bioabsorbable or non-bioresorbable materials can be employed as well. The filament denier in the body 12 can vary between 1.5 and 3.5, or between 0.5 and 5.0, while the filament count can vary between 2000 and 4000, or between 1000 and 5000, or otherwise to fall within the above specified ranges for linear mass density. Where PGA is used in forming the body 12, the molecular weight (Mn) can vary between 10,000 and 15,000, or between 5,000 and 20,000.

Figure 3:
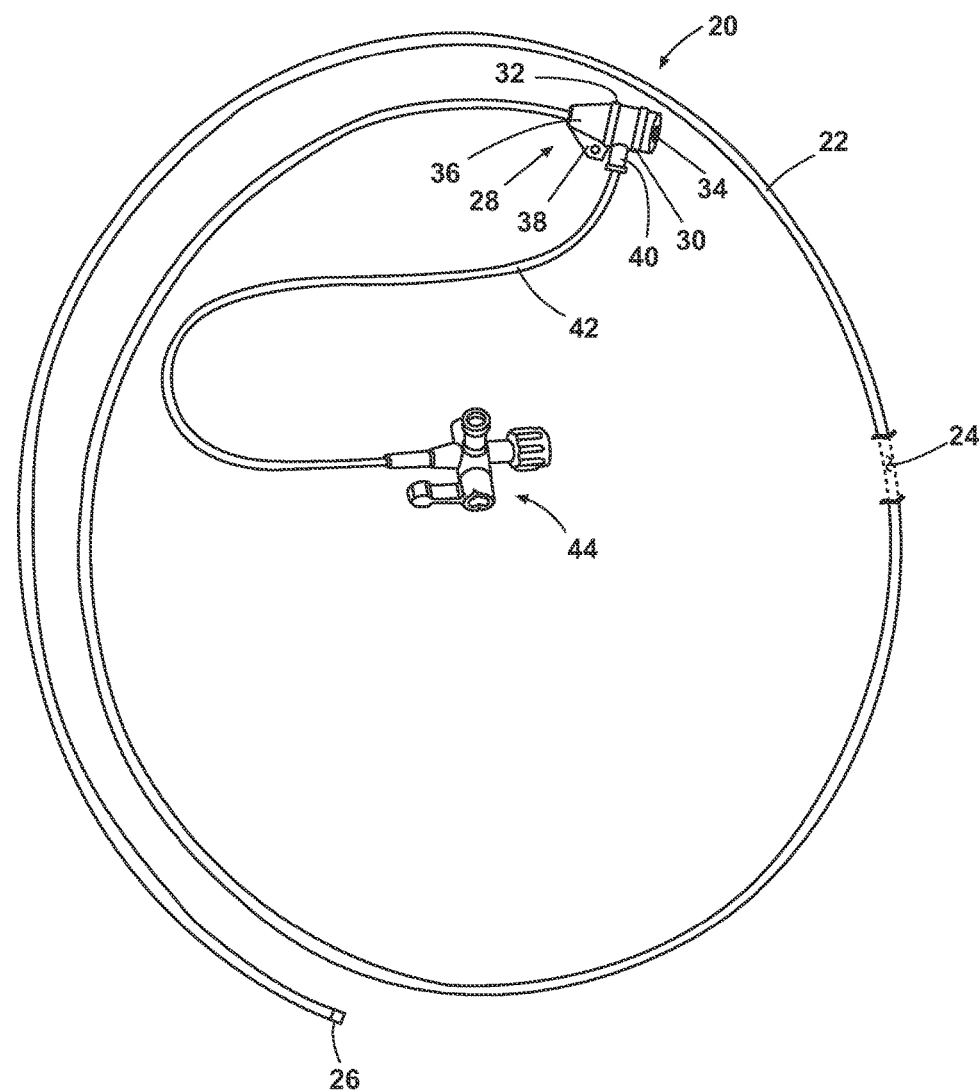
FIG. 3 is a perspective view of an exemplary introducer sheath according to one embodiment for facilitating introduction of the implant of FIG. 2 into a hollow anatomical structure.

FIG. 3 illustrates an exemplary embodiment of an introducer sheath 20 that can be used to facilitate introduction of an implant, such as the implant 10 in FIG. 2 or other suitable implant, into a HAS. The introducer sheath 20 can be any suitable device configured for insertion into the HAS and for introduction of the implant 10 into the HAS; many varieties of introducer sheaths are commercially available and known to one skilled in the art. On example of an introducer sheath 20 is disclosed in U.S. Pat. No. 5,897,497, issued Apr. 27, 1999, and entitled "Guiding Catheter Introducer Assembly." The depicted introducer sheath 20 in FIG. 3 is provided for illustrative purposes and is not intended to limit the present disclosure in any manner.

The illustrated introducer sheath 20 has a tubular and flexible shaft 22 with a lumen 24 and, at its distal end, a protective distal tip portion 26. The sheath 20 further includes a hub 28 attached to a proximal end of the shaft 22 and having a pair of annular shoulders, a proximal shoulder 30 and a distal shoulder 32. The hub 28 also comprises a proximal opening 34 generally aligned with and in communication with the lumen 24 at the proximal end of the shaft 22, a distal rotatable frustoconical sleeve 36 that includes the distal shoulder 32 and a radially extending anchoring flange 38, and a side port 40 extending radially from the hub 28 between the shoulders 30, 32. A sidearm 42 connected to the side port 40 of the hub 28 terminates at a fluid fitting 44 to facilitate introduction of fluids through the sidearm 42 and into the side port 40. In the depicted embodiment, the hub 28 is configured for fluid communication between the side port 40 and the shaft 22 such that a fluid introduced into the fluid fitting 44 can flow into the lumen 24 of the shaft 22. The sheath 20 can be sized for insertion into a HAS; as an example, the shaft 22 of the sheath 20 can have an outer diameter of about 1-5 mm. Another example of the introducer sheath 20 is an 8F sheath having a length of about 55 cm.

Figure 4:
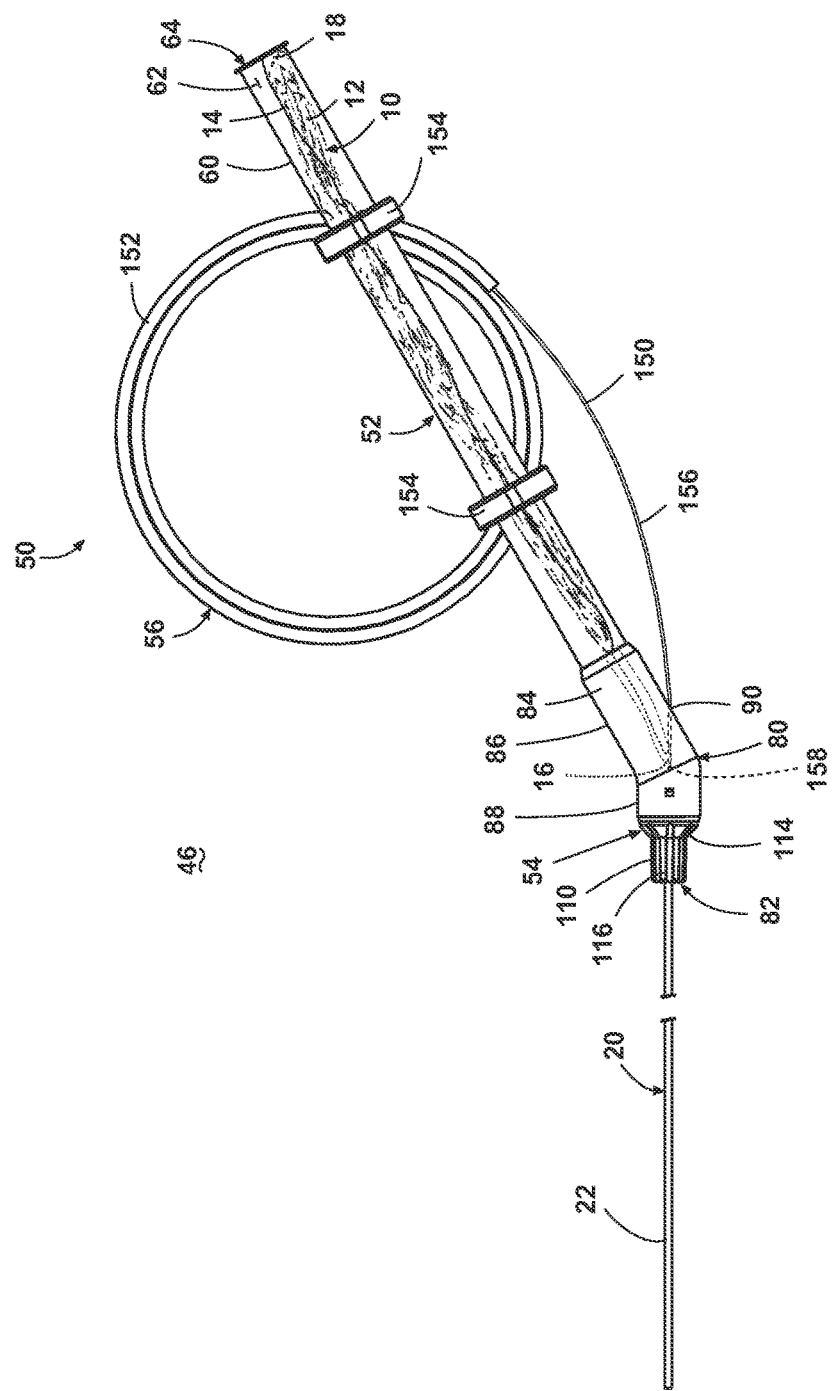
FIG. 4 is an elevation view of a system according to one embodiment comprising the introducer sheath of FIG. 3 and an embodiment of an apparatus for storage and/or introduction of the implant of FIG. 2.
Figure 5:
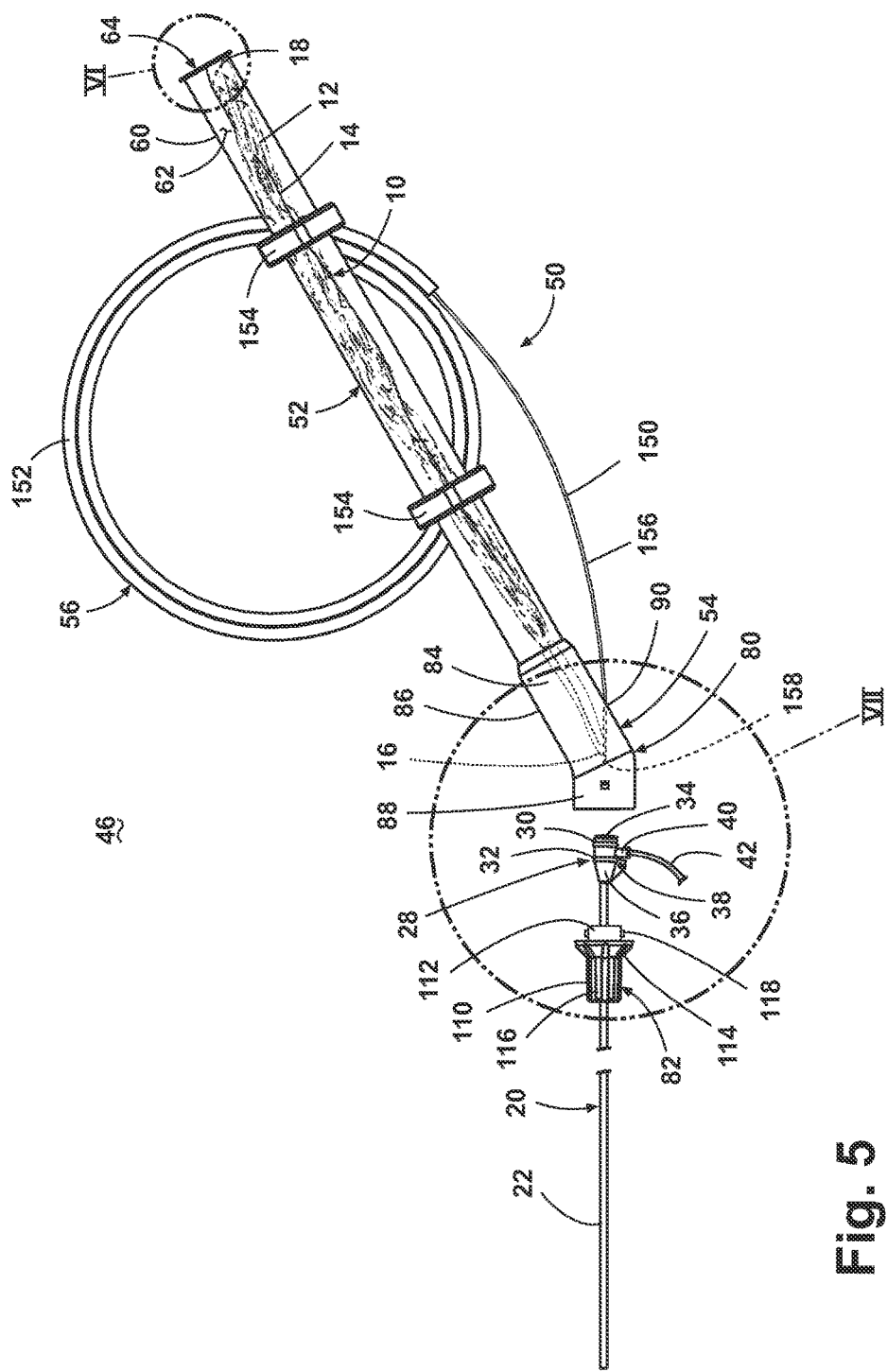
FIG. 5 is an elevation view identical to FIG. 4 with the introducer sheath and an embodiment of a coupler assembly of the apparatus comprising proximal and distal couplers shown as exploded.

Referring now to FIG. 4, the introducer sheath 20 can be included in a system 46 with the implant 10 of FIG. 2, or other suitable implant, and an apparatus 50 configured for storing and/or surgically introducing the implant 10 into a HAS. The depicted apparatus 50 comprises an implant storage unit 52 adapted to store the implant 10 prior to and during introduction of the implant 10 into the HAS, a coupler assembly 54 configured to couple the apparatus 50 to the introducer sheath 20, and an introducer assembly 56 that, when manipulated by the practitioner manually or through the operation of a motorized drive system, or through a manually operated gear train or other mechanism, feeds the implant from the implant storage unit 52, through the coupler assembly 54, and into the introducer sheath 20 for placement of the implant 10 in the HAS. In FIG. 5, the coupler assembly 54 of the apparatus 50 is illustrated as exploded to facilitate viewing the relative positioning of the introducer sheath 22 and the apparatus 50.

With continued reference to FIG. 5, the implant storage unit 52 of the depicted embodiment comprises a generally cylindrical tube 60 sized to accommodate the implant 10, as will be discussed in further detail below, and having a lumen 62 extending between the tube proximal and distal ends. An end cap 64 closes the proximal end of the tube 60, and the coupler assembly 54 receives the open distal end of the tube 60, as will be described in more detail below. The exemplary end cap 64 (see FIG. 6) has a closure wall 66 oriented generally perpendicular to the longitudinal axis of the tube 60, a generally cylindrical body 68 extending axially within the tube 60, and an annular flange 70 surrounding the closure wall 66 and abutting the proximal end of the tube 60. The tube 60 and corresponding end cap 64 can be generally cylindrical, as described above and shown in FIGS. 4 and 5, and other configurations are contemplated, including tubes and end caps having triangular, rectangular, and square cross-sectional shapes. The tube 60 and end cap 64 can have any suitable configuration and are not limited to the geometries described herein and illustrated in the figures.

Figure 6:
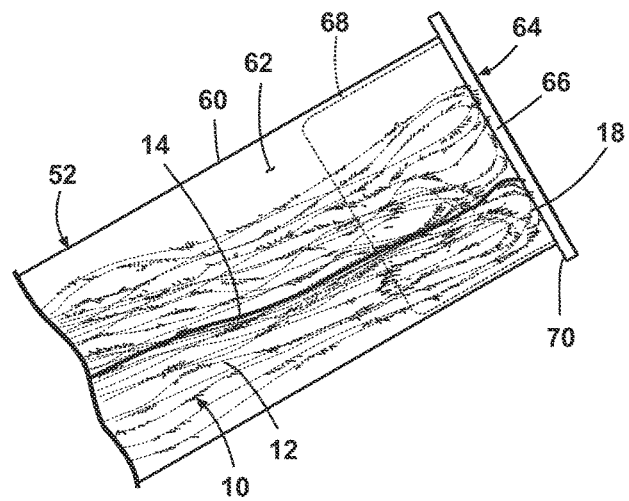
FIG. 6 is an enlarged view of the region labeled "VI" in FIG. 5.

As shown in FIG. 6, which is an enlarged view of the region labeled "VI" in FIG. 5, the end cap 64 can optionally function as an anchor for the implant 10 stored within the tube 60. Anchoring of the implant 10 inhibits bunching of the implant body 12 toward the distal end of the tube 60 and tangling of the tether 14. The end cap 64 can anchor the implant 10 in any desired manner, and, in the illustrated embodiment, the proximal end 18 of the implant body 12 and the proximal end of the tether 14 are positioned or sandwiched between the end cap body 68 and the side wall of the tube 60. The relative dimensions of the end cap body 68 and the tube 60 provide sufficient clearance for the body 12 and the tether 14 while applying a compressive force thereto to thereby retain the body 12 and the tether 14 at the proximal end of the tube 60. Optionally, a portion of the body 12 and/or the tether 14 can extend out the tube 60 between the flange 70 and the proximal end of the tube 60. Alternative methods of anchoring the implant 10 include, but are not limited to, employing an adhesive between the implant 10 and the end cap 64 and/or the tube 60. Further, the implant 10 can be anchored by the body 12, the tether 14, or both the body 12 and the tether 14.

Figure 7:
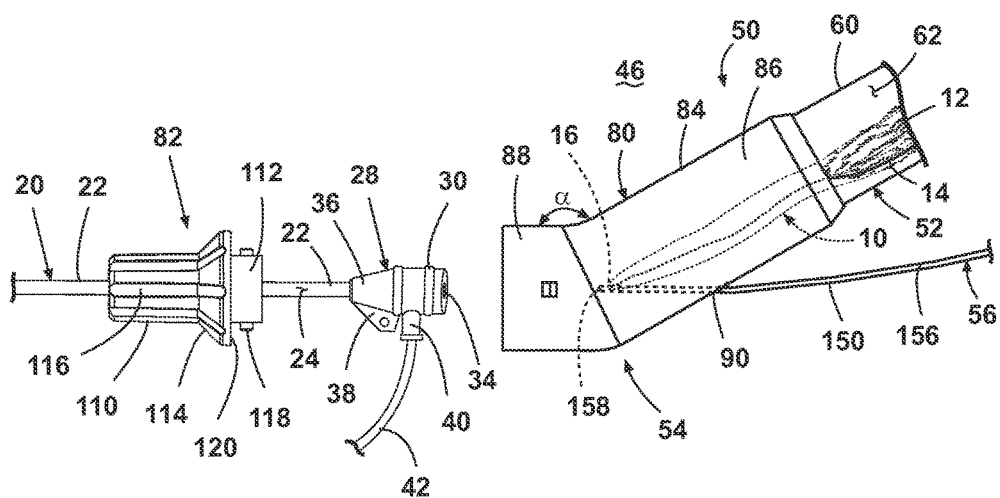
FIG. 7 is an enlarged view of the region labeled "VII" in FIG. 5.
Figure 8:
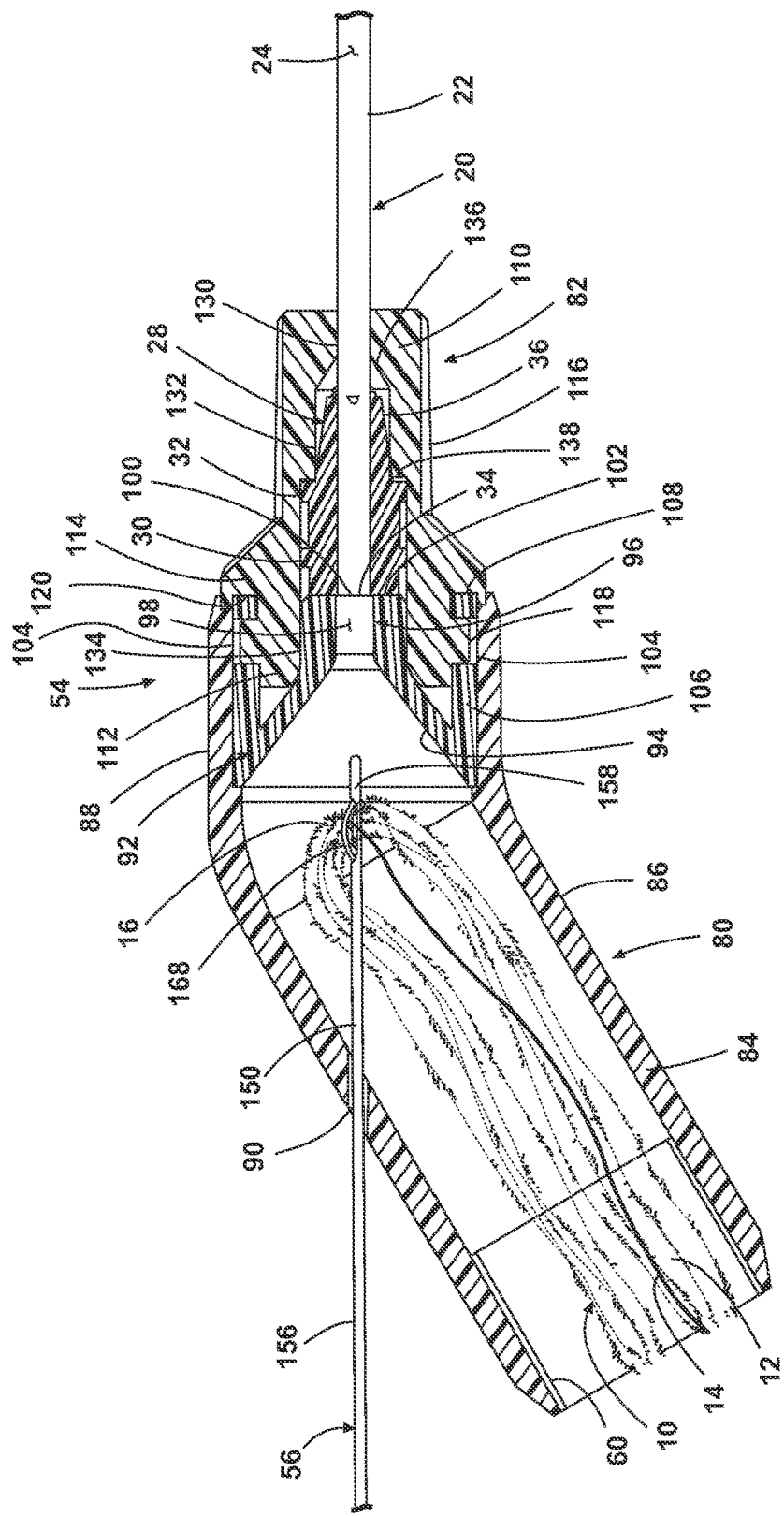
FIG. 8 is a sectional view of distal portions of the system of FIG. 4 with an introducer of the apparatus in a storage position according to one embodiment.

Referring now to FIGS. 7 and 8, which is an enlarged view of the region labeled "VII" in FIG. 5, the depicted coupler assembly 54 that couples the apparatus 50 to the introducer sheath 20 comprises mating proximal and distal couplers 80, 82. The proximal coupler 80 includes a tubular conduit 84 having a storage portion 86 and a coupling portion 88. In the depicted embodiment, the storage portion 86 and the coupling portion 88 are oriented at an obtuse angle α relative to each other. As an example, the angle α can be about 150 degrees; other examples of the angle α include 0-180 degrees. As best viewed in the sectional view of FIG. 8 and the perspective view of the same region in FIG. 9, the storage portion 86 aligns axially with the tube 60 and receives the distal end of the tube 60 to thereby connect the tube 60 and the storage portion 86 of the proximal coupler 80. The tube 60 and the proximal coupler 80 can be joined in any suitable fashion, such as, for example, an interference fit, with an adhesive, a snap fit, etc. An aperture 90 formed through a side wall of the storage portion 86 is aligned and can be generally collinear with the longitudinal axis of the coupling portion 88 and, when the system 46 is assembled, the proximal opening 30 of the hub 28 and the lumen 24 of the introducer sheath shaft 22.

Figure 9:
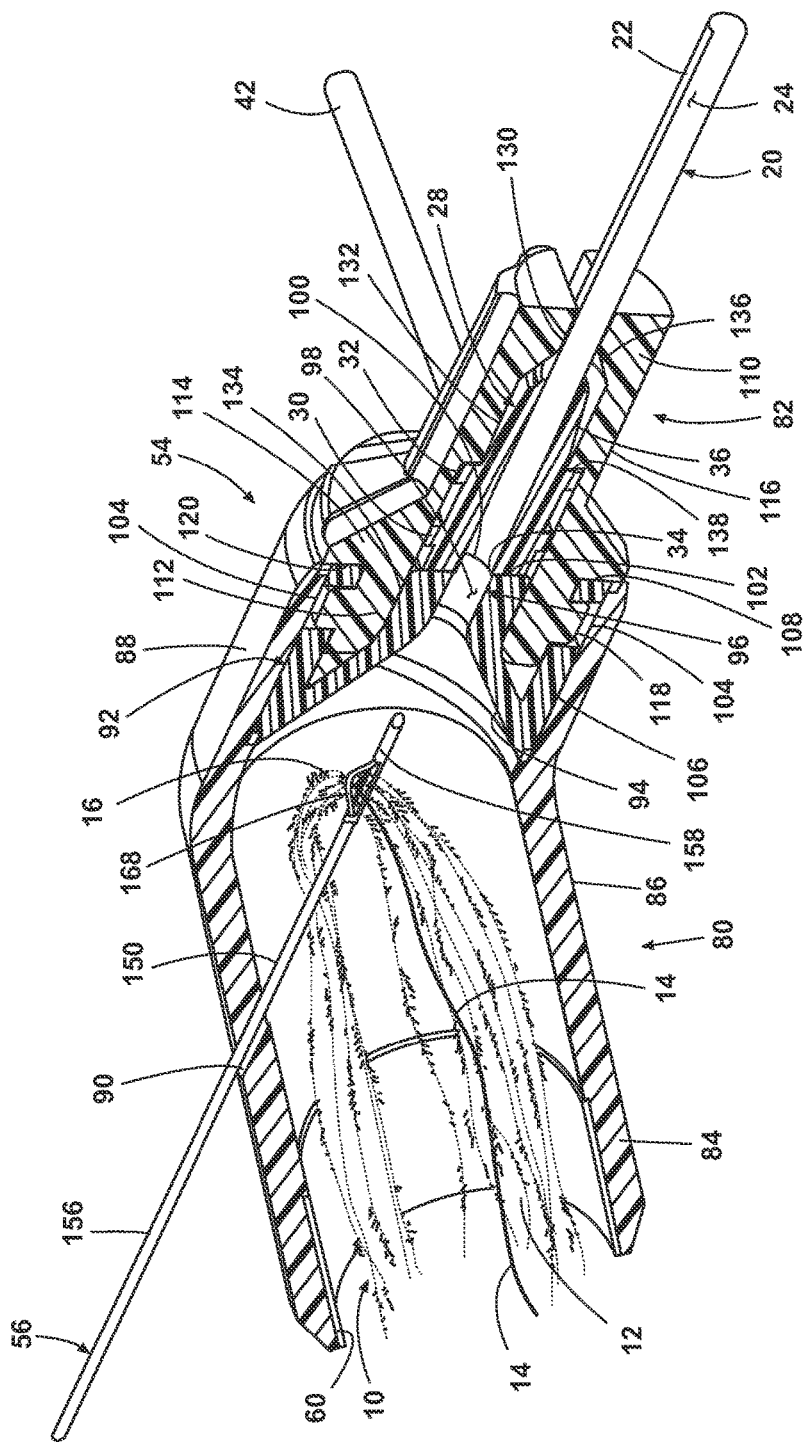
FIG. 9 is a perspective view of FIG. 8.

As shown in FIGS. 8 and 9, the coupling portion 88 houses an insert 92 having an introducer guide 94 in the form of a frustoconical wall that tapers distally and terminates at a duct 96 defining a channel 98 having an exit opening 100 surrounded by an annular distal face 102. The channel 98 and the exit opening 100 are oriented in axial alignment with the aperture 90 in the storage portion 86. The insert 92 further comprises a pair of opposing bayonet fitting keyways 104 formed in an outer wall 106 generally coaxial with the duct 96 and extending from the introducer guide 94 to a distal face 108 generally coplanar with the duct distal face 102. The insert 92 can be secured to the coupling portion 88 in any suitable fashion, such as, for example, an interference fit, with an adhesive, a snap fit, etc.; alternatively, the insert 92 or the features of the insert 92 can be integrally formed with the coupling portion 88.

While the proximal coupler 80 has been described as comprising the tubular conduit 84 having the storage portion 86 and the coupling portion 88 that houses the insert 92, the proximal coupler 80 can alternatively be considered as comprising only the insert 92, which performs a coupling function, with the tubular conduit 84, which performs a storage function, considered as an extension or part of the implant storage unit 52. Regardless, the exit opening 100 functions as an exit opening for the implant storage unit 52 and the overall apparatus 50 as the implant 10 exits the implant storage unit 52 and the apparatus 50 through the exit opening 100. The tubular conduit 84 and the insert 92 can be constructed in any desired manner with either or both parts functioning to partially store the implant 10 and/or couple the apparatus 50 to the introducer sheath 20.

Figure 10:
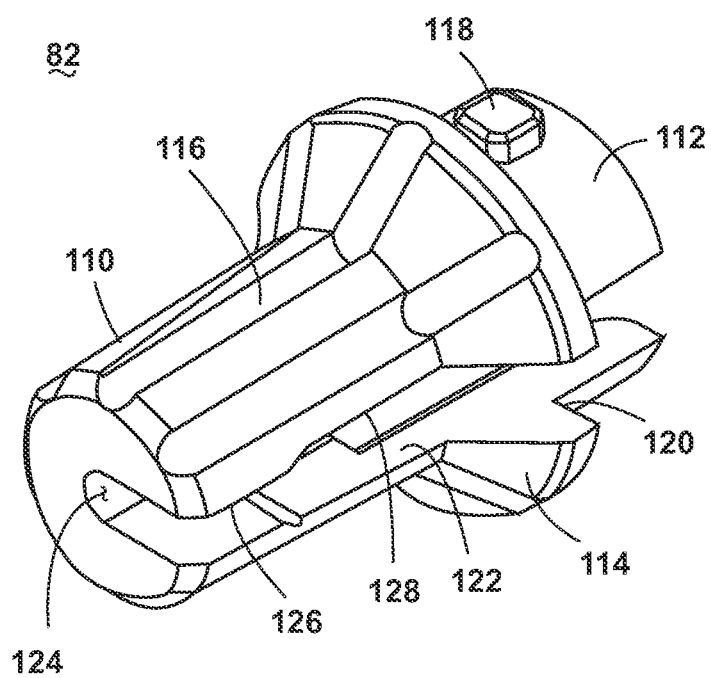
FIG. 10 is a perspective view of the distal coupler of the coupler assembly of FIG. 5.

Referring now to FIG. 10, the depicted embodiment of the coupler assembly distal coupler 82 comprises a distal generally cylindrical body 110, a proximal generally cylindrical body 112, and a distally tapering frustoconical flange 114 therebetween. The distal body 110 and the frustoconical flange 114 can optionally include a grip 116, such as a grip 116 in the form of a plurality of grooves, to facilitate manipulation of the distal coupler 82 by the practitioner. While the distal and proximal bodies 110, 112 can have any suitable relative dimensions, the distal body 110 of the illustrated embodiment is longer than and has a smaller cross-sectional diameter than the proximal body 112. The proximal body 112 is sized for insertion into and receipt by the proximal coupler 80 of the coupler assembly 54, particularly the insert 92 of the proximal coupler 80, and includes a pair of opposing keys 118 configured for receipt and sliding movement in the bayonet fitting keyways 104 of the insert 92 (see FIGS. 8 and 9 for relationship between the proximal body 112 and the insert 92). The proximal body 112 and the frustoconical flange 114 meet at a proximally-facing annular surface 120.

With continued reference to FIG. 10, the distal coupler 80 includes an elongated slot 122 extending the entire length of the distal coupler 80 and providing access to a central bore 124. The slot 122 comprises a first portion 126 sized at least for receipt of the shaft 22 of the introducer sheath 20 and a second portion 128 sized at least for receipt of the side port 40 of the introducer sheath 20. In the illustrated embodiment, the first and second portions 126, 128 are sized to receive the shaft 22 and the side port 40 such that the shaft 22 and the side port 40 have limited lateral movement within the slot 122. Referring back to FIGS. 8 and 9, the bore 124 has three coaxial sections, first, second, and third sections 130, 132, 134, that increase proximally in cross-sectional area relative to each other. The first section 130 is sized for receipt of the shaft 22 of the introducer sheath 20, the second section 132 is sized for receipt of the sleeve 36 on the hub 28 of the introducer sheath 20, and the third section 134 is sized for receipt of the remaining portion of the hub 28 and of the duct 96 of the proximal coupler 80. The first and second sections 130, 132 join at a frustoconical wall 136; the frustoconical wall 136 and the first section 130 are coincident with the first portion 126 of the slot 122. The second and third sections 132, 134 meet at a proximally-facing stop 138.

The proximal and distal couplers 80, 82 of the coupler assembly 54 can be connected together, as shown in FIGS. 8 and 9, to couple the apparatus 50 to the introducer sheath 20. In the coupled condition, the proximal and distal couplers 80, 82 retain the hub 28 of the introducer sheath 20 therebetween. In particular, the proximal end of the hub 28 abuts the duct distal face 102 of the proximal coupler 80, and the distal shoulder 32 of the hub 28 abuts the stop 138 of the distal coupler 82. Consequently, the aperture 90 and the channel 98 defined by the duct 96 of the proximal coupler 80 align axially with the proximal opening 34 of the hub 28 and, thereby, the lumen 24 at the proximal end of the shaft 22. The slot 122 of the distal coupler 82 accommodates the radially extending components of the hub 28, particularly the retaining flange 38 and the side port 40, which is connected to the sidearm 44 seen in FIG. 9. To retain the coupler assembly 54 in the coupled condition, the proximal coupler keyways 104 receive the distal coupler keys 118 in a known bayonet fitting fashion, and the proximally-facing annular surface 120 between the proximal body 112 and the frustoconical flange 114 of the distal coupler 82 abuts the distal face 108 of the proximal coupler 80.

Referring back to FIG. 4, the depicted embodiment of the introducer assembly 56 of the apparatus 50 comprises an introducer or pushrod 150 partially stored within a tubular casing 152 mounted to the tube 60 of the implant storage unit 52 via brackets 154. The brackets 154 can be mounted to an exterior wall of the tube 60; alternatively, the brackets 154 can join adjacent segments that form the tube 60, whereby the brackets 154 can themselves form part of the tube 60. The length of the casing 152 is sufficient to encase the proximal end of the pushrod 150 prior to use of the apparatus 50 for delivery of the implant 10. Further, the casing 152 can be coiled one or more times to accommodate the length of the pushrod 150 and, thereby, maintain a relatively compact configuration for the assembly 50. The pushrod 150 projects from the distal end of the casing 152 and into the aperture 90 of the proximal coupler 80. An exposed portion 156 of the pushrod 150 between the distal end of the casing 152 and the aperture 90 provides a gripping area for the practitioner to grasp and manipulate the pushrod 150. Alternatively, the exposed portion 156 can be gripped or engaged by a motorized drive system (not shown) or a non-motorized gear train or other mechanism operated by the practitioner to manipulate the pushrod 150. Using such a motorized drive system, etc. may advantageously provide for single-handed operation of the apparatus 50 by the practitioner.

Figure 11:
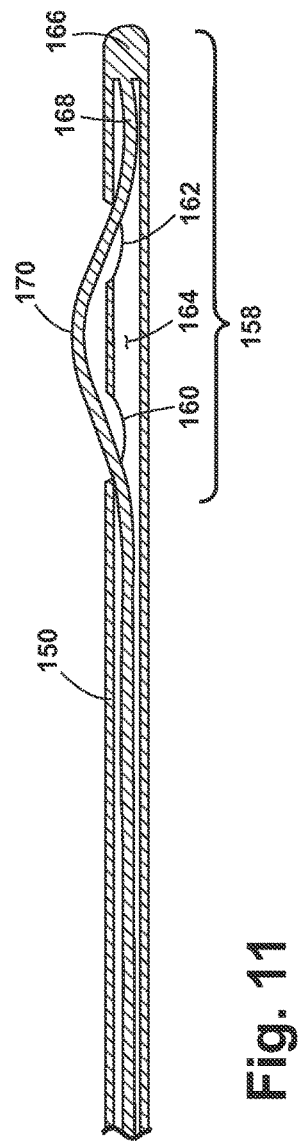
FIG. 11 is an enlarged sectional view of an embodiment of the introducer, particularly the proximal end of the introducer, of the apparatus of FIG. 4.

As shown in FIGS. 8 and 9, the pushrod 150 extends through the aperture 90 and into the tubular conduit 84, where it terminates at a distal tip region 158, which is shown in an enlarged sectional view of the proximal and distal ends of the pushrod 150 in FIG. 11 (implant 10 not shown for clarity). As seen in this figure, the distal tip region 158 of the pushrod 150 includes spaced openings 160, 162 providing access to an internal lumen 164 that terminates at a distal plug 166. A wire 168 resides within the lumen 164 except for an implant retaining portion 170 located externally of the lumen 164 between the openings 160, 162. The wire 168 exits and enters the lumen 164 through the openings 160, 162 to form the implant retaining portion 170. The wire 168 can be coupled to the pushrod 150 at or near the distal ends thereof by any suitable means, such as welding, adhesives, crimping of the pushrod 150 onto the wire tip, a friction fit, interference fit, etc. Alternatively, the distal portion of the wire 168 can be located in but not connected to the distal portion of the pushrod 150.

Figure 12:
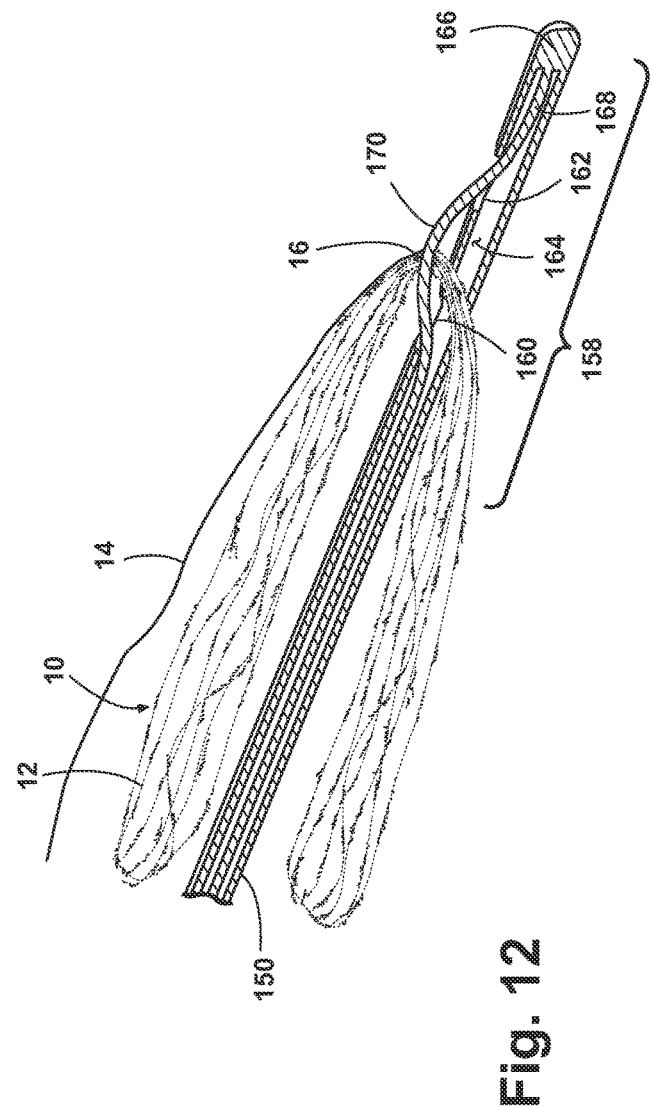
FIG. 12 is a sectional perspective view of the distal end of the introducer (in section) from FIG. 11 and the implant of FIG. 2 according to one embodiment.

With reference to FIG. 12, which illustrates the distal end of the pushrod 150 and the implant 10, the implant retaining portion 170 attaches the implant 10 to the pushrod 150 for cooperative movement during advancement of the pushrod 150. In the illustrated embodiment, the implant 10 attaches to the implant retaining portion 170 at the distal end 16 of the body 12 at or near where the tether 14 connects to the body 12. In particular, the distal end 16 is held between the implant retaining portion 170 of the wire 168 and the portion of the pushrod 150 between the openings 160, 162. In this configuration, the tether 14 and about half of the length of the body 12 are located on one side of the wire 168 and the other half of the length of the body 12 are located on the opposite side of the wire 168. The body 12 wraps around the wire 168 such that the free ends of the body 12 are folded upon each other form the proximal end 18 of the body 12, as described above. The implant retaining portion 170 forms a closed noose or snare around the implant 10 that permits the implant 10 to be retained whether the pushrod 150 is pushed distally or pulled proximally. The implant retaining portion 170 can further be configured to hold the implant 10 against the portion of the pushrod 150 between the openings 160, 162 tightly enough to prevent shifting of the implant 10. The above-described attachment of the implant 10 and the pushrod 150 provides an exemplary manner of attachment; the implant 10 and the pushrod 150 can be joined in any suitable manner and are not limited to that described above and shown in the figures.

Referring again to FIG. 11, the distal end of the wire 168 is removably attached to the distal plug 166 such that the wire 168 separates from the distal plug 166, or other portion of the pushrod 150, upon application of a suitable proximal force to the wire 168. Continuation of the proximal force pulls the wire 168 through the openings 160, 162 such that the distal end of the wire 168 resides within the lumen 164 proximally of the openings 160, 162, thereby releasing the implant 10 (FIG. 12) from the wire 168 and the pushrod 150. Releasing the implant 10 from the pushrod 150 will be described in greater detail with respect to the description below of the operation of the system 46. The proximal force can be applied by, for example, the practitioner or a motorized drive system, non-motorized gear train or mechanism, etc. pulling on the wire 168, in which case, a proximal end of the wire 168 can project from the pushrod 150, such as through the proximal end of the pushrod 150, as shown in FIG. 11. The type and degree of attachment between the wire 168 and the pushrod 150 can be selected according to a desired proximal force required to effect separation of the wire 168 from the pushrod 150. As examples, the wire 168 can be attached to the pushrod 150 with an adhesive or by chemical joining processes, including various types of welding. Alternatively, the wire 168 can be integrally formed with the pushrod 150 and, optionally, scored, such as by a notch or incision, to facilitate the separation.

The pushrod 150 can be manipulated by the practitioner, manually or through the operation of a motorized or non-motorized drive system, between various positions for introducing the implant 10 into a HAS. FIGS. 8 and 9 illustrate a retracted or storage position of the pushrod 150; the storage position corresponds to a position of the pushrod 150 and, thereby, the implant 10 prior to use of the apparatus for introduction of the implant 10 into the HAS (i.e., during storage). In the exemplary storage position of FIGS. 8 and 9, the distal tip region 158 of the pushrod 150 resides in the proximal coupler 80, particularly at the bend between the storage portion 86 and the coupling portion 88 of the tubular conduit 84, and in axial alignment with the channel 98. As a result, the implant 10 extends from the pushrod 150, through the storage portion 86 of the tubular conduit 84, and through the tube 60 for storage in the storage portion 86 and the tube 60.

The components in which the implant 10 is stored, specifically the storage portion 86 and the tube 60 in the depicted embodiment, can be sized to accommodate the implant 10. In one embodiment, the storage portion 86 and the tube 60 have a collective length (i.e., the length of the storage portion 86 plus the length of the tube 60 less any overlap between the two components) corresponds to the length of the implant 10, that is, the distance between the distal and proximal ends 16, 18 of the body 12 of the implant 10. In such an embodiment, the body 12 of the implant 10 extends the collective length of the storage portion 86 and the tube 60 with no or minimal bunching or folding of the body 12. Alternatively, the collective length of the storage portion 86 and the tube 60 can be less than the length of the body 12 such that the body 12 undergoes some bunching or folding upon itself within the storage portion 86 and/or the tube 60. In yet another embodiment, the collective length of the storage portion 86 and the tube 60 can be greater than the length of the body 12. Further, as illustrated in the exemplary embodiment, the storage portion 86 and/or the tube 60 can each have an inner diameter sufficiently large to accommodate the implant 10 in its natural expanded condition. Alternatively, the storage portion 86 and/or the tube 60 can each have an inner diameter that effectively compresses the implant 10 from its expanded condition to a compressed condition, at any appropriate degree of compression.

FIGS. 8 and 9 illustrate an exemplary storage position; other storage positions are possible. In other exemplary storage positions, the distal tip region 158 of the pushrod 150 can be located proximally of that shown in FIGS. 8 and 9, such as between the aperture 90 and the position shown in FIGS. 8 and 9. Alternatively, the distal tip region 158 of the pushrod 150 can be located distally of that shown in FIGS. 8 and 9, such as between the position shown in FIGS. 8 and 9 and the exit opening 100 of proximal coupler 80. As another alternative, the pushrod 150 can project beyond the exit opening 100 with the implant 10 residing within the proximal coupler 80 and the tube 60.

Figure 13:
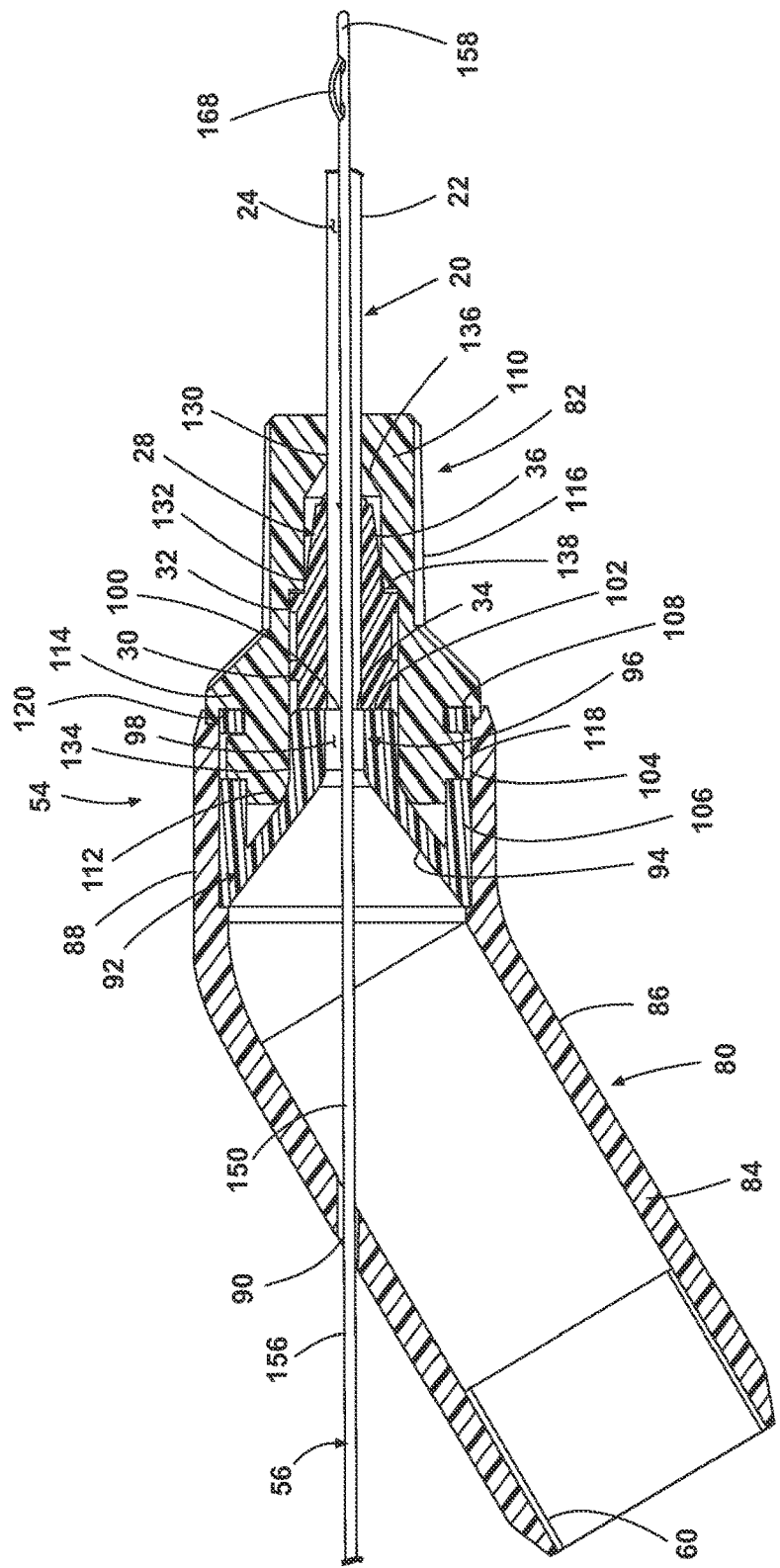
FIG. 13 is a sectional view similar to FIG. 8 with the introducer of the apparatus of FIG. 4 in an advancing position according to one embodiment; the implant is not shown for clarity.
Figure 14:
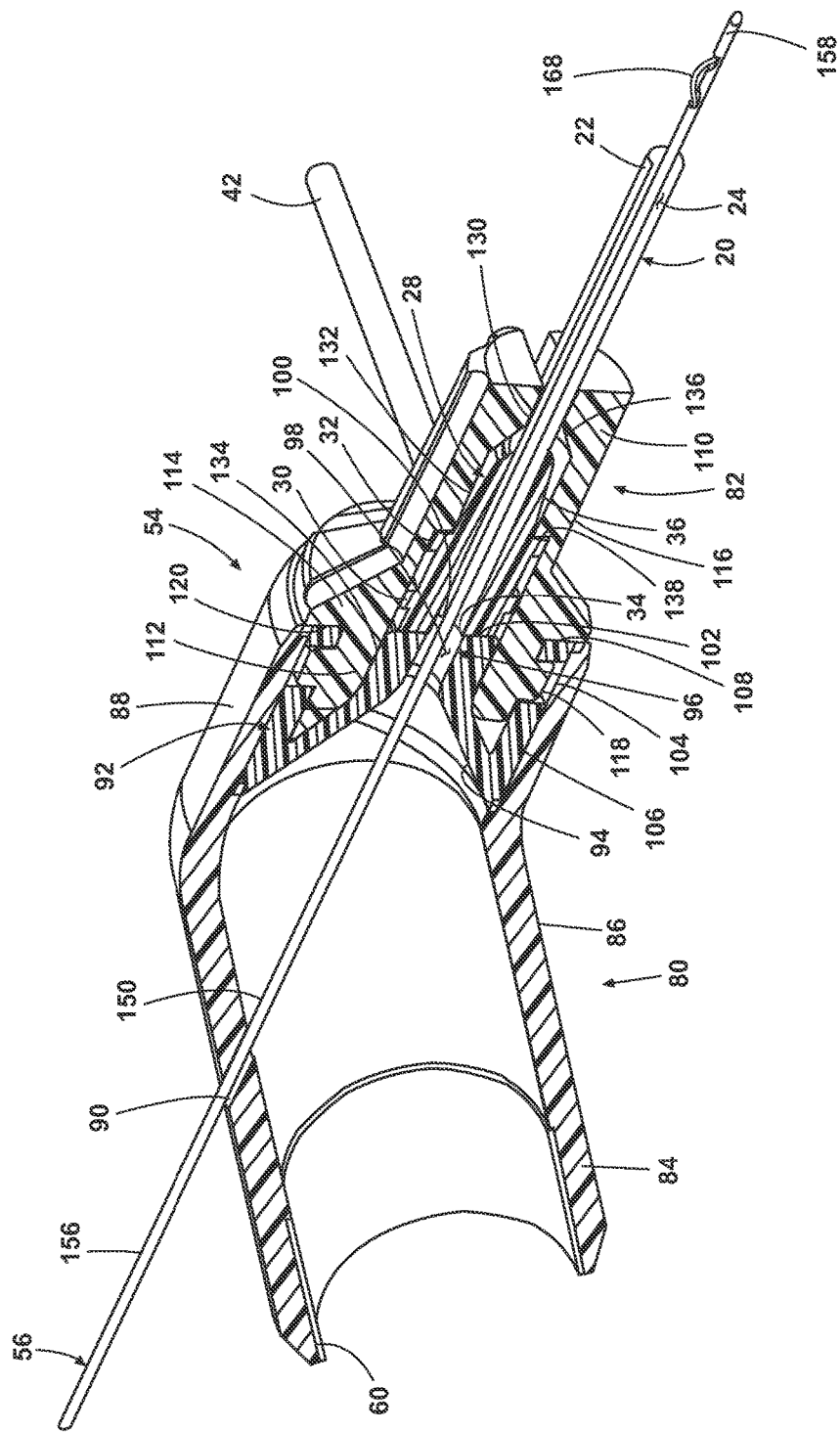
FIG. 14 is a perspective view of FIG. 13; the implant is not shown for clarity.

FIGS. 13 and 14 illustrate an advancing position of the pushrod 150; the advancing position corresponds to a position of the pushrod 150 and, thereby, the implant 10 during use of the apparatus for introduction of the implant 10 into the HAS. In the advancing position, the distal tip region 158 of the pushrod 150 is located distally of its location when in the storage position; therefore, any distal movement of the pushrod 150 from the storage position corresponds to moving the pushrod 150 to the advancing position. FIGS. 13 and 14 illustrate an exemplary advancing position with the implant 10 not shown for clarity. When moving the pushrod 150 from the storage position to the advancing position, the distal tip region 158 of the pushrod 150 advances through the channel 98 and exit opening 100 of the proximal coupler 80 and into the introducer sheath 20, particularly into the hub proximal opening 34, through the hub 28, including the collar 36, and into the shaft lumen 24 of the introducer sheath 20, which is held by the distal coupler 82. As the pushrod 150 so advances, the implant 10 is compressed radially and elongated as it is forced through the tapering introducer guide 94 and into the lumen 24 of the introducer sheath 20. Thus, when advancing, the pushrod 150 and the implant 10 have a common travel direction leaving the apparatus 50 through the exit opening 100 and entering the introducer sheath 20 through the proximal opening 34; in the illustrated embodiment, the travel direction is substantially linear, but other forms of travel direction are possible depending on the configuration of the apparatus 50. Other positions of the pushrod 150 will be described below in conjunction with the description of methods of use of the system 46.

Embodiments of methods of use of the system 46 are described below. While the system 46 can be employed in conjunction with any suitable HAS, the methods are described with respect to the greater saphenous vein B for illustrative purposes. It will be understood that the methods can be modified or adapted as necessary, if necessary, for use in other HASs. The methods can also be modified or adapted as necessary, if necessary, for use with embodiments of the system 46 other than the embodiment employed in the following description. In the description of the methods, the various steps are discussed in terms of being performed by the practitioner; however, it is understood that these steps may be performed by the practitioner manually or through the operation of a motorized or non-motorized drive system.

Figure 15:
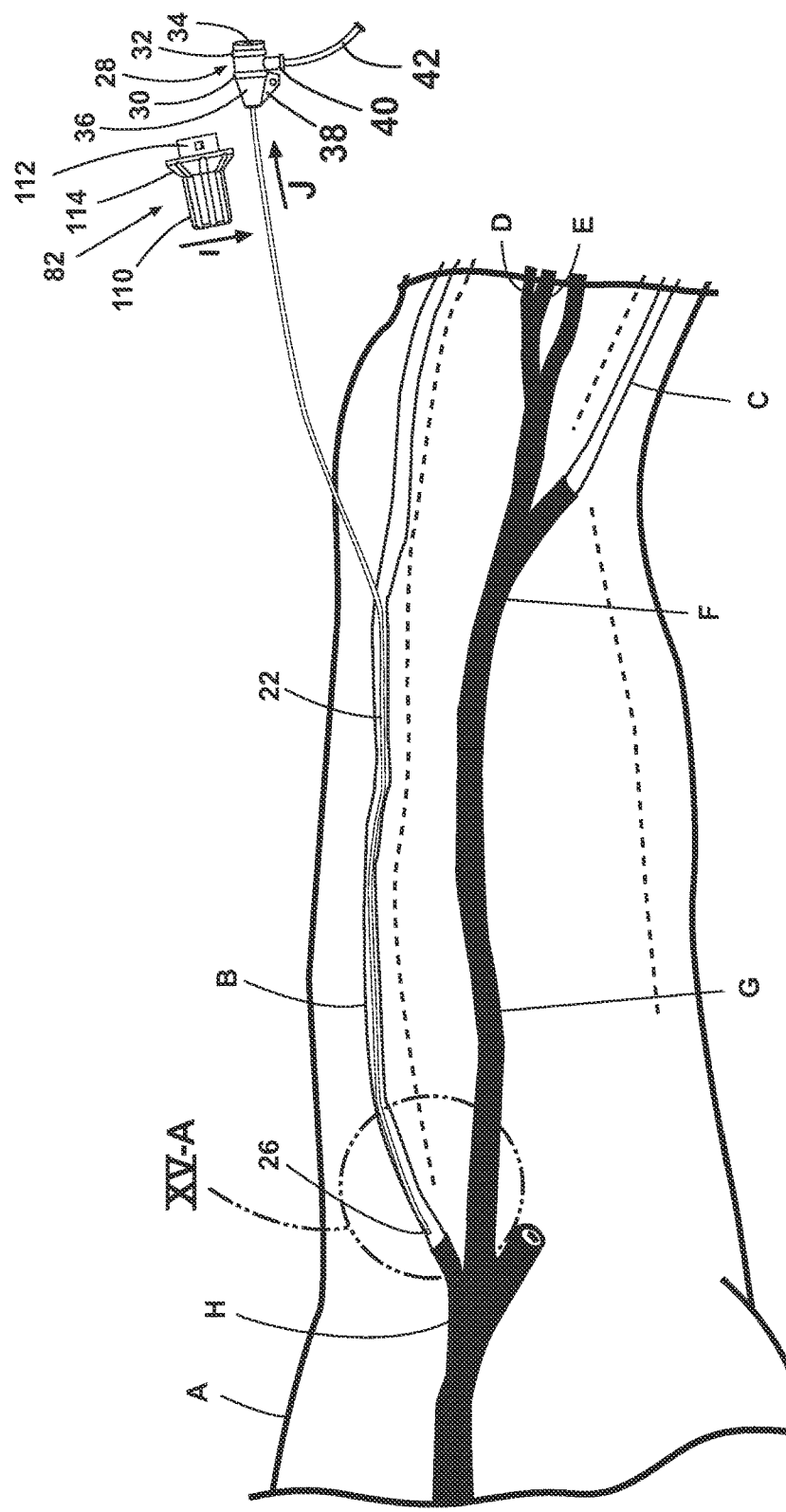
FIGS. 15-24A illustrate various exemplary stages of a method of use of the system according to one embodiment.
Figure 15A:
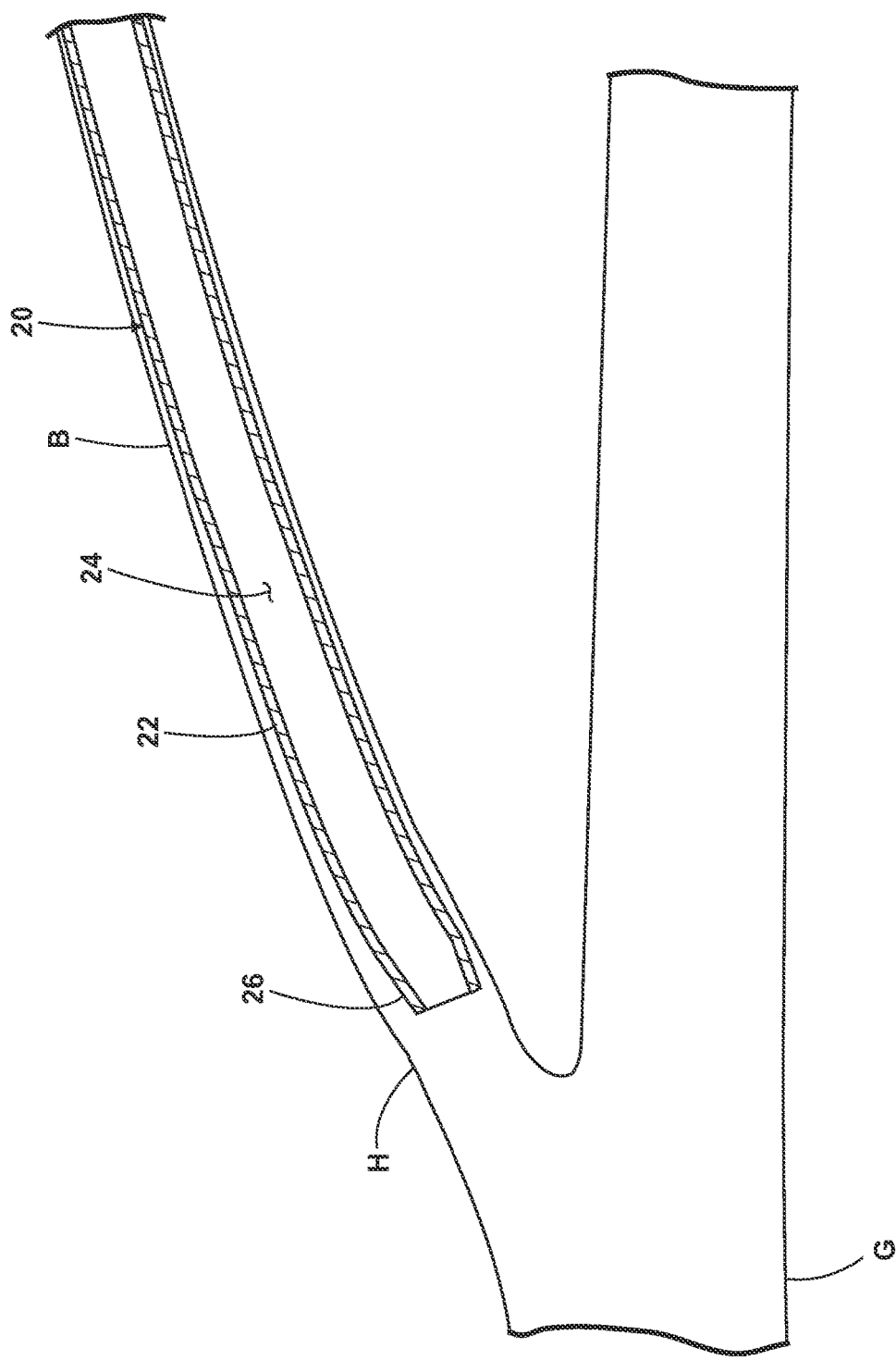
FIG. 15A is an enlarged view of the region labeled "XV-A" in FIG. 15.

In one embodiment of a method of use of the system 46, various stages of which are depicted in FIGS. 15-24A, the target HAS (e.g., a vein such as the greater saphenous vein B) can first be accessed at an access site through the skin by using a suitable access technique (e.g., the Seldinger technique). A guidewire is passed into the vein B, and the introducer sheath 20 is fed over the guidewire into the vein B and advanced to the desired implant location. In the case of the greater saphenous vein B, the desired implant location is just below the sapheno-femoral junction H. The guidewire is then withdrawn from the introducer sheath 20, thereby leaving the shaft 22 or a portion thereof in the vein B. The position of the introducer sheath 20 relative to the vein B and the sapheno-femoral junction H can be verified using appropriate techniques, such as ultrasound imaging. FIG. 15 illustrates the leg A with the shaft 22 of the introducer sheath 20 located in the greater saphenous vein B and the hub 28 positioned externally of the leg A. FIG. 15A provides an enlarged view of the region labeled "XV-A" in FIG. 15 to show the location of the distal tip portion 26 in the saphenous vein B and relative to the sapheno-femoral junction H.

Figure 16:
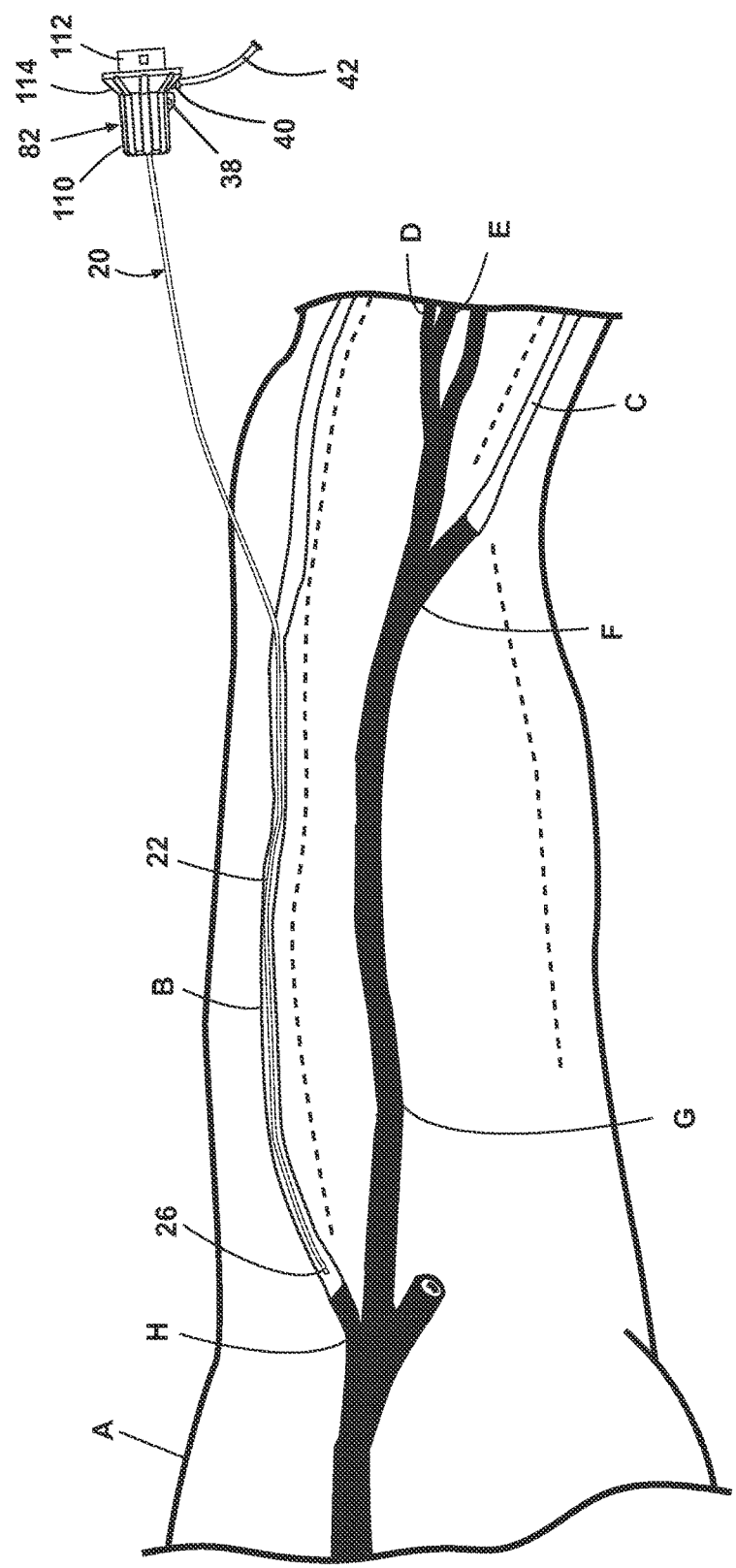

After advancement of the introducer sheath 20 to the desired implant location, the apparatus 50 is coupled to the introducer sheath 20. To this end, the distal coupler 82 is mounted to the introducer sheath 20, followed by coupling the proximal and distal couplers 80, 82. In particular, the distal coupler 82 is placed onto the shaft 22 distally of the hub 28, as indicated by the arrow I in FIG. 15, by inserting the shaft 22 through the slot 122 and into the bore 124, and the distal coupler 82 is then slid proximally along the shaft 22, as indicated by the arrow J in FIG. 15, and onto the hub 28 with the flange 38 and the side port 40 extending through the slot 122. FIG. 16 illustrates the introducer sheath 20 with the distal coupler 82 mounted to the hub 28 and the proximal end of the shaft 22. Alternatively, the distal coupler 82 and the introducer sheath 20 can be coupled together prior to insertion of the introducer sheath 20 into the vein B, whereby the distal coupler 82 can be placed onto the introducer sheath 20 through the slot 122 in the manner described above, or, in another embodiment, the shaft 22 of the introducer sheath 20 can be inserted directly and axially into the bore 124 at the proximal end of the bore 124 rather than radial insertion through the slot 122.

Figure 17:
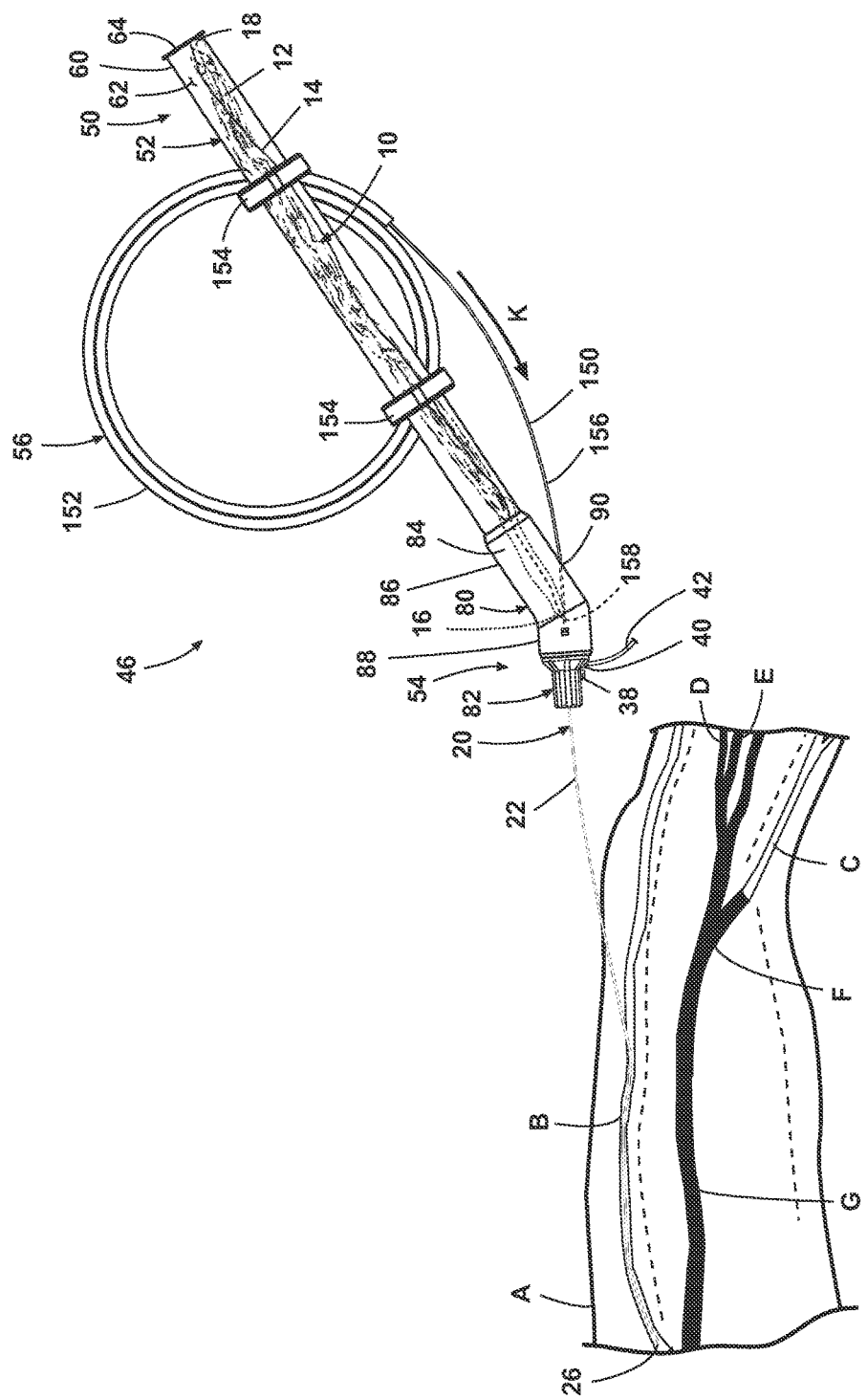

After the distal coupler 82 is mounted to the introducer sheath 20, the proximal coupler 80 and, thereby, the remainder of the apparatus 50, is attached to the distal coupler 82. Particularly, the keys 118 of the distal coupler 82 are inserted into the keyways 104 of the proximal coupler 80, and the proximal and/or distal couplers 80, 82 are manipulated as needed (e.g., rotated or twisted) to construct the bayonet fitting. FIG. 17 illustrates the introducer sheath 20 with the apparatus 50 mounted thereto. Details of the proximal and distal couplers 80, 82 and the introducer sheath 20 in the coupled configuration are described above and shown in FIGS. 8 and 9. Notably, the proximal coupler exit opening 100 and the introducer sheath proximal opening 34 are aligned with each other to enable advancement of the pushrod 150 from the apparatus 50, through both openings 100, 34, and into the introducer sheath 20, as will be described in more detail below. In the depicted embodiment, the proximal coupler exit opening 100 and the introducer sheath proximal opening 34 are directly adjacent one another to effect the alignment, and other methods of aligning the openings 100, 34 are possible.

With the apparatus 50 coupled to the introducer sheath 20, as illustrated in FIG. 17, the apparatus 50 can be easily handled and manipulated by the practitioner due to various aspects of the apparatus 50. One exemplary contributing aspect is the obtuse angle $\alpha$. Because of the obtuse angle $\alpha$, the portion of the apparatus 50 located proximally of the angle vertex, i.e., in the depicted embodiment, the storage portion 86 of the proximal coupler 80, the implant storage unit 52, and the introducer assembly 56, hereinafter referred to as the system proximal portion, is angled relative to the introducer sheath 20 and the portion of the apparatus 50 located distally of the angle vertex, i.e., in the depicted embodiment, the coupling portion 88 of the proximal coupler 80 and the distal coupler 82, hereinafter referred to as the system distal portion, when the apparatus 50 is coupled to the introducer sheath 20. The system proximal portion, depending on the manner in which the practitioner holds the apparatus 50, can be angled upward, downward, laterally, or a combination of laterally and upward or laterally and downward relative to the system distal portion. As a result, the portion of the apparatus 50 for storing the implant 10, which defines a storage axis, is offset, particularly, angularly offset, from the location where the implant 10 enters the introducer sheath 20 and the vein B, or the travel direction of the pushrod 150 and the implant 10. This geometry facilitates ease of use of the apparatus 50 because the practitioner can orient the system proximal portion as desired (i.e., upward, downward, laterally, or combination thereof) to allow the practitioner to comfortably hold the apparatus 50 while locating the gripping area or exposed portion 156 of the pushrod 150 as desired for optimal manual manipulation of the pushrod 150.

When the apparatus 50 is oriented as desired, the practitioner can optionally remove the end cap 64 from the tube 60 such that the implant 10 is no longer anchored at the proximal end of the tube 60; the apparatus 50 in this state is ready for introduction of the implant 10 into the vein B. The practitioner grasps the exposed portion 156 of the pushrod 150 and moves the pushrod 150 distally from the storage position (see FIGS. 8 and 9) to and distal of the advancing position (see FIGS. 13 and 14) by applying a proximal force to the pushrod 150, as illustrated by the arrow K in FIG. 17, thereby advancing the pushrod 150 and the implant 10 through the coupler assembly 54. In particular, as depicted in FIGS. 13 and 14, the pushrod 150 and the implant 10 (not shown for clarity) move distally through the channel 98 and the exit orifice 100 of the proximal coupler 80 to enter the introducer sheath 20 at the proximal opening 34. The introducer guide 94 directs the pushrod 150 toward the channel 98 if the pushrod 150 diverges from axial alignment with the channel 98 prior to entering the channel 98. After entering the proximal opening 34, the pushrod 150 and the implant 10 continue their advancement through the hub 28 and into the lumen 24 of the shaft 22.

As the pushrod 150 advances the implant 10 through the proximal coupler 80, the body 12 of the implant 10 converts from its expanded condition to a compressed condition as a result of the relatively small cross-sectional diameter of the channel 98 and exit opening 100; the channel 98 effectively forces the implant body 12 to compress in order to pass therethrough. The introducer guide 94 also facilitates the compression of the implant body 12 as it approaches the channel 98 by gradually reducing the cross-sectional diameter of the implant body 12. Lengthening of the implant body 12 can accompany the compression. Because the proximal opening 34, the hub 28, and the shaft lumen 24 of the introducer sheath 20 preferably have a cross-sectional diameter about equal to that of the channel 98 and the exit opening 100, the implant body 12 retains substantially the same compressed condition as it moves through the introducer sheath 20.

Figure 18:
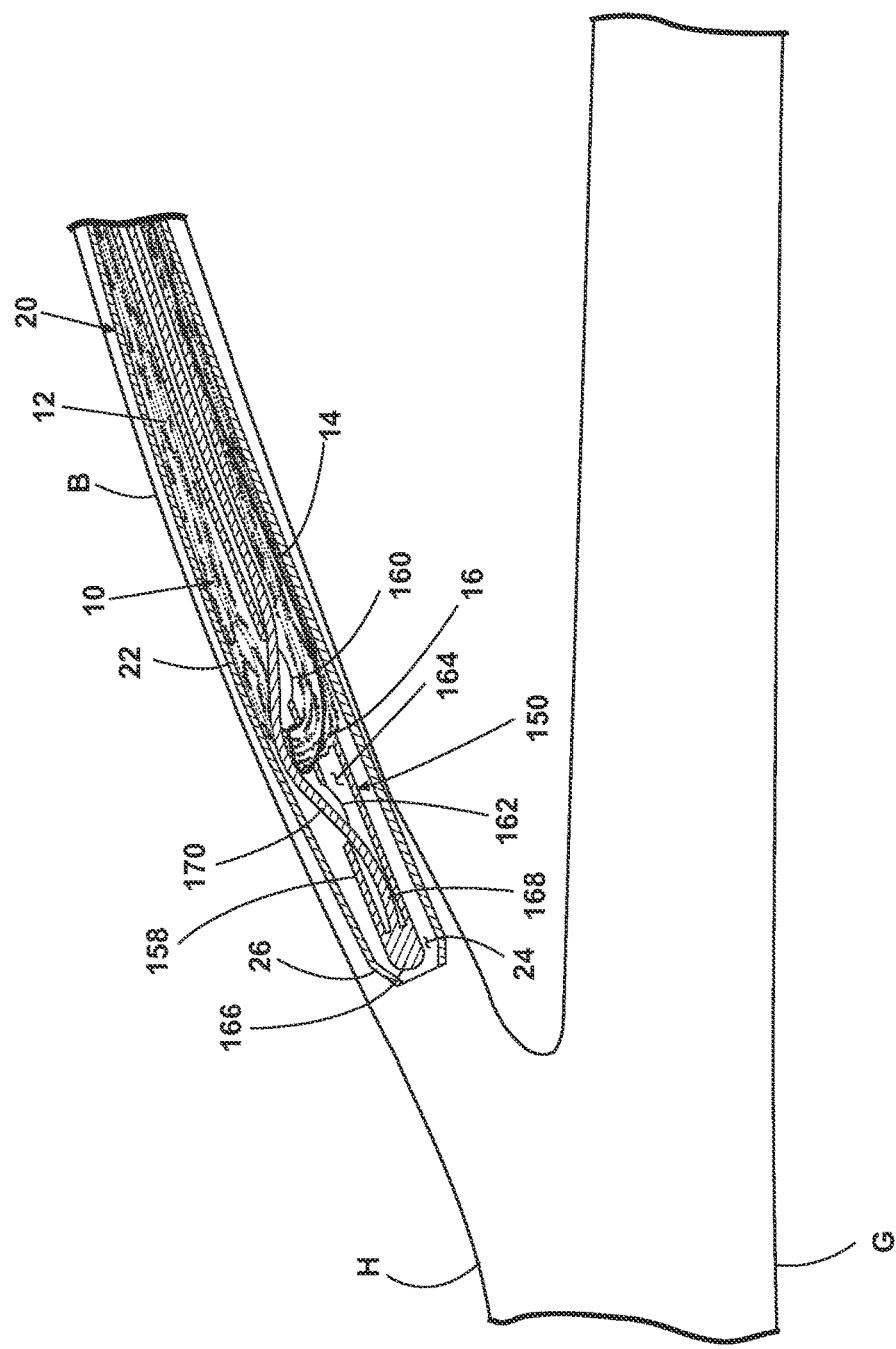

The pushrod 150 and the implant 10 cease advancement when reaching the desired implant location, which is just below the sapheno-femoral junction H in the present example. FIG. 18 illustrates the pushrod 150 and the implant 10 fully advanced into the greater saphenous vein B to just below the sapheno-femoral junction H. In one embodiment, the practitioner advances the pushrod 150 and the implant 10 until the distal end of the pushrod 150 is aligned with the distal tip portion 26 of the shaft 22 as observed under imaging guidance, such as ultrasound guidance. Depending on the resolution of the imaging equipment and other factors, the distal end of the pushrod 150 can be flush with the distal tip portion 26 of the shaft 22 (i.e., the pushrod end does not project beyond the shaft 22), or the distal end of the pushrod 150 can project beyond the shaft distal tip portion 26 when observed as being aligned. In another embodiment, the practitioner can advance the distal end of the pushrod 150 beyond the distal tip portion 26 of the shaft 22. With the pushrod 150 and the implant 10 fully advanced, the implant 10, including the tether 14, preferably extends along the entire length of the shaft lumen 24.

While the method of use of the system 46 is described in terms of advancement of the pushrod 150 and implant 10 to place the implant 10 at the desired implant location, some proximal retraction of the may also accompany the placement of the implant 10. Since the implant retaining portion 170 of the pushrod 150 forms a closed noose or snare around the implant 10, the pushrod 150 can be retracted proximally to withdraw the implant 10, which is a useful feature in case the pushrod 150 and implant 10 are advanced beyond the desired implant location. This feature can further be used to add additional bulk to the implant 10 once it is placed at the desired implant location, as described below.

Figure 19:
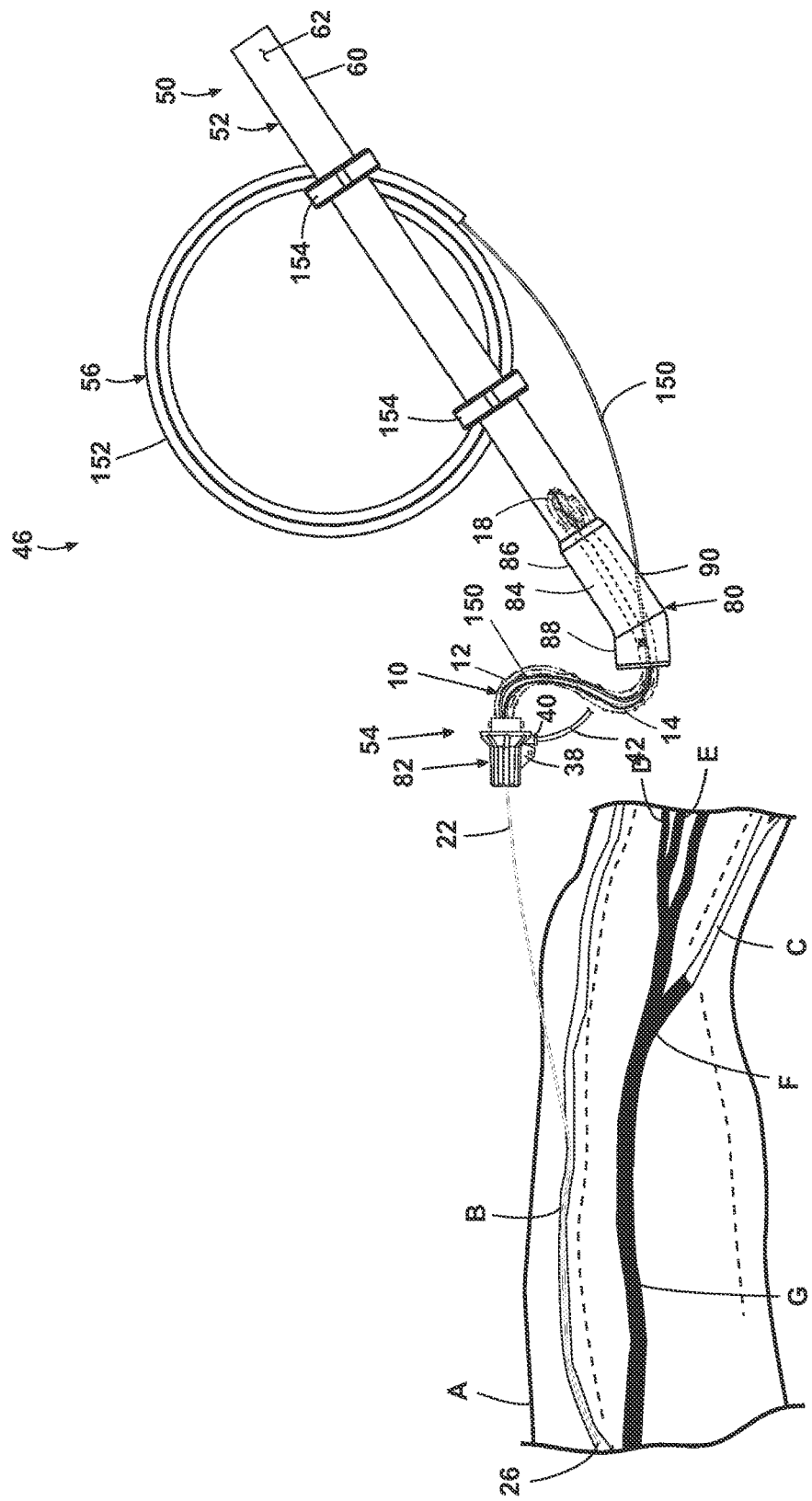
Figure 20:
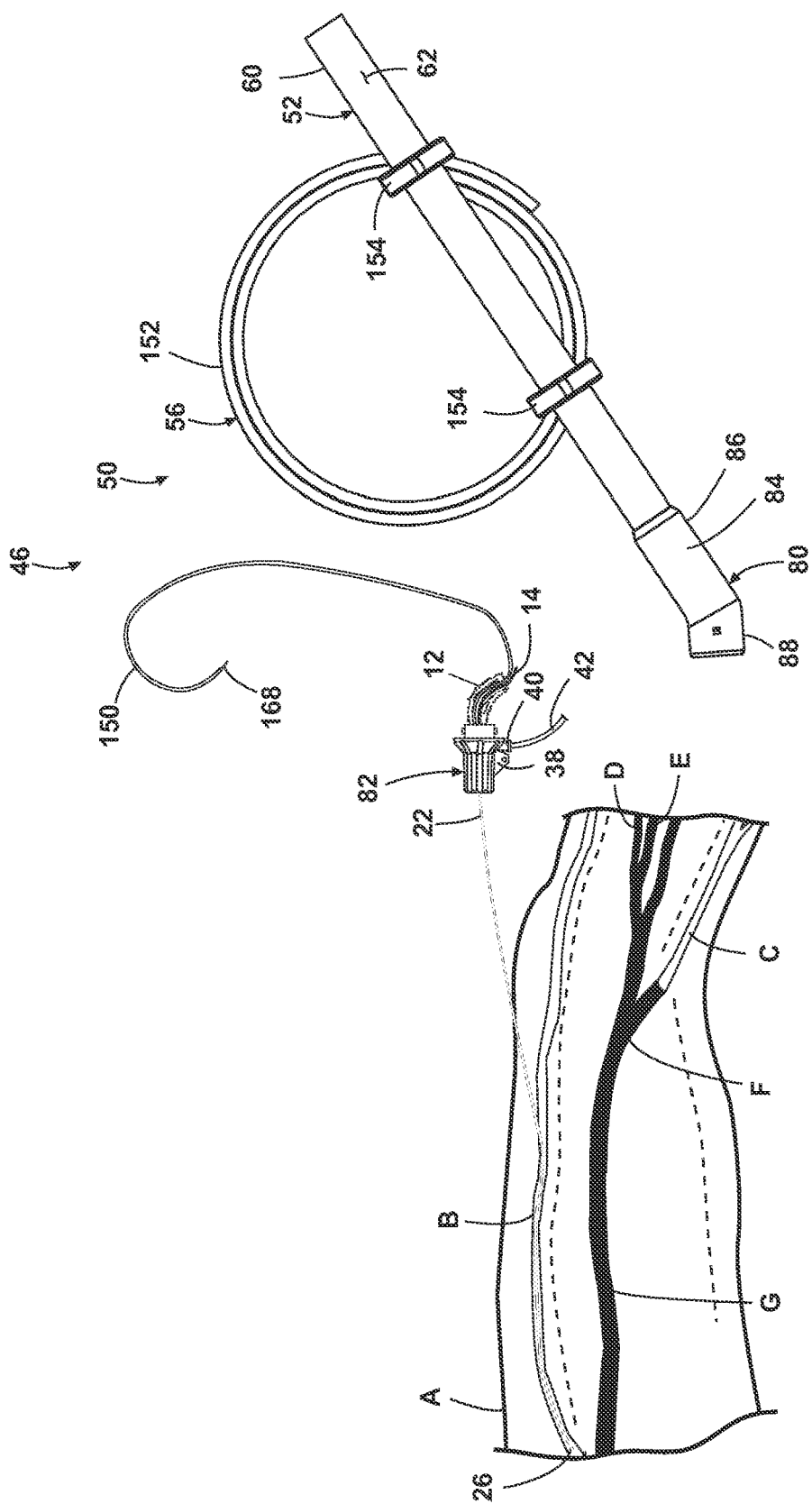

After the pushrod 150 and the implant 10 are advanced to the desired implant location, the practitioner disconnects the proximal coupler 80 from the distal coupler 82 and pulls the implant storage unit 52 and the proximal coupler 80 proximally away from the introducer sheath 20 a predetermined distance, as illustrated in FIG. 19. During the decoupling of the coupler assembly 54 and retraction of the implant storage unit 52, the pushrod 150 and the implant 10 remain in the position shown in FIG. 18 in the vein B; thus, the pushrod casing 152 moves proximally along the pushrod 150, thereby exposing a greater length of the pushrod 150. The predetermined distance between the introducer sheath 20 and the implant storage unit 52 can be selected to expose a predetermined length of the implant 10 between the introducer sheath 20 and the implant storage unit 52. In one embodiment, the practitioner pulls the implant storage unit 52 and the proximal coupler 80 to expose about 4 cm of the implant 10. The practitioner then trims the implant body 12 and the tether 14 at the exposed portion. After trimming the implant 10, the practitioner continues to pull the implant storage unit 52, the proximal coupler 80 and, thus, the pushrod casing 152, proximally away from the introducer sheath 20 to fully uncoil and expose the pushrod 150 and separate the pushrod 150 and the implant 10 from the remainder of the apparatus 50. FIG. 20 illustrates the introducer sheath 20, the pushrod 150, and the implant 10 in the leg A after removal of the implant storage unit 52.

Figure 21:
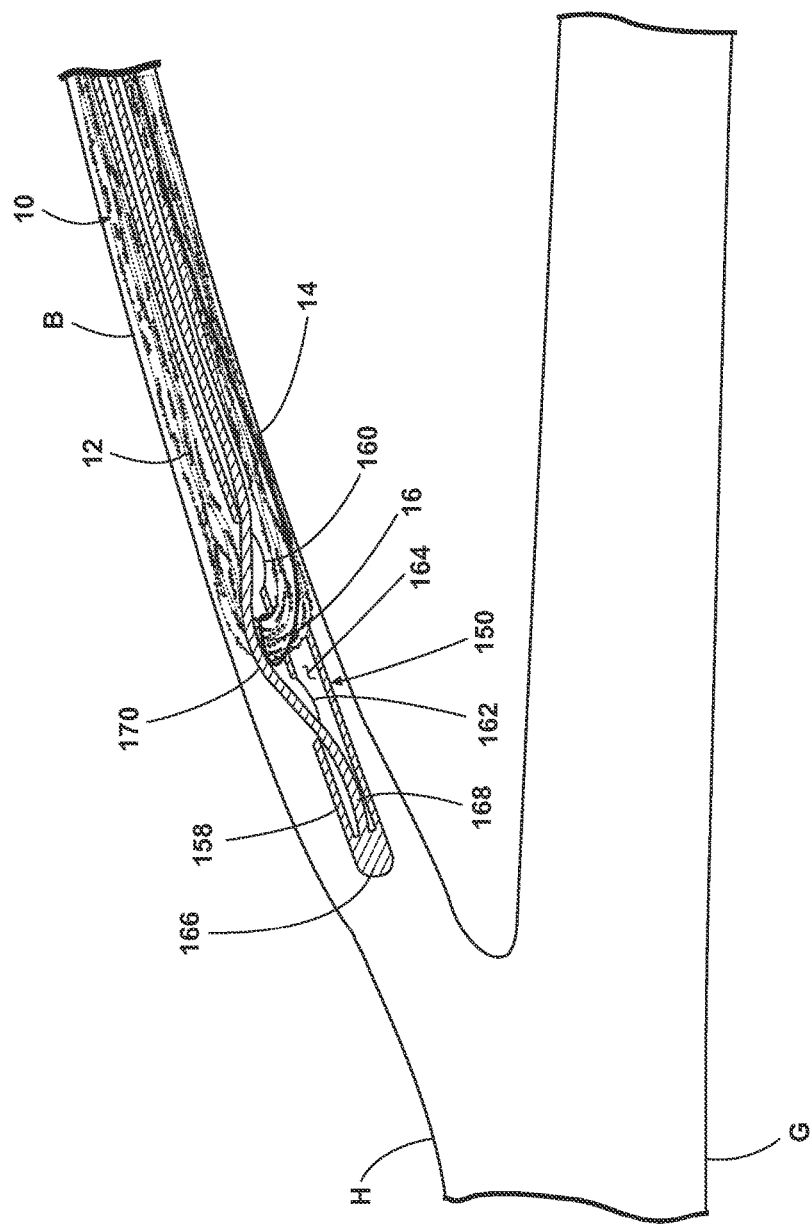

Removal of the introducer sheath 20 follows removal of the implant storage unit 52. In one embodiment, the practitioner removes the introducer sheath 20 by holding the pushrod 150 fixed to maintain the implant 10 just below the sapheno-femoral junction H and withdrawing the introducer sheath 20 completely from the vein B. As the introducer sheath 20 is withdrawn from the vein B, the implant body 12 expands from the compressed condition when in the introducer sheath shaft 22 to effectively fill the vein B less the space occupied by the pushrod 150. FIG. 21 illustrates the pushrod 150 and the implant 10 in the greater saphenous vein B after removal of the introducer sheath 20.

With the pushrod 150 and the implant 10 in the vein B, the practitioner releases the implant 10 from the pushrod 150. In one embodiment, the practitioner can withdraw the pushrod 150 a predetermined distance prior to releasing the implant 10. As an example, the practitioner can withdraw the pushrod 150 about 1 cm below the sapheno-femoral junction H to position the distal end 16 of the implant 10 about 2.5 cm below the sapheno-femoral junction H as the distal end 16 of the implant 10 in the illustrated embodiment is located about 1.5 cm proximally of the distal end of the pushrod 150. Withdrawal of the pushrod 150 after placement in the vein B but prior to releasing the implant 10 can reduce longitudinal tension in the body 12 of the implant and allow the body 12 near the distal end 16 the freedom and space to bulk up or expand even further from the expanded condition following removal of the introducer sheath 20.

Figure 22:
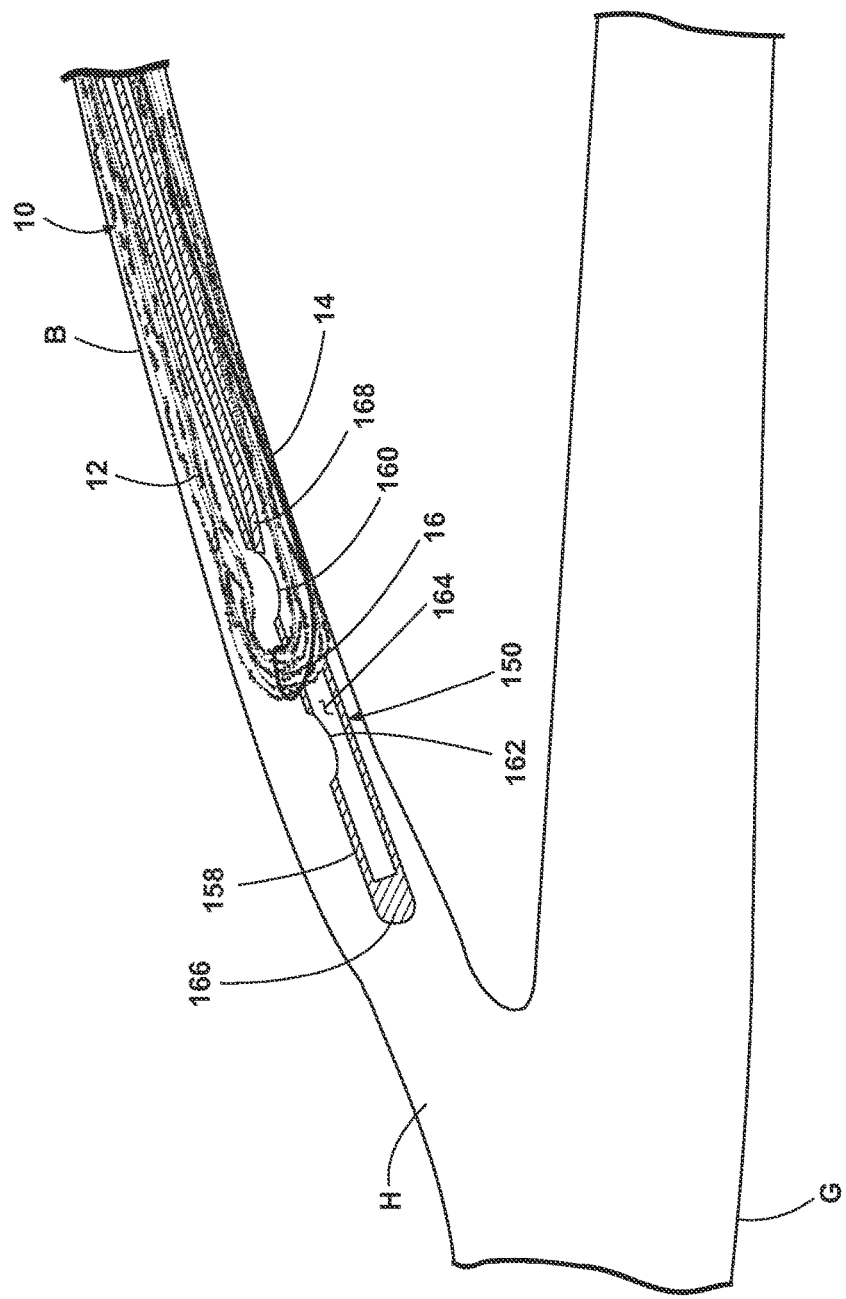

The practitioner then applies a proximal force to the wire 168, such as by pulling on the proximal end of the wire 168, thereby detaching the wire 168 from the distal plug 166. Continued application of the proximal force retracts the wire 168 through the openings 160, 162 and releases the implant 10 from between the wire 168 and the pushrod 150, as illustrated in FIG. 22. The wire 168 can be retracted any desired distance corresponding to releasing the implant 10 from the pushrod 150. For example, the wire 168 need not be retracted through the proximally located opening 160 if pulling the wire 168 through only the distally located opening 162 effects release of the implant 10. The retraction of the wire 168 through the proximally located opening 160 removes the implant retaining portion 170 from the implant 10 and gives the pushrod 150 a lower profile since the wire 168 is contained within the circumferential profile of the pushrod 150.

Figure 23:
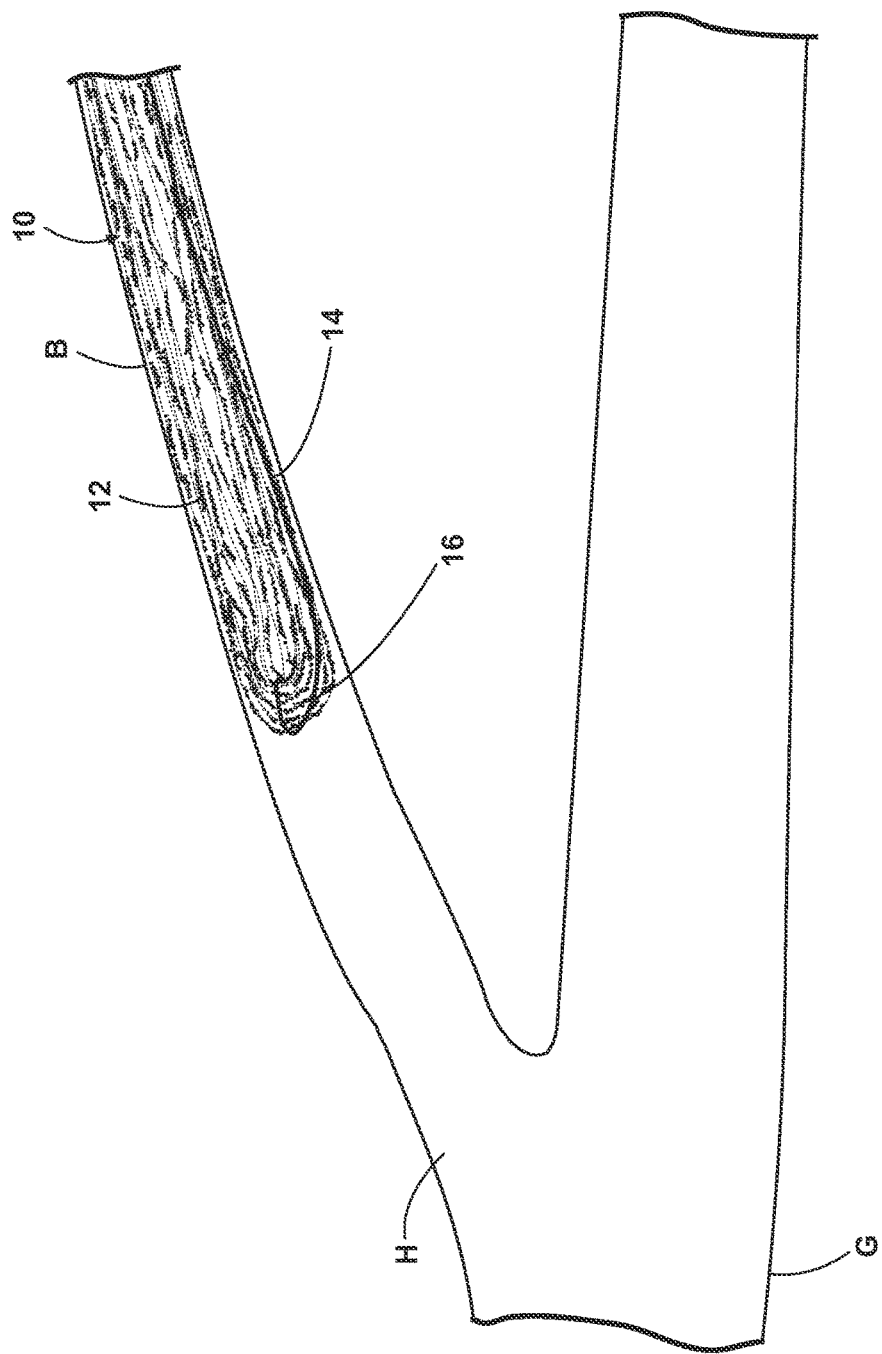

The practitioner follows release of the implant 10 with retraction of the pushrod 150 from the vein B. The removal of the implant retaining portion 170 when releasing the implant 10 and the lower profile during pushrod removal reduce the possibility of snagging the implant 10 on the pushrod 150 as the pushrod 150 is retracted from the vein B. If desired, the practitioner can apply external compression to the vein B and the implant 10 to maintain the position of the implant 10 in the vein B. The distal end 16 of the implant 10 retains its position in the vein B during retraction of the pushrod 150 due to its apposition against the vein wall, which is aided with coagulation or "sticking" by blood that is present in the vicinity. FIG. 23 illustrates the implant 10 in the greater saphenous vein B after removal of the pushrod 150.

Figures 24, 24A:
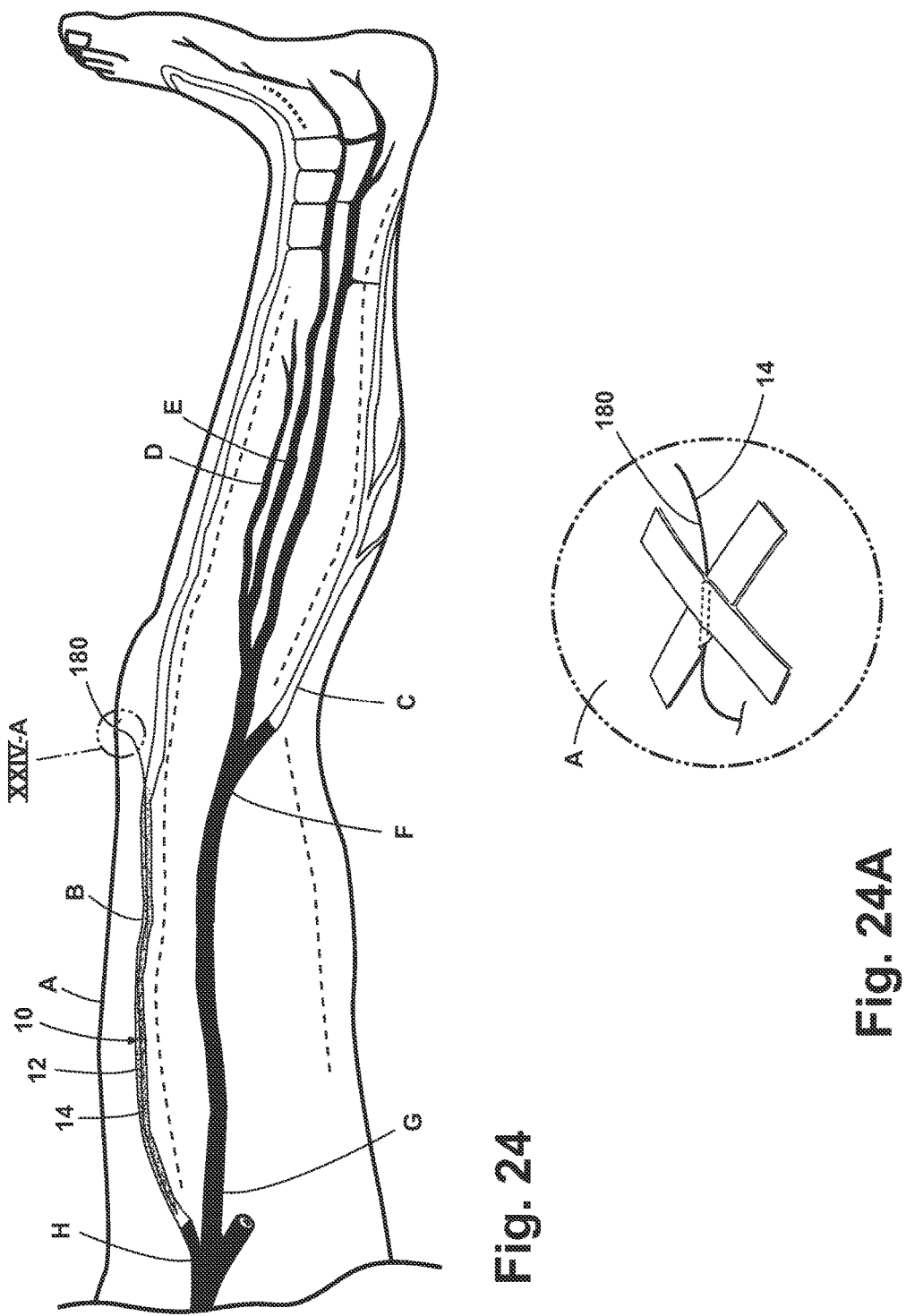

The practitioner can optionally secure the implant 10 to the leg A following removal of the pushrod 150. In one embodiment, the implant body 12 can be trimmed the location where the implant body 12 exits the leg A (i.e., the access site), and the tether 14 can be trimmed a desired length beyond the location where the tether 14 exits the leg A to form a tether securing portion 180 projecting from the leg A. The securing portion 180 can be taped or otherwise attached to the exterior surface, i.e., the skin, of the leg A, as shown in FIG. 24 and in greater detail in FIG. 24A, which is an enlarged view of the exterior surface of the leg A, particularly the region of the leg A labeled "XXIV-A" in FIG. 24. With the distal end 16 of the tether 14 attached to the distal end 16 of the implant body 12, and with the securing portion 180 attached to the skin, the tether 14 prevents migration of the implant 10 in the direction of the sapheno-femoral junction. In another embodiment, the implant 10, including the tether 14, can be secured to the access site by incorporation with access site sutures, such as 4-0 Vicryl braided or similar sutures.

Figure 25C:
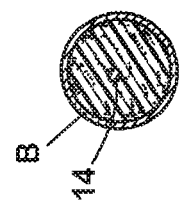
FIGS. 25A, 25B, and 25C provide sectional views of a body of the implant of FIG. 2 in storage, introduction, and implantation conditions, respectively.
Figure 25B:
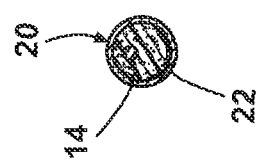
Figure 25A:
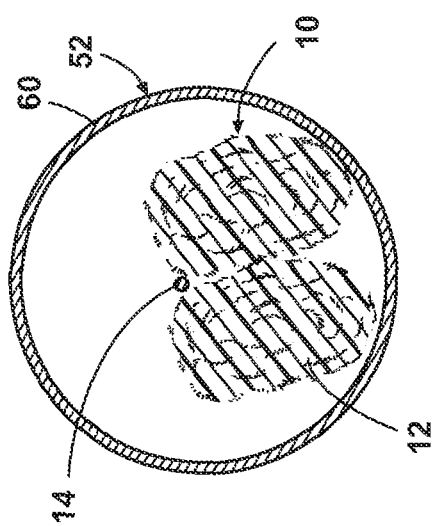

During the storage and introduction of the implant 10, the implant body 12 assumes multiple conditions with respect to the expansion and compression of the implant body 12. FIGS. 25A-25C illustrate sectional views of the implant body 12 in the exemplary conditions. As examples, the implant body 12 in the illustrated embodiment assumes an expanded condition when in the implant storage unit 52 of the apparatus 50 during storage (i.e., a storage condition, FIG. 25A), a first compressed condition when in the shaft 22 of the introducer sheath 20 during introduction (i.e., an introduction condition, FIG. 25B), and, assuming the HAS has a differing cross-sectional diameter than the shaft 22, a second compressed condition when in the HAS, shown as the greater saphenous vein B for illustrative purposes, after implantation (i.e., an implantation condition, FIG. 25C). The implant body 12 also undergoes transitional conditions when converting between the storage, introduction, and implantation conditions. These conditions are imposed on the implant body 12 because of the cross-sectional diameter of the structure that houses the implant body 12; once the housing structure cross-sectional diameter is sufficient to cause compression of the implant body 12, compression of the implant body 12 increases as the housing structure cross-sectional diameter decreases. The housing structures corresponding to the storage, introduction, and implantation conditions of the illustrated embodiment are, respectively, the tube 60 of the implant storage unit 52, the shaft 22 of the introducer sheath 20, and the HAS, in this case, the greater saphenous vein B.

The order of the steps described above for the method of use of the system 46 can be performed in any desired and suitable order and are not intended to be limited to the order the steps are described above. For example, the retraction of the pushrod 150 and the introducer sheath 20 can occur in any desired order, i.e., the pushrod 150 first, the introducer sheath 20 first, or the pushrod 150 and introducer sheath 20 simultaneously.

The method can be used with the illustrated apparatus 50, other embodiments of the illustrated apparatus 50, or other types of apparatuses for storage and/or introduction of the implant 10 or other suitable implant. Similarly, the apparatus 50 can be employed with the illustrated implant 10, other embodiments of the illustrated implant 10, or other types of occluding implants. The case is the same with respect to the use of the introducer sheath 20 with the apparatus 50.

The apparatus 50 can be provided as a ready-to-use kit having the implant 10 disposed in the implant storage unit 52 and connected to the pushrod 150 such that the apparatus 50 can be removed from its packaging for immediate surgical use. In one embodiment, the kit includes only the apparatus 50; alternatively, the kit can optionally include the introducer sheath 20 such that the entire system 46 is provided as a ready-to-use kit. In one embodiment, the apparatus 50 can be a single use device that is disposed after surgical use. Alternatively, the apparatus 50 can be a multiple use device that can be sterilized and provided with a new implant 10 and, if necessary, a new pushrod 150 having a new wire 168, for each surgical use.

FIG. 26 illustrates another embodiment of an apparatus 200 configured for storing and/or surgically introducing the implant 10 into a HAS, which apparatus 200 can be included in a system 190 with the implant 10 of FIG. 2, or other suitable implant, and the introducer sheath 20 of FIG. 3, or other suitable introducer sheath. The apparatus 200 can be similar in structure, function and method of use to the apparatus 50 of FIGS. 4-25C, except as further described herein. The depicted apparatus 200 comprises a coupler assembly 202 configured to couple the apparatus 200 to an introducer sheath, such as the introducer sheath 20 of FIG. 3, and a combined implant storage/introducer unit 204 adapted to store the implant 10 prior to and during introduction of the implant 10 into the HAS. The storage/introducer unit 204 is adapted to feed the implant through the coupler assembly 202, and into the introducer sheath 20 for placement of the implant 10 in the HAS, when manipulated by the practitioner.

Figure 27:
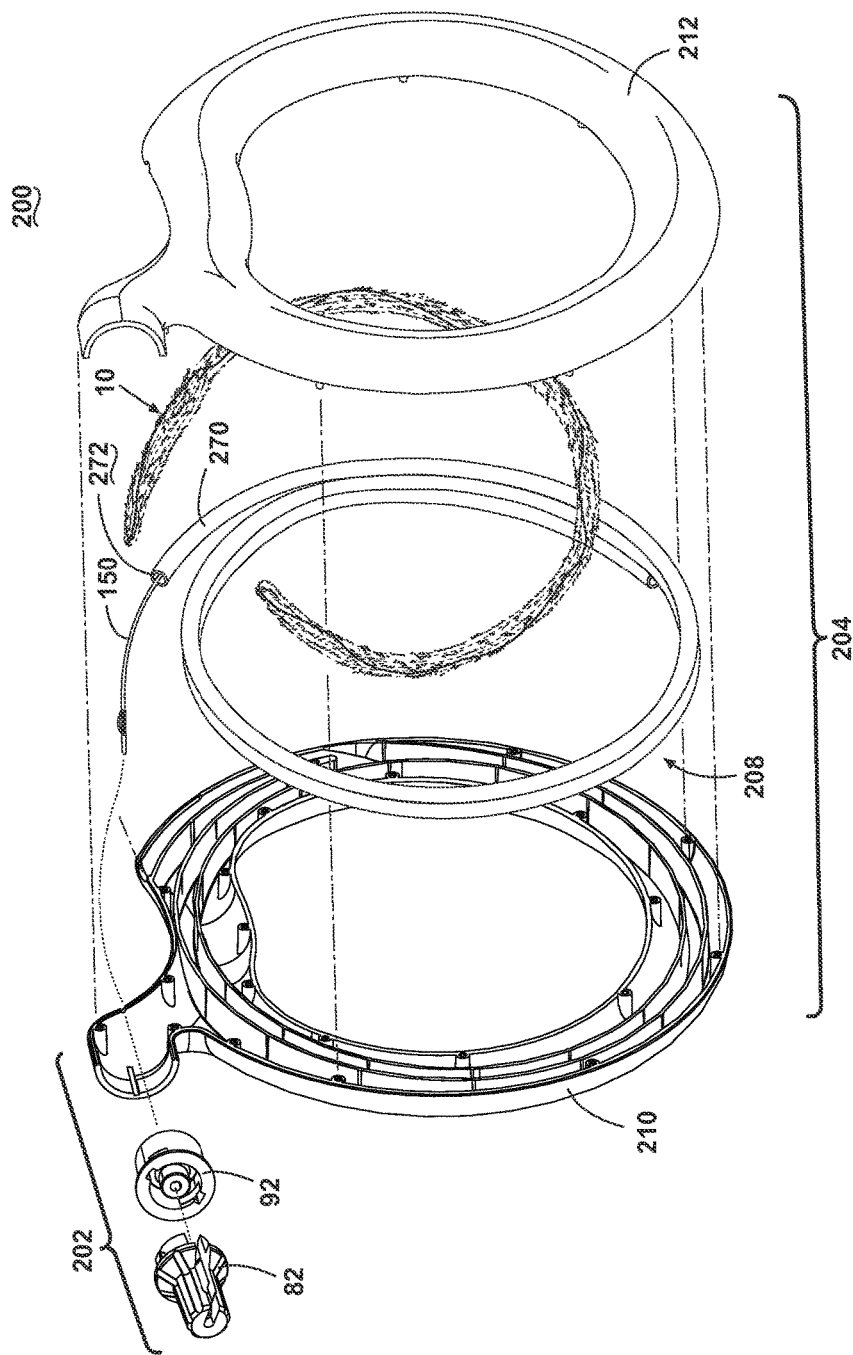
FIG. 27 is an exploded view of the apparatus shown in FIG. 26.

With additional reference to FIG. 27, where the apparatus 200 is illustrated as exploded, the implant storage/introducer unit 204 of the depicted embodiment comprises a single casing 206 sized to accommodate both the implant 10 and an introducer assembly 208, as will be disclosed in further detail below. The casing 206 comprises a right housing shell and 210 a left housing shell 212 adapted for cooperative registry.

Referring to FIG. 28, the right housing shell 210 comprises a curved side wall 214 joined to an inner wall 216 and an outer wall 218. The walls 214, 216, 218 are contoured, and can be configured with openings, bosses, flanges, and the like, for operational support of the elements comprising the apparatus 200. The right housing shell 210 can be molded such that the openings, bosses, flanges, and the like are integrally formed with the right housing shell 210. As illustrated, the continuity of the outer wall 218 is interrupted by a first opening 220 and a second opening 222. The right housing shell 210 further has multiple hollow bosses 224 spaced along the inner and outer walls 216, 218.

A first, inner flange 226 extends from the side wall 214 in spaced relation to the inner wall 216 and forms a closed loop. A second, middle flange 228 extends mainly from the side wall 214 in spaced relation to the inner flange 226. The middle flange 228 has a first end 230 and a second end 232 that do not meet each other; rather, the middle flange 228 is formed as a spiral, with the first end 230 being disposed on the side wall 214 and inwardly spaced from the outer wall 218, and the middle flange 228 gradually spirals outwardly until the second end 232 joins the outer wall 218. A third, outer flange 234 extends mainly from the side wall 214 and has a first end 239 which meets the outer wall 218 adjacent the first opening 220 and a second end 236 which joins with the first end 230 of the middle flange 228. The flanges 226, 228, 234 cooperatively form a channel 240 in communication with the first opening 220, with the channel 240 following a generally spiral-shaped path defined by the flanges 226, 228, 234. The channel 240 at least partially receives and/or stores the introducer assembly 208, as will be described below.

The left housing shell 212, shown in FIG. 29, is generally a mirror image of the right housing shell 210, and includes some, but not all, of the same structural elements of the right housing shell 210. Particularly, as illustrated, the left housing shell 212 preferably does not include any flanges or hollow bosses, but does include a curved side wall 242 joined to an inner wall 244 and an outer wall 246 with first and second openings 248, 250, respectively, in mirrored-relation to those corresponding features of the right housing shell 210. The walls define a cavity 252 in which the implant 10 is at least partially stored, as will be described below. The left housing shell 212 further has multiple projections 254 spaced along the inner and outer walls 244, 248 for receipt within the hollow bosses 224 on the right housing shell 210. The left housing shell 212 can be molded such that the openings, projections, and the like are integrally formed with the left housing shell 212.

Figure 30:
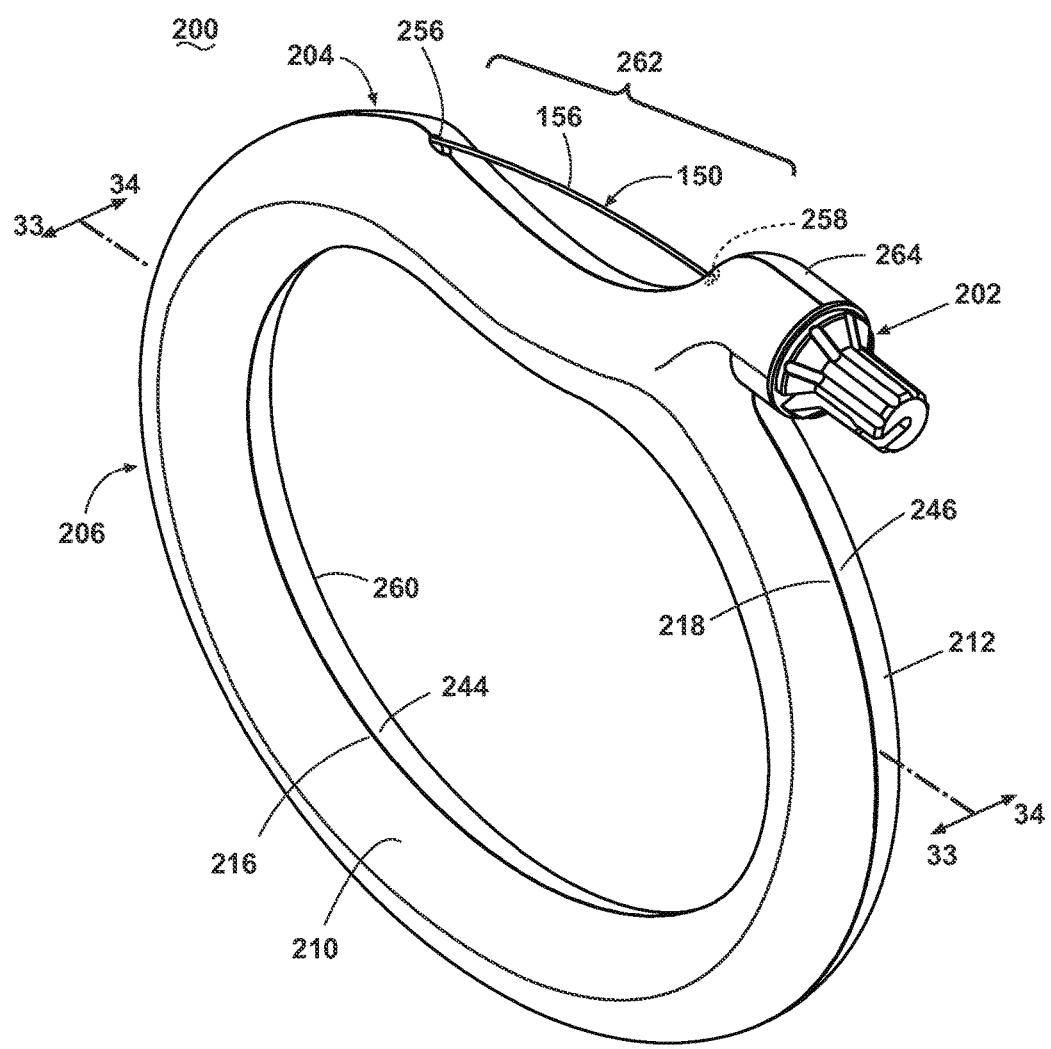
FIG. 30 is perspective view of the apparatus shown in FIG. 26.

Referring to FIG. 30, when the right and left housing shells 210, 212 are assembled, the hollow bosses 224 (FIG. 28) receive the projections 254 (FIG. 29) and the inner walls 216, 244 and the outer walls 218, 246 meet in cooperative registry to form the casing 206. The first openings 220, 248 register to form a single first aperture 256 and the second openings 222, 250 register to form a single second aperture 258; thus, in total, the assembled casing 206 can form two apertures.

The assembled casing 206 has a closed-loop portion 260 that that is generally oval in shape except for a saddle-like portion 262 and a coupler portion 264 extending generally from one of the junctures between the closed-loop portion 260 and the saddle-like portion 262. The first aperture 256 is formed at or near one end of the saddle-like portion 262 and the second aperture 258 is formed at the coupler portion 264 (which can be at or near the opposite end of the saddle-like portion 262). The second aperture 258 can be generally collinear with the longitudinal axis of the coupler portion 264. The channel 240 (FIG. 28) that at least partially receives and/or stores the introducer assembly 208 and the cavity 252 (FIG. 29) in which the implant 10 is at least partially stored are both generally formed along and situated within the closed-loop portion 260 and the saddle-like portion 262.

The casing 206 can be shaped to facilitate comfortable gripping of the implant storage/introducer unit 204. The implant storage/introducer unit 204 can be gripped according to the practitioner's preference, such as with one hand wrapped around the saddle-like portion 262 or part of the closed-loop portion 260, although other gripping arrangements or techniques are possible.

Figure 31:
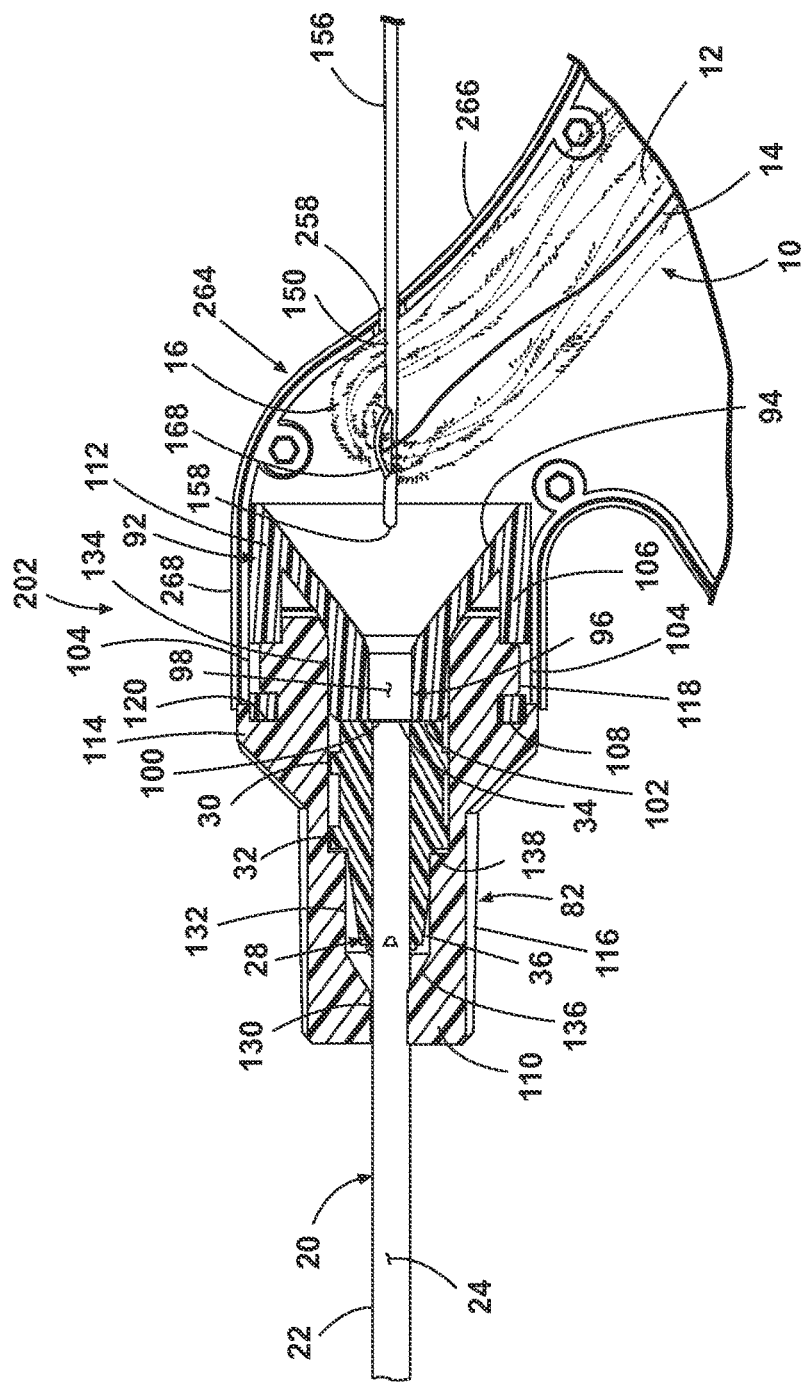
FIG. 31 is a sectional view of distal portions of the system of FIG. 26 with an introducer of the apparatus in a storage position according to one embodiment.
Figure 32:
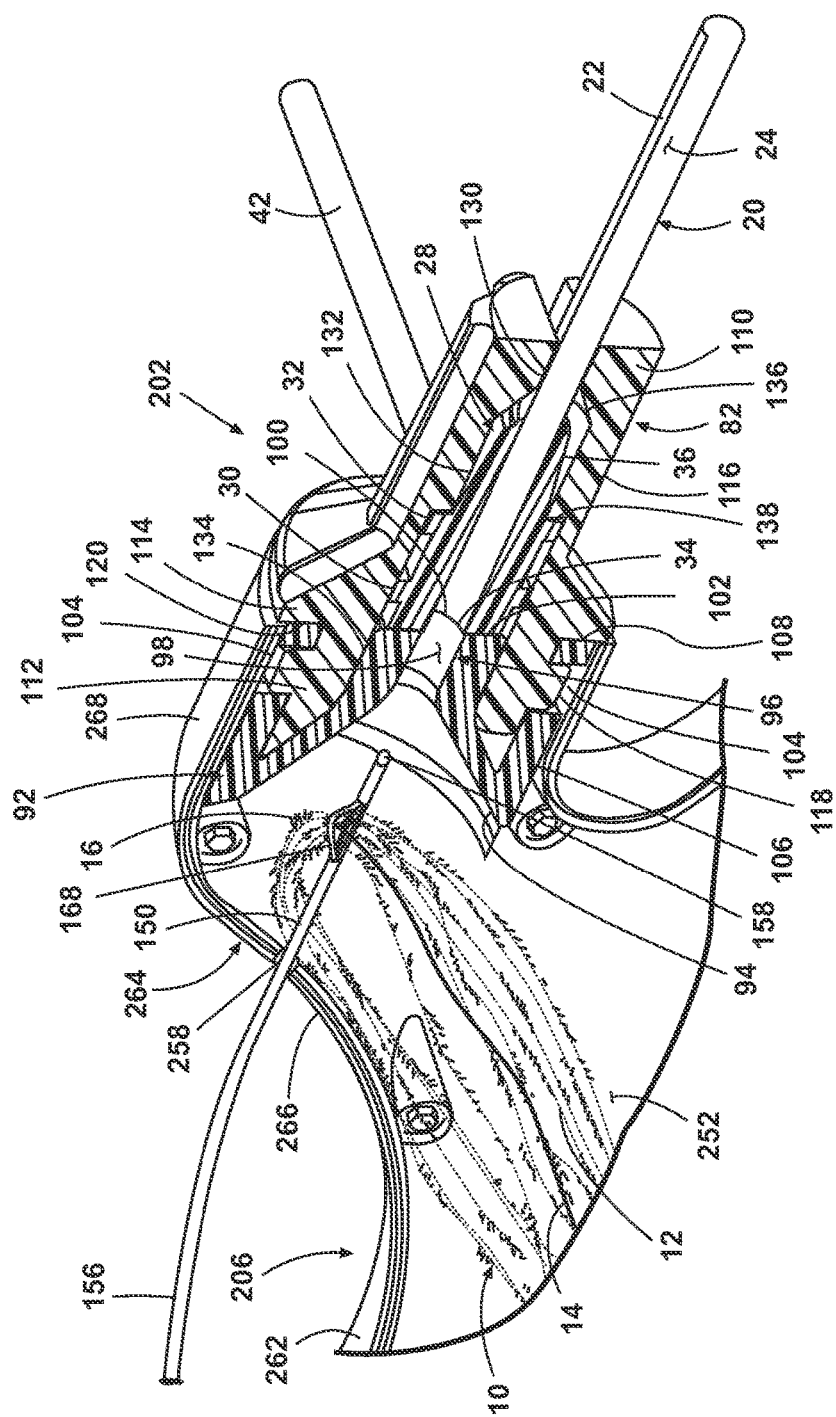
FIG. 32 is a perspective view of FIG. 31.

Referring now to FIGS. 31 and 32, which are enlarged views of the region labeled "XXXI" in FIG. 26, the depicted coupler assembly 202 that couples the apparatus 200 to the introducer sheath 20 is shown. The coupler assembly 202 can comprise a distal coupler that can be similar or identical to the distal coupler 82 shown in FIGS. 7-10, and will therefore not be further described for this embodiment, and like elements of the distal coupler 82 will be referred to with the same reference numerals. The coupler assembly 202 further comprises a proximal coupler which mates with the distal coupler 82. In the depicted embodiment, the proximal coupler is integrally formed as part of the casing 206 as the coupler portion 264, and therefore may alternately be considered part of the implant storage/introducer unit 204 rather than the coupler assembly 202. The coupler portion or proximal coupler 264 includes a tubular conduit having a storage portion 266 and a coupling portion 268. As best viewed in the perspective view of FIG. 32, the storage portion 266 joins the saddle-like portion 262 of the casing 206 to thereby connect the cavity 252 in which the implant 10 is at least partially stored, and the storage portion 266 of the proximal coupler 264. The casing 206 and the proximal coupler 264 do not have to be integrally molded, and can be joined in any suitable fashion, such as, for example, an interference fit, with an adhesive, a snap fit, etc. The second aperture 258 is formed through a side wall of the storage portion 266, and is aligned and can be generally collinear with the longitudinal axis of the coupling portion 268 and the exit opening 100, and, when the system 190 is assembled, the proximal opening 30 of the hub 28 and the lumen 24 of the introducer sheath shaft 22.

As shown in FIGS. 31 and 32, the coupling portion 268 houses an insert that can be similar or identical to the insert 92 shown in FIGS. 8-9, and will therefore not be further described for this embodiment, and like elements of the insert 92 will be referred to with the same reference numerals. In this embodiment, the channel 98 and the exit opening 100 of the insert 92 are oriented in axial alignment with the second aperture 258. The insert 92 can be secured to the coupling portion 268 in any suitable fashion, such as, for example, an interference fit, with an adhesive, a snap fit, etc.; alternatively, the insert 92 or the features of the insert 92 can be integrally formed with the coupling portion 268. The insert 92 will in turn receive the distal coupler 82 as described for the apparatus 50 of FIGS. 4-14.

While the proximal coupler 264 has been described as comprising the storage portion 266 and the coupling portion 268 that houses the insert 92, the proximal coupler 264 can alternatively be considered as comprising only the insert 92, which performs a coupling function, with the casing 206, which performs a storage function, considered as an extension or part of the implant storage/introducer unit 204. Regardless, the exit opening 100 functions as an exit opening for the implant storage/introducer unit 204 and the overall apparatus 200 as the implant 10 exits the implant storage/introducer unit 204 and the apparatus 200 through the exit opening 100. The proximal coupler 264 and the insert 92 can be constructed in any desired manner with either or both parts functioning to partially store the implant 10 and/or couple the apparatus 200 to the introducer sheath 20.

The proximal and distal couplers 264, 82 of the coupler assembly 202 can be connected together, as shown in FIGS. 31 and 32, to couple the apparatus 200 to the introducer sheath 20. In the coupled condition, the proximal and distal couplers 264, 82 retain the hub 28 of the introducer sheath 20 therebetween, as described above with respect to FIGS. 8-9. In the current embodiment, due to the placement of the hub 28 relative to the proximal and distal couplers 264, 82, the second aperture 258 and the channel 98 align axially with the proximal opening 34 of the hub 28 and, thereby, the lumen 24 at the proximal end of the shaft 22.

Referring back to FIG. 27, the depicted embodiment of the implant storage/introducer unit 204 of the apparatus 200 comprises the introducer assembly 208 partially stored within the casing 206 along with the implant 10. The introducer assembly 208 includes an introducer or pushrod that can be similar or identical to the pushrod 150 shown in FIGS. 8-9, and will therefore not be further described for this embodiment, and like elements of the insert 150 will be referred to with the same reference numerals. In this embodiment, the introducer assembly 208 further comprises a tubular housing 270 defining a lumen 272 in which the pushrod 150 is partially stored. The length of the housing 270 is sufficient to encase the proximal end of the pushrod 150 prior to use of the apparatus 200 for delivery of the implant 10. Further, the housing 270 can be coiled one or more times within the casing 206 to accommodate the length of the pushrod 150 and, thereby, maintain a relatively compact configuration for the apparatus 200.

Figure 33:
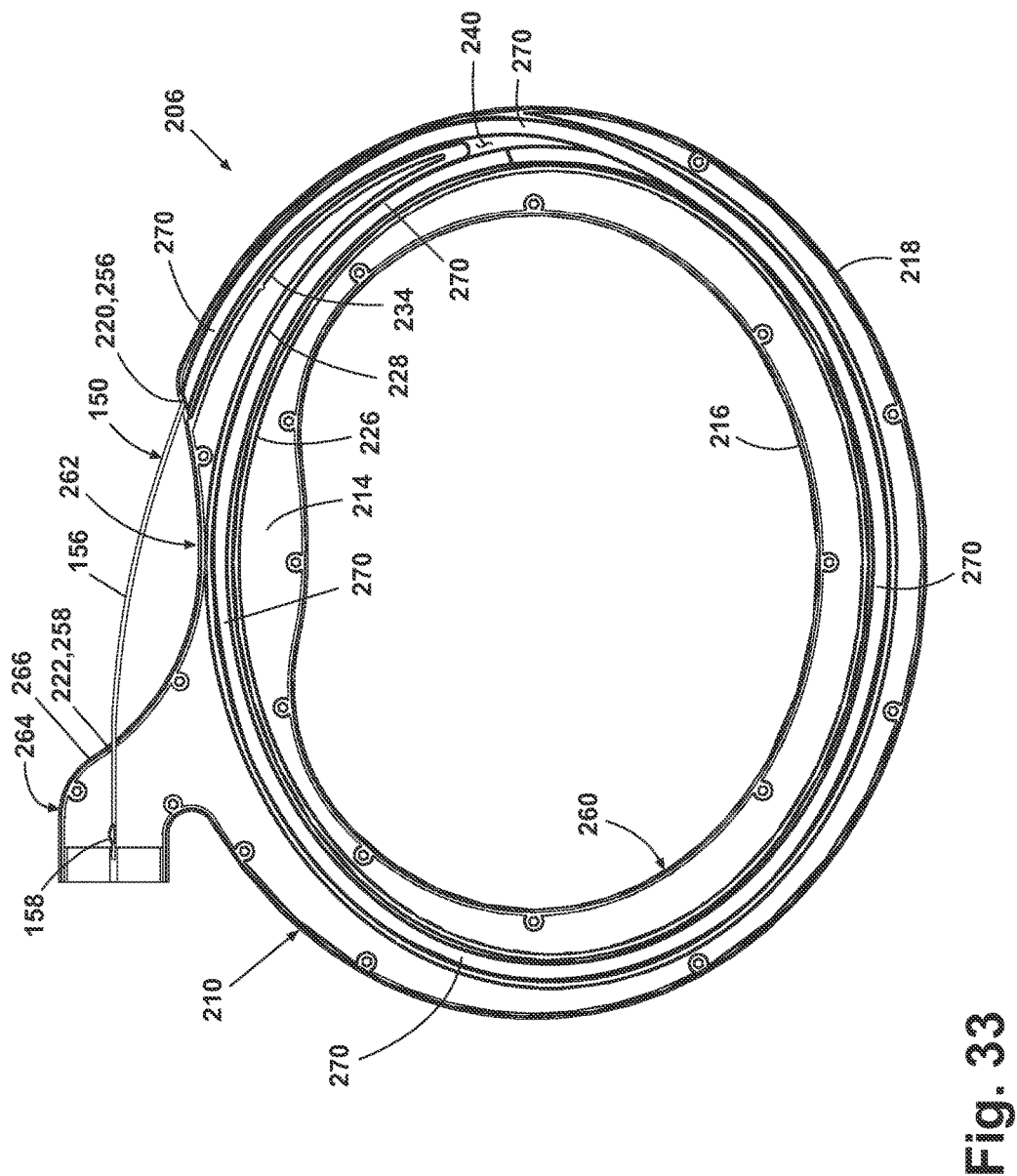
FIG. 33 is a sectional view through line 33-33 of FIG. 30.

As shown in FIGS. 33-36, the implant 10 and the introducer assembly 208 are commonly stored by the casing 206. As shown in FIG. 33 in particular, in which the implant 10 is not shown for clarity, the introducer assembly 208 is received in and retained by the right housing shell 210 by placing the housing 270 in the channel 240 created by the flanges 226, 228, 234, with the distal end of the pushrod 150 extending out of the first aperture 256 and into the second aperture 258. The pushrod 150 projects from the distal end of the housing 270, through the first and second apertures 256, 258, and into the proximal coupler 264, where it terminates at a distal tip region, which can be similar or identical to the distal tip region 158 shown in FIG. 11, and will therefore not be further described for this embodiment, and like elements of the distal tip region 158 will be referred to with the same reference numerals.

The exposed portion 156 of the pushrod 150 between the two apertures 256, 258 provides a gripping area for the practitioner to grasp, either manually or through the operation of a motorized drive system, or a non-motorized drive system, gear train, or other mechanism that engages the pushrod 150, and manipulate the pushrod 150, and can generally follow the natural curve created by the closed-loop portion 260 of the casing 206. The exposed portion 156 generally extends over the saddle-like portion 262 of the casing 206, and the offset between the pushrod 150 and the saddle-like portion 262 allows the practitioner to grip and apply force to (e.g., push distally or pull proximally) the pushrod 150 at a location close to its distal tip region 158.

Figure 35:
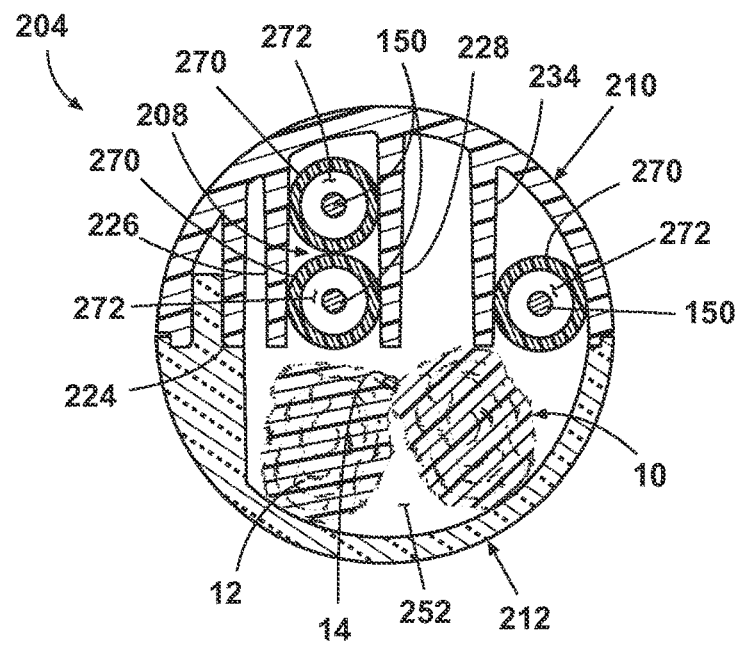
FIG. 35 is a sectional view through line 35-35 of FIG. 26.
Figure 36:
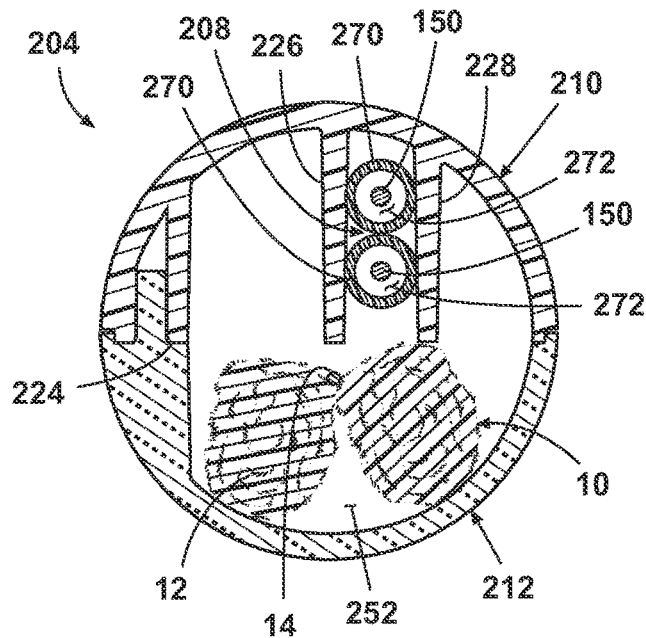
FIG. 36 is a sectional view through line 36-36 of FIG. 26.

As best viewed in the sectional views of FIGS. 35 and 36, the housing 270 can be coiled one or more times to extend along the channel 240. The flanges 226, 228, 234 function as guides and help maintain the housing 270 in an orderly coil within the casing 206.

Figure 34:
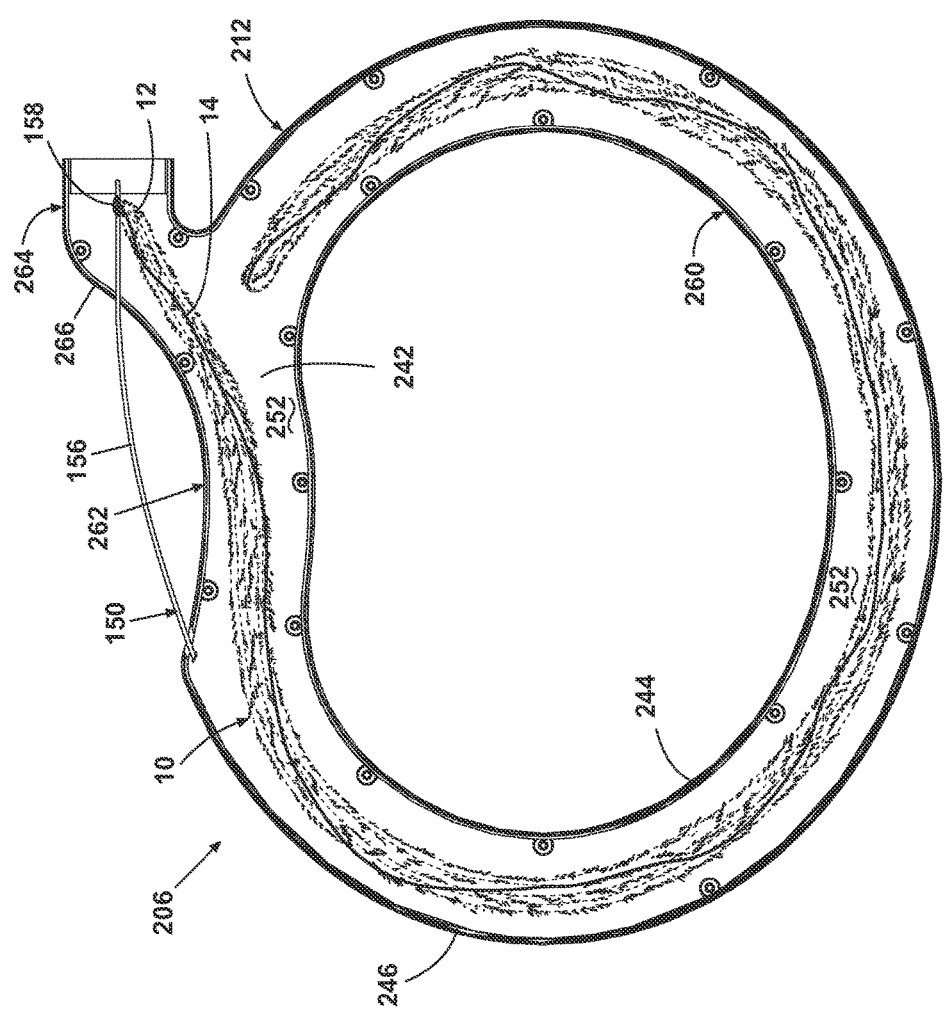
FIG. 34 is a sectional view through line 34-34 of FIG. 30, with only a portion of a pushrod is shown for clarity.

As shown in FIG. 34 in particular, in which a portion of the pushrod 150 is shown for clarity, the implant 10 is received in the cavity 252 of the left housing shell 212. The implant 10 attaches to the distal tip region 158 in a manner similar to that described above with reference to FIGS. 11 and 12, and will therefore not be further described for this embodiment. The implant 10 generally extends back from its point of attachment to the distal tip region 158 of the pushrod 150, through the storage portion 266 of the proximal coupler 264, and through the cavity 252 for storage in the storage portion 266 and the casing 206, as can further be seen in FIG. 34. As a result, the implant 10 extends from the pushrod 150, which is positioned in the proximal coupler 264, along the saddle-like portion 262, and around the closed-loop portion 260 of the casing 206.

The components in which the implant 10 is stored, specifically the storage portion 266, the saddle-like portion 262, and the closed-loop portion 260 (the portions 266, 262, 260) of the casing 206 in the depicted embodiment, can be sized to accommodate the implant 10. In one embodiment, the portions 266, 262, 260 have a collective effective length (i.e., the length of the storage portion 266 plus the length of the saddle-like portion 262 plus the length of the closed-loop portion 260, less any overlap between the components) corresponds to the length of the implant 10, that is, the distance between the distal and proximal ends 16, 18 of the body 12 of the implant 10. In such an embodiment, the body 12 of the implant 10 extends the collective effective length of the portions 266, 262, 260 with no or minimal bunching or folding of the body 12. Alternatively, the collective length of the portions 266, 262, 260 can be less than the length of the body 12 such that the body 12 undergoes some bunching or folding upon itself within the portions 266, 262, 260. In yet another embodiment, the collective length of the portions 266, 262, 260 can be greater than the length of the body 12.

Further, as illustrated in the exemplary embodiment, the storage portion 266 and the cavity 252 can be sized sufficiently large to accommodate the implant 10 in its natural or default expanded condition. Alternatively, the storage portion 266 and the cavity 252 can each have a size that effectively compresses the implant 10 from its expanded condition to a compressed condition, at any appropriate degree of compression. As best viewed in the sectional views of FIGS. 35 and 36, the ends of the flanges 226, 228, 234 may help retain the implant 10 within the cavity 252.

The pushrod 150 can be manipulated by the practitioner between various positions for introducing the implant 10 into a HAS. FIGS. 31 and 32 illustrate a retracted or storage position of the pushrod 150; the storage position corresponds to a position of the pushrod 150 and, thereby, the implant 10 prior to use of the apparatus 200 for introduction of the implant 10 into the HAS (i.e., during storage). In the exemplary storage position of FIGS. 31 and 32, the distal tip region 158 of the pushrod 150 resides in the proximal coupler 264, particularly at the bend between the storage portion 266 and the coupling portion 268 of the tubular conduit, and in axial alignment with the channel 98.

FIGS. 31 and 32 illustrate an exemplary storage position; other storage positions are possible. In other exemplary storage positions, the distal tip region 158 of the pushrod 150 can be located proximally of that shown in FIGS. 31 and 32, such as between the second aperture 258 and the position shown in FIGS. 31 and 32. Alternatively, the distal tip region 158 of the pushrod 150 can be located distally of that shown in FIGS. 31 and 32, such as between the position shown in FIGS. 31 and 32 and the exit opening 100 of the proximal coupler 64. As another alternative, the pushrod 150 can project beyond the exit opening 100 with the implant 10 residing within the casing 206.

Figure 37:
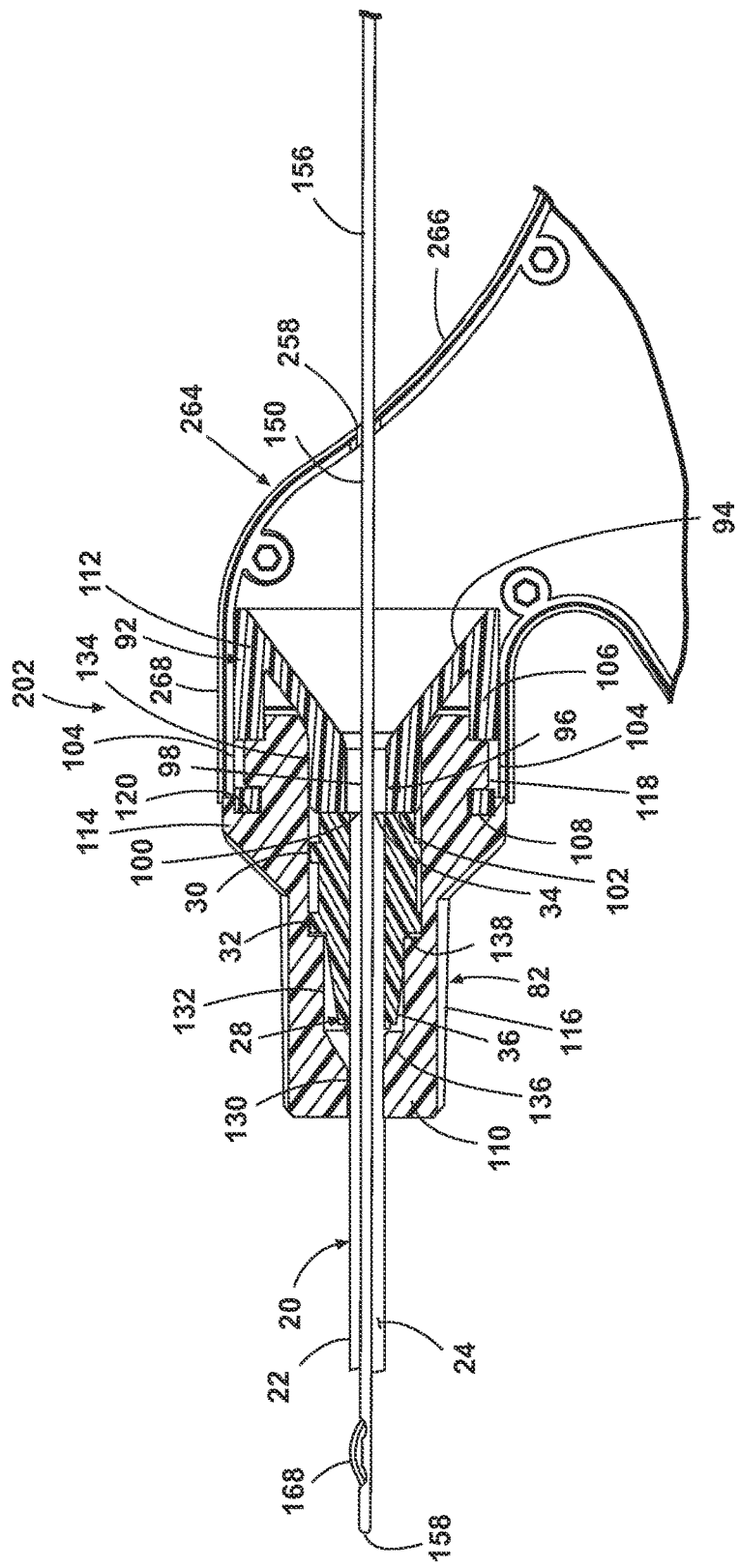
FIG. 37 is a sectional view similar to FIG. 31 with the introducer of the apparatus of FIG. 26 in an advancing position according to one embodiment; the implant is not shown for clarity.
Figure 38:
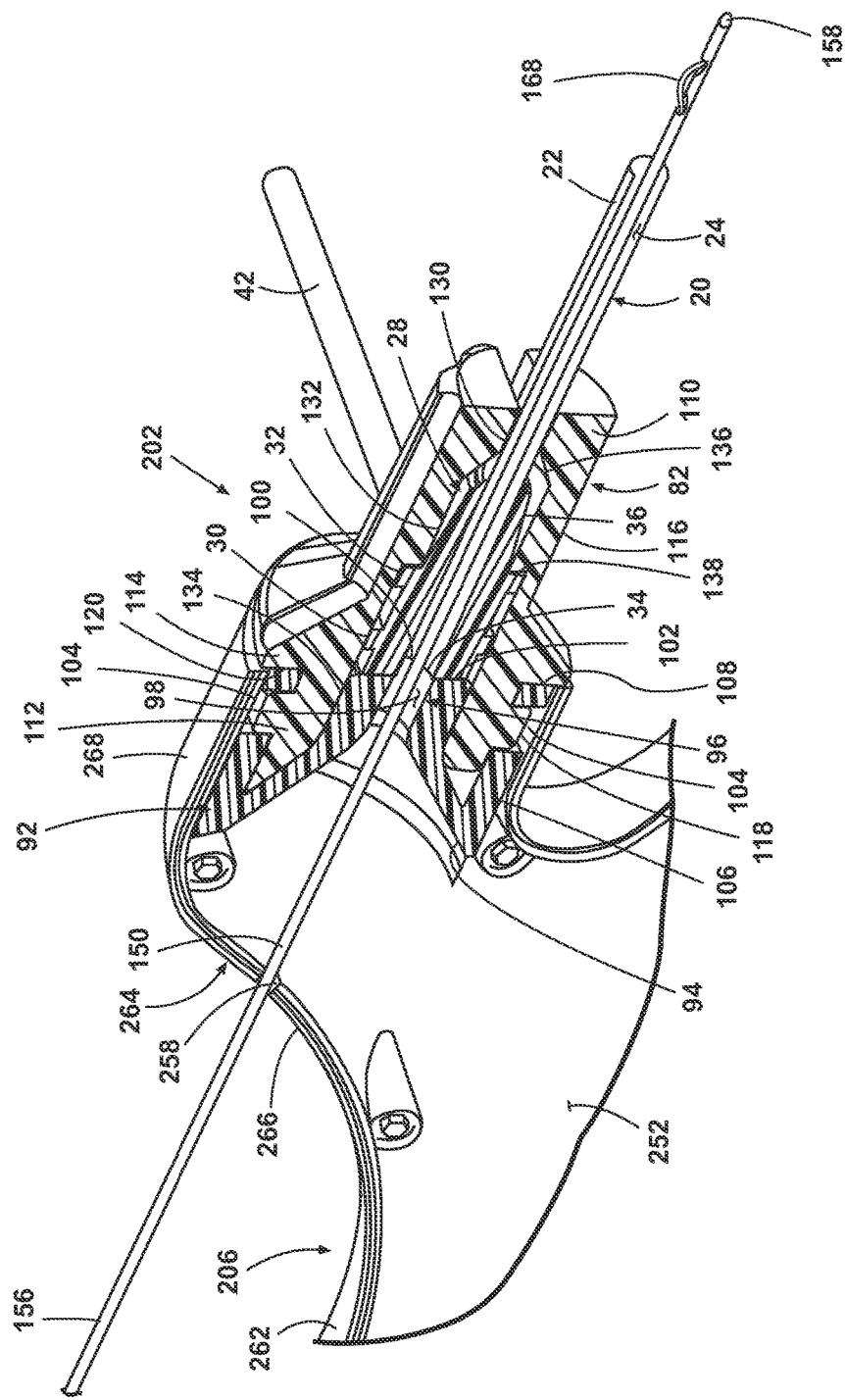
FIG. 38 is a perspective view of FIG. 37; the implant is not shown for clarity.

FIGS. 37 and 38 illustrate an advancing position of the pushrod 150; the advancing position corresponds to a position of the pushrod 150 and, thereby, the implant 10 during use of the apparatus 200 for introduction of the implant 10 into the HAS. In the advancing position, the distal tip region 158 of the pushrod 150 is located distally of its location when in the storage position; therefore, any distal movement of the pushrod 150 from the storage position tends to move the pushrod 150 to (or towards) the advancing position. FIGS. 37 and 38 illustrate an exemplary advancing position with the implant 10 not shown for clarity. When moving the pushrod 150 from the storage position to the advancing position, the distal tip region 158 of the pushrod 150 advances through the channel 98 and exit opening 100 of the proximal coupler 264 and into the introducer sheath 20, particularly into the hub proximal opening 34, through the hub 28, including the collar 36, and into the shaft lumen 24 of the introducer sheath 20, which is held by the distal coupler 82. As the pushrod 150 so advances, the implant 10 is compressed radially and elongated as it is forced through the tapering introducer guide 94 and into the lumen 24 of the introducer sheath 20. Thus, when advancing, the pushrod 150 and the implant 10 have a common travel direction leaving the apparatus 200 through the exit opening 100 and entering the introducer sheath 20 through the proximal opening 34. In the illustrated embodiment, the travel direction is substantially linear, but other forms of travel direction are possible depending on the configuration of the apparatus 200. Other positions of the pushrod 150 will be described below in conjunction with the description of methods of use of the system 190.

Embodiments of methods of use of the system 190 are described below. While the system 190 can be employed in conjunction with any suitable HAS, the methods are described with respect to the greater saphenous vein B for illustrative purposes. It will be understood that the methods can be modified or adapted as necessary, if necessary, for use in other HASs. The methods can also be modified or adapted, as necessary, for use with embodiments of the system 190 other than the embodiment employed in the following description. Aspects of the method of use of the system 190 that overlap with the method of use of the system 46, described above, will be briefly summarized, but will not be described in detail. In the description of the methods, the various steps are discussed in terms of being performed by the practitioner; however, it is understood that these steps may be performed by the practitioner manually or through the operation of a motorized or non-motorized drive system, gear train, mechanism, etc.

Figure 39:
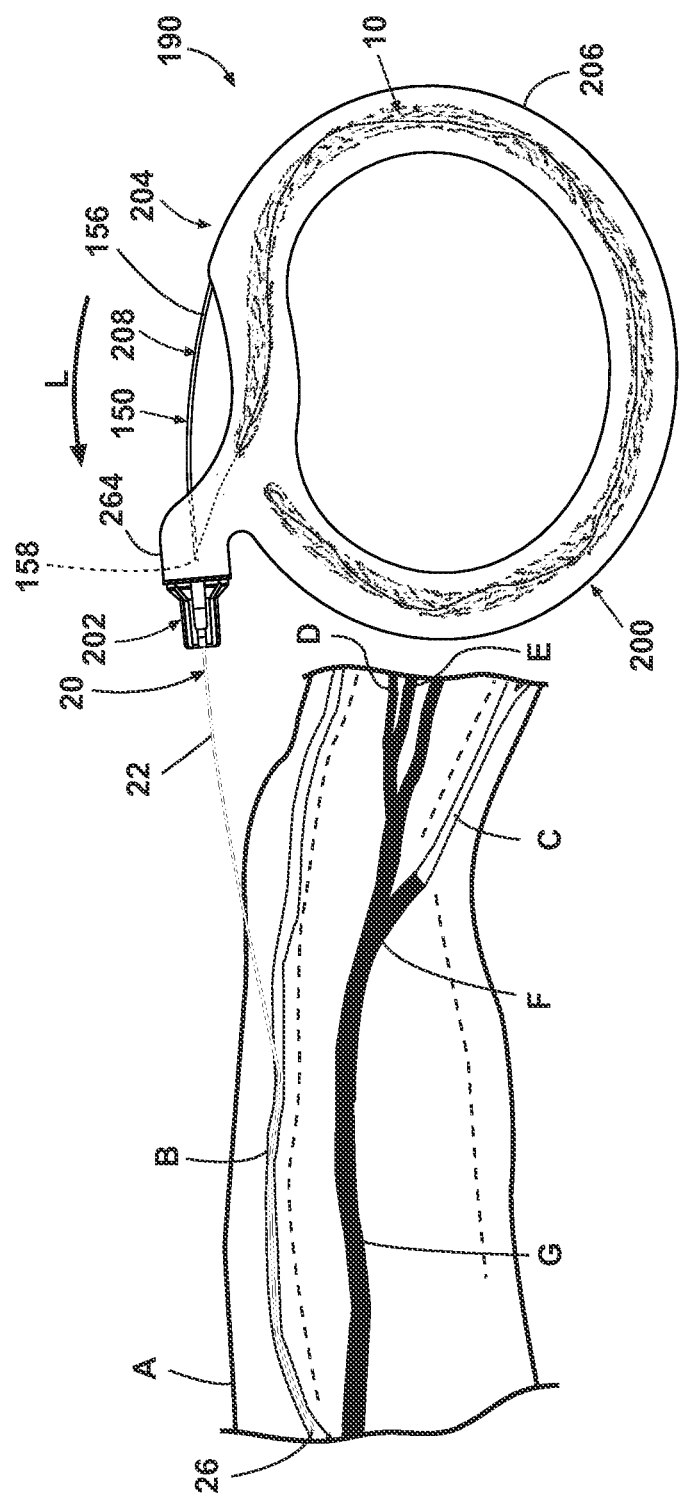
FIG. 39 illustrates the leg of FIG. 1 with a shaft of the introducer sheath of FIG. 3 located in the greater saphenous vein of the leg, the distal coupler of the apparatus of FIG. 26 mounted to the introducer sheath, and the apparatus of FIG. 26 mounted to the distal coupler and introducer sheath.
Figure 40:
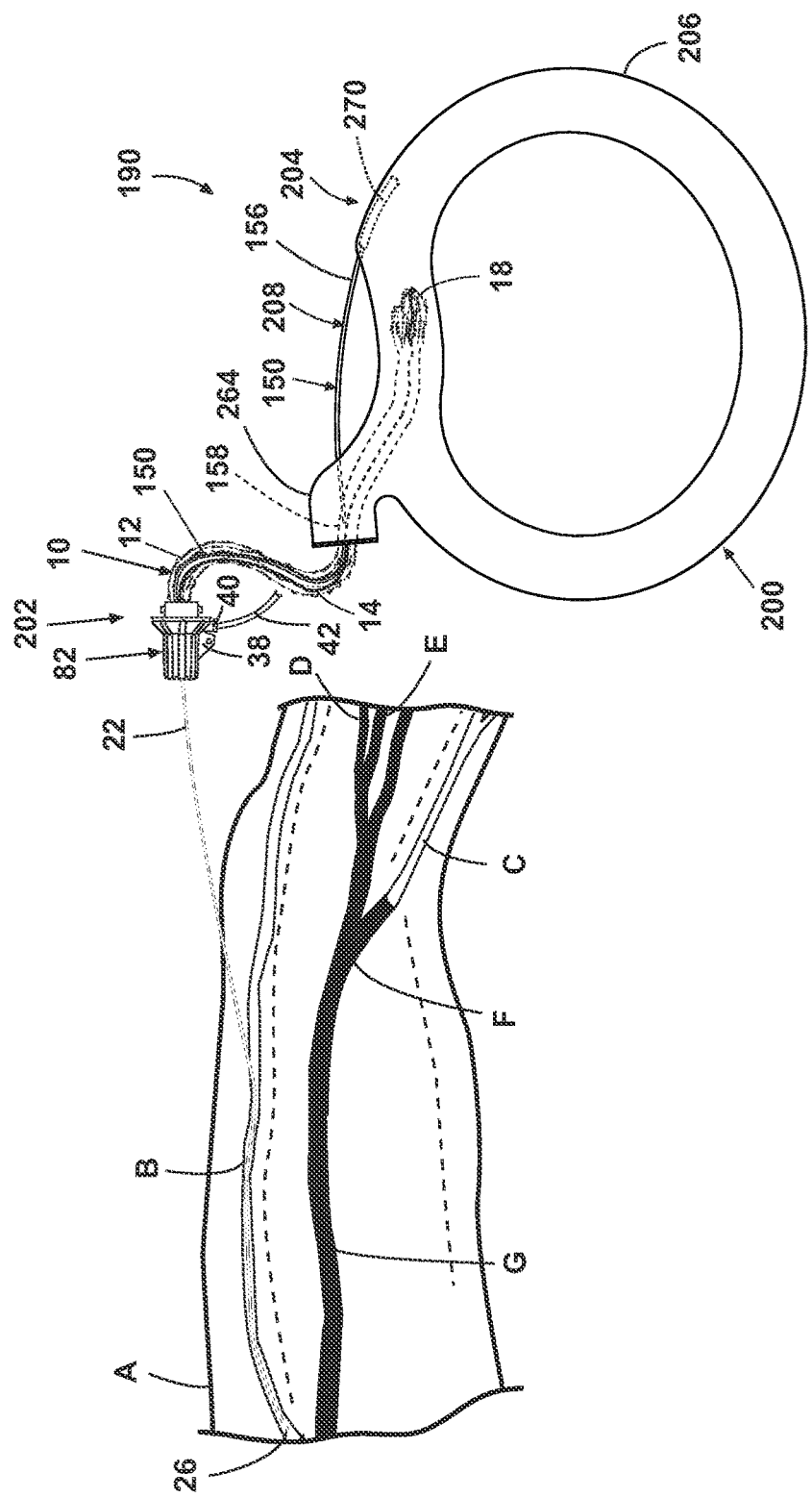
FIG. 40 is a view similar to FIG. 39 during removal of the apparatus from the distal coupler and the introducer sheath.
Figure 41:
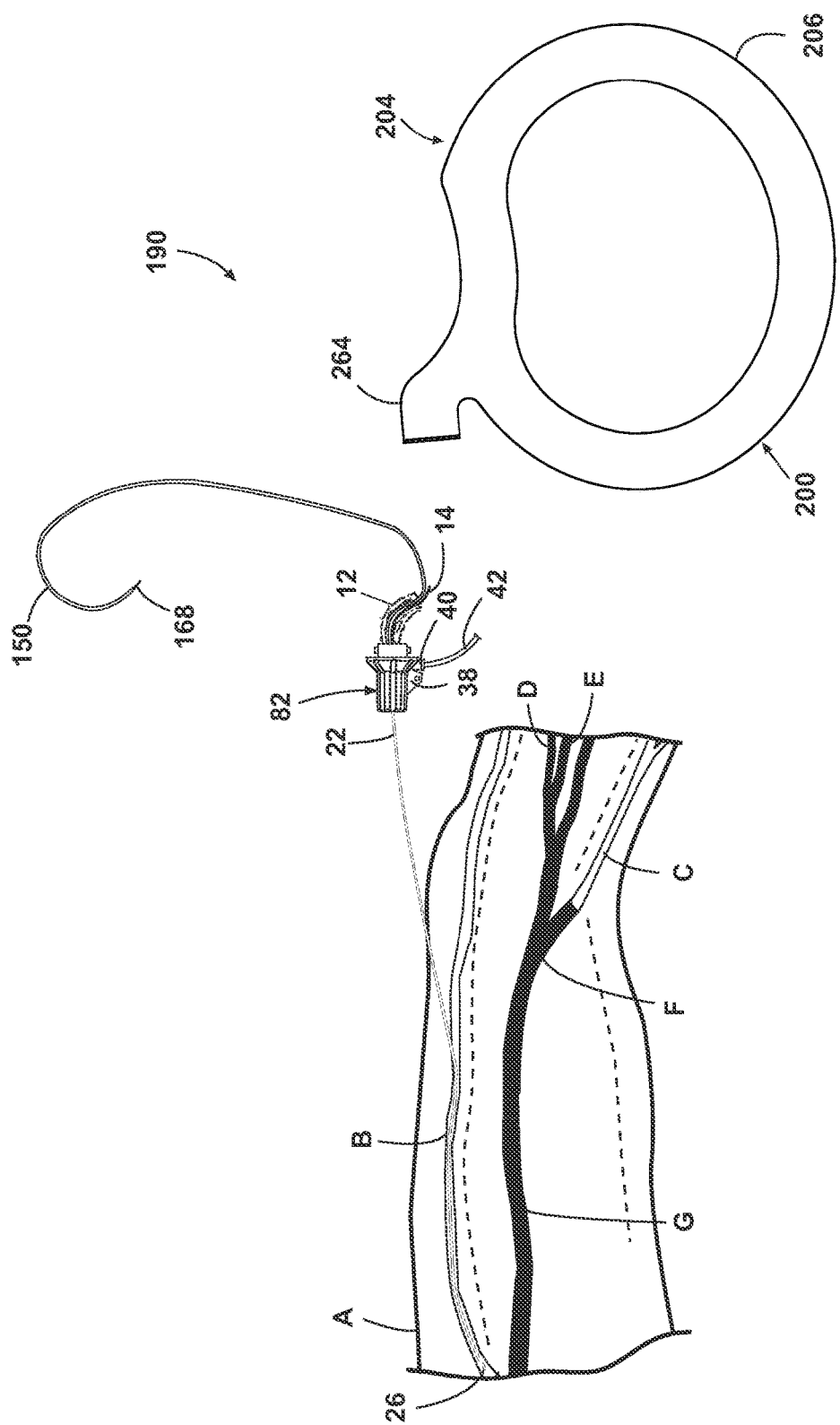
FIG. 41 is a view similar to FIG. 40 after removal of the apparatus from the distal coupler and the introducer sheath and trimming of the implant.

In one embodiment of a method of use of the system 190, various stages of which are depicted in FIGS. 39-41, the target HAS (e.g., a vein such as the greater saphenous vein B) can first be accessed at an access site through the skin and the introducer sheath 20 is advanced to the desired implant location as described above for the system 46 with respect to FIGS. 15 and 15A. After advancement of the introducer sheath 20 to the desired implant location, the apparatus 200 is coupled to the introducer sheath 20 by first placing the distal coupler 82 onto the shaft 22 and thereafter attaching the proximal coupler 264 and, thereby, the remainder of the apparatus 200, to the distal coupler 82, as described above for FIGS. 15 and 16.

FIG. 39 illustrates the introducer sheath 20 with the apparatus 200 coupled thereto. Details of the proximal and distal couplers 264, 82 and the introducer sheath 20 in the coupled configuration are described above and shown in FIGS. 31 and 32. Notably, the proximal coupler exit opening 100 and the introducer sheath proximal opening 34 are aligned with each other to enable advancement of the pushrod 150 from the apparatus 200, through both openings 100, 34, and into the introducer sheath 20, as will be described in more detail below. In the depicted embodiment, the proximal coupler exit opening 100 and the introducer sheath proximal opening 34 are directly adjacent one another to effect the alignment, although other methods of aligning the openings 100, 34 are possible.

With the apparatus 200 coupled to the introducer sheath 20, as illustrated in FIG. 39, the apparatus 200 can be easily handled and manipulated by the practitioner due to various aspects of the apparatus 200. One exemplary contributing aspect is the casing 206 that stores both the implant 10 and the introducer assembly 208. Because the implant 10 and the introducer assembly 208 are commonly stored within a single casing, the apparatus 200 can be made more compact and may be easier the handle. Furthermore, because the casing 206 is shaped as a closed loop, and the implant 10 and introducer assembly 208 are at least partially stored within the closed loop, the apparatus can be made even more compact in comparison to the embodiment of the apparatus 50 above that stores the implant in a straight tube 60. Another exemplary contributing aspect is the saddle-like portion 262 of the casing 206. The offset between the exposed portion 156 of the pushrod 150 and the saddle-like portion 262 allows the practitioner to grip the pushrod 150 closer to its distal tip region 158 where the pushrod is coupled to the implant 10.

The apparatus 200 in this state is ready for introduction of the implant 10 into the vein B. The practitioner grasps the exposed portion 156 of the pushrod 150 and moves the pushrod 150 distally from the storage position (see FIGS. 31 and 32) to and distal of the advancing position (see FIGS. 37 and 38) by applying a proximal force to the pushrod, as illustrated by the arrow L in FIG. 37, thereby advancing the pushrod 150 and the implant 10 through the coupler assembly 202. In particular, as depicted in FIGS. 37 and 38, the pushrod 150 and the implant 10 (not shown for clarity) move distally through the channel 98 and the exit orifice 100 of the proximal coupler 264 to enter the introducer sheath 20 at the proximal opening 34. The introducer guide 94 directs the pushrod 150 toward the channel 98 if the pushrod 150 diverges from axial alignment with the channel 98 prior to entering the channel 98. After entering the proximal opening 34, the pushrod 150 and the implant 10 continue their advancement through the hub 28 and into the lumen 24 of the shaft 22.

As the pushrod 150 advances the implant 10 through the proximal coupler 264, the body 12 of the implant 10 changes conditions from its expanded condition to a compressed condition as a result of the relatively small cross-sectional diameter of the channel 98 and exit opening 100; the channel 98 effectively forces the implant body 12 to compress in order to pass therethrough. The introducer guide 94 also facilitates the compression of the implant body 12 as it approaches the channel 98 by gradually reducing the cross-sectional diameter of the implant body 12. Lengthening of the implant body 12 can accompany the compression. Because the proximal opening 34, the hub 28, and the shaft lumen 24 of the introducer sheath 20 preferably have a cross-sectional diameter about equal to that of the channel 98 and the exit opening 100, the implant body 12 retains substantially in the same compressed condition as it moves through the introducer sheath 20.

The pushrod 150 and the implant 10 cease advancement when reaching the desired implant location, which is just below the sapheno-femoral junction H, as illustrated in FIG. 18. After the pushrod 150 and the implant 10 are advanced to the desired implant location, the practitioner disconnects the proximal coupler 264 from the distal coupler 82 and pulls the implant storage/introducer unit 204 and the proximal coupler 264 proximally away from the introducer sheath 20 by a suitable distance, as illustrated in FIG. 40. During the decoupling of the coupler assembly 202 and retraction of the implant storage/introducer unit 204, the pushrod 150 and the implant 10 remain in the position shown in FIG. 18 in the vein B; thus, the housing 270 moves proximally along the pushrod 150, thereby exposing a greater length of the pushrod 150. The distance between the introducer sheath 20 and the implant storage/introducer unit 204 shown in FIG. 40 can be selected to expose a predetermined length of the implant 10 between the introducer sheath 20 and the implant storage/introducer unit 204. In one embodiment, the practitioner pulls the implant storage/introducer unit 204 and the proximal coupler to expose about 10-50 cm of the implant 10. The practitioner then trims the implant body 12 and the tether 14 at the exposed portion. After trimming the implant 10, the practitioner continues to pull the implant storage/introducer unit 204 and the proximal coupler 264 proximally away from the introducer sheath 20 to fully uncoil and expose the pushrod 150 and separate the pushrod 150 and the implant 10 from the remainder of the apparatus 200. FIG. 41 illustrates the introducer sheath 20, the pushrod 150, and the implant 10 in the leg A after removal of the implant storage/introducer unit 204.

The remaining steps in the method of use of the system 190 are similar to the final steps of the method of use of the system 46. Removal of the introducer sheath 20 follows removal of the implant storage/introducer unit 204, described for and illustrated in FIG. 21 which illustrates the pushrod 150 and the implant 10 in the greater saphenous vein B after removal of the introducer sheath 20. With the pushrod 150 and the implant 10 in the vein B, the practitioner releases the implant 10 from the pushrod 150, as described for and illustrated in FIG. 22, which illustrates the implant 10 released from between the wire 168 and the pushrod 150. The practitioner follows release of the implant 10 with retraction of the pushrod 150 from the vein B, as described for and illustrated in FIG. 23 which illustrates the implant 10 in the greater saphenous vein B after removal of the pushrod 150. The practitioner can optionally secure the implant 10 to the leg A following removal of the pushrod 150 described for and illustrated in FIGS. 24 and 24A.

During the storage and introduction of the implant 10, the implant body 12 assumes multiple conditions with respect to the expansion and compression of the implant body 12. The implant body 12 in the illustrated embodiment assumes an expanded condition when in the implant storage/introducer unit 204 of the apparatus 200 during storage (i.e., a storage condition), as best seen in FIGS. 35 and 36. A first compressed condition when in the shaft 22 of the introducer sheath 20 during introduction (i.e., an introduction condition) is shown in FIG. 25B, and, assuming the HAS has a differing cross-sectional diameter than the shaft 22, a second compressed condition when in the HAS, shown as the greater saphenous vein B for illustrative purposes, after implantation (i.e., an implantation condition), as shown in FIG. 25C. The implant body 12 also undergoes transitional conditions when converting between the storage, introduction, and implantation conditions. These conditions are imposed on the implant body 12 because of the cross-sectional diameter of the structure that houses the implant body 12; once the housing structure cross-sectional diameter is sufficient to cause compression of the implant body 12, compression of the implant body 12 increases as the housing structure cross-sectional diameter decreases. The housing structures corresponding to the storage, introduction, and implantation conditions of the illustrated embodiment are, respectively, the cavity 252 of the implant storage/introducer unit 204, the shaft 22 of the introducer sheath 20, and the HAS, in this case, the greater saphenous vein B.

The order of the steps described above for the method of use of the system 190 can be performed in any desired and suitable order and are not intended to be limited to the order the steps are described above. For example, the retraction of the pushrod 150 and the introducer sheath 20 can occur in any desired order, i.e., the pushrod 150 first, the introducer sheath 20 first, or the pushrod 150 and introducer sheath 20 simultaneously.

The method can be used with the illustrated apparatus 200, other embodiments of the illustrated apparatus 200, or other types of apparatuses for storage and/or introduction of the implant 10 or other suitable implant. Similarly, the apparatus 200 can be employed with the illustrated implant 10, other embodiments of the illustrated implant 10, or other types of occluding implants. The case is the same with respect to the use of the introducer sheath 20 with the apparatus 200.

The apparatus 200 can be provided as a ready-to-use kit having the implant 10 disposed in the implant storage/introducer unit 204 and connected to the pushrod 150 such that the apparatus 200 can be removed from its packaging for immediate surgical use. In one embodiment, the kit includes only the apparatus 200; alternatively, the kit can optionally include the introducer sheath 20 such that the entire system 190 is provided as a ready-to-use kit. In one embodiment, the apparatus 200 can be a single use device that is disposed after surgical use. Alternatively, the apparatus 200 can be a multiple use device that can be sterilized and provided with a new implant 10 and, if necessary, a new pushrod 150 having a new wire 168, for each surgical use.

One problem that has been observed with some occluding implants, such as implant 10 of FIG. 2, is blood leakage around or through the implant near the sapheno-femoral junction H (see FIG. 1). This may be a result of the blood flow at the sapheno-femoral junction H pushing the implant to one side of the vein and allowing blood to flow past the implant, and/or from insufficient bulk or packing density of the implant, which can allow blood to flow between the fibers of the implant itself. Blood leakage may be prevented or at least reduced by using the manipulation technique of withdrawing the pushrod 150 after placement in the vein B but prior to releasing the implant 10, as described above with respect to FIGS. 21 and 22, to shorten the implant, increase the packing density of implant material, radially expand the implant, and/or increase the radially outward force exerted by the implant body on the inner wall of the HAS or vein near the sapheno-femoral junction H while reducing longitudinal tension in the portion of the implant positioned in the saphenous vein.

FIGS. 42-57 illustrate alternate embodiments of implants that can effectively prevent or at least reduce the potential for blood leakage around or through the implant without requiring manipulation of a pushrod. Rather, the implants can be augmented to locally bulk the implant, shorten the implant, increase the packing density of implant material, radially expand the implant, and/or increase the radially outward force exerted by the implant body on the inner wall of the HAS or vein near the sapheno-femoral junction H.

Figure 42:
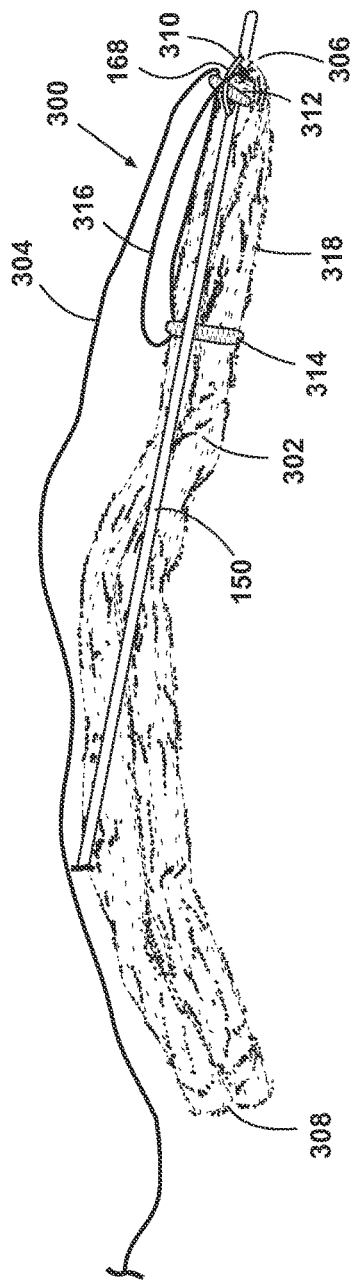
FIG. 42 is an elevation view of another embodiment of an implant for occluding a hollow anatomical structure, such as a vein in the venous systems shown in FIG. 1, showing the implant in an unaugmented configuration.

FIG. 42 illustrates one embodiment of an implant 300 for occlusion of a hollow anatomic structure that can effectively prevent or at least reduce the potential for blood leakage around or through an implant without requiring manipulation of a pushrod. The implant 300 can be employed in place of implant 10 of FIG. 2 in the system 45 of FIG. 4, the system 190 of FIG. 26, or any other suitable system. The implant 300 can be similar in structure, function, and method of use to the implant 10, except as further described herein. The depicted implant 300 comprises a bioresorbable body 302. The body 302 can comprise a bioresorbable material in fibrous form that can be similar or identical to the material and construction of the body 12 of implant 10, and will therefore not be further described for this embodiment. For example, as shown in the illustrated embodiment, the body 302 can naturally assume an expanded condition and convert to a compressed condition upon application of a compressive force or upon placement in a confined space such as a blood vessel lumen. Alternatively, the body 302 can naturally assume a compressed condition and convert to an expanded condition upon application of an expansive force.

The implant 300 further includes a tether 304 coupled to the body 302. As one example, the body 302 can be generally elongated with a distal end 306 and a proximal end 308, the distance between the distal end 306 and the proximal end 308 (i.e., the length of the body 302) optionally being greater than the cross-sectional diameter of the body 302, and the tether 304 is coupled near or to the distal end 306 of the body 302. The tether 304 can be coupled to the body 302 in any suitable manner, examples of which include tying or stitching the tether 304 to the body 302, employing a coupling agent, such as a bioresorbable or non-bioresorbable adhesive, and making the tether 304 integral with the body 302. In the embodiment of FIG. 42, the tether 304 is coupled to the body 302 by tying the tether 304 around the body 302 near a center of the length of the body 302, and the body 302 is bent or turned where the tether 304 is coupled to the body 302 such that the body 302 is folded upon itself. As a result of this configuration, the coupling location of the tether 304, or the tie point 310, generally forms the distal end 306 of the body 302, and the free ends of the body 302 folded upon each other form the proximal end 308 of the body 302. The tether 304 can have any suitable length relative to the length of the body 302. For example, the length of the tether 304 can be greater than, equal to, or less than that of the body 302. The material and construction of tether 304 can be similar or identical to the material and construction of the tether 14 of implant 10, and will therefore not be further described for this embodiment.

The implant 300 can further include force application points coupled to the body 302 and interacting with the tether 304 to apply force to the body 302 when force is applied to the tether 304. One example of a force application point is a band coupled to and encircling the body 302. In the embodiment of FIG. 42, the implant 300 includes multiple spaced bands in the form of a distal tack 312 and a proximal tack 314 coupled to the body 302. The tacks 312, 314 can be coupled to the body 302 in any suitable manner, examples of which include tying or stitching the tacks 312, 314 to the body 302, employing a coupling agent, such as a bioresorbable or non-bioresorbable adhesive, and making the tacks 312, 314 integral with the body 302. In the embodiment of FIG. 42, the tacks 312, 314 are coupled to the body 302 by tying; both tacks 312, 314 are tied around the body 302 near the distal end 306, with the distal tack 312 being closer to the distal end 306 than the proximal tack 314.

Each tack 312, 314 can be bioresorbable and made of the same material as the body 302 or of a material different than that of the body 302. Alternatively, the tacks 312, 314 can be non-bioresorbable. Further, the tacks 312, 314 can be inelastic or elastic. In the illustrated embodiment of FIG. 42, the tacks 312, 314 comprise a loop or ring of bioresorbable thread tied around the body 302. Each tack 312, 314 can be looped around the body 302 one or more times. Preferably, the tacks 312, 314 are fixed and immovable relative to the fibers of the implant body 302. In other words, the tacks 312, 314 preferably cannot "slip" or slide along the fibers of the body 302 when forces are applied to the tacks 312, 314. However, as discussed in further detail below, the tacks 312, 314 preferably can move relative to each other or relative to the distal end 306 as the body 302 compresses (or bunches) longitudinally, or elongates.

The pushrod 150 can facilitate the bulking/augmentation of the implant 300 by holding the distal tack 312 via the wire 168. As illustrated, the distal tack 312 can encircle the pushrod 150 beneath the wire 168 such that the implant retaining portion 170 (FIG. 11) attaches the distal tack 312 to the pushrod 150. Alternatively, the distal tack 312 can encircle just the wire 168 for a similar effect. In either configuration, detachment of the wire 168 from the distal plug 166 and its subsequent retraction through openings 160, 162 (see FIG. 11) is uninhibited by the distal tack 312.

In the embodiment of FIG. 42, the portion of the tether 304 extending from the tie point 310 sequentially extends generally proximally from the tie point 310, through the proximal tack 314, thus reversing direction and extending generally distally back toward the distal end 306, through the distal tack 312, reversing direction once again and extending generally proximally from the distal tack 312 along the body 302. As a result of this configuration, the tether 304 forms a loop 316 that is adjustably-sized. Applying a proximal force to the tether 304, such as by pulling the tether 304, reduces the size of the loop 316 and moves the tacks 312, 314 toward each other.

The tacks 312, 314 and loop 316 create an augmentation zone 318, which is an area of the body 302 generally between the tacks 312, 314 that can selectively be augmented in order to locally increase the radial size and/or material density of the body 302, or shorten the implant, increase the packing density of implant material, radially expand the implant, or increase the radially outward force exerted by the implant body on the inner wall of the HAS or vein in the zone 318. The augmentation zone 318 is selectively configurable in an unaugmented configuration, shown in FIG. 42, and an augmented configuration, shown in FIG. 43. In the unaugmented configuration, the augmentation zone 318 can have dimensions (e.g. radial size) and/or material density generally similar to the rest of the body 302. In the augmented configuration, the augmentation zone 318 can have increased cross-sectional area and/or material density, while exerting a larger radially outward force against the inner walls of the HAS in comparison with the rest of the body 302. In the example shown in FIG. 43, the body 302 in the augmentation zone 318 has both increased cross-sectional area and density in the augmented configuration. The distance between the distal tack 312 and the proximal tack 314 can directly relate to the degree of localized augmentation possible for the implant 300. A smaller distance between the tacks 312, 314 results in less localized augmentation, while a greater distance between the tacks 312, 314 results in more localized augmentation.

Figure 43:
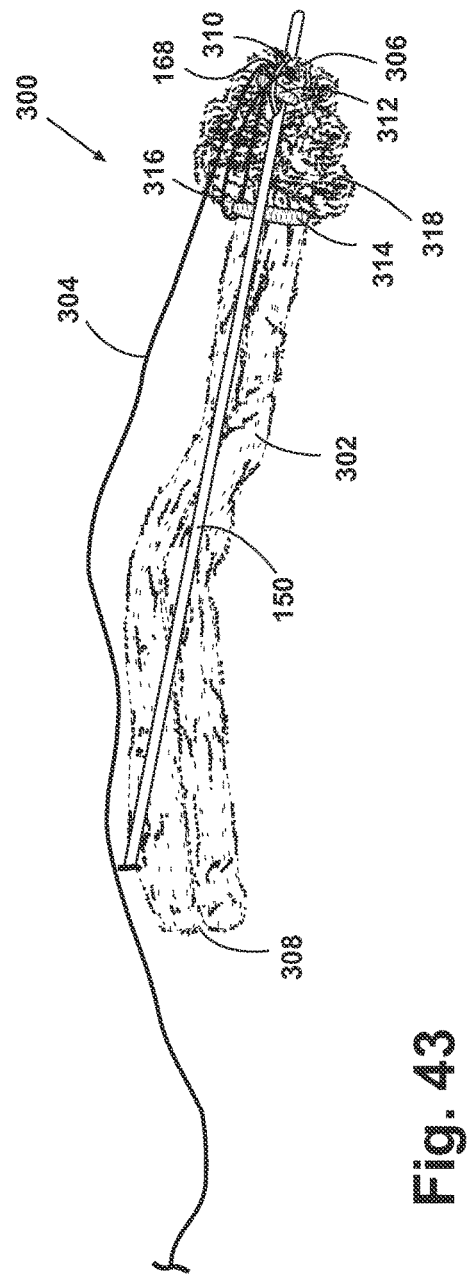
FIG. 43 is an elevation view of similar to FIG. 42, showing the implant in an augmented configuration.

The tether 304 acts as an actuator for the augmentation zone 318 and can be used to selectively configure the augmentation zone 318 in the augmented configuration. Specifically, pulling the tether 304 proximally reduces the size of the loop 316, which causes the proximal tack 314 to move relative to the distal tack 312 such that the distance between the tacks 312, 314 is reduced. This causes the body 302 to locally "bulk up" by increasing in cross-sectional area and/or density of the body 302 in the augmentation zone 318, as illustrated in FIG. 43. Pulling the tether 304 can cause the proximal tack 314 to move distally, while the distal tack 312 stays relatively stationary due to its coupling with the pushrod 150. Alternately, if the distal tack 312 is not coupled with the pushrod 150, pulling the tether 304 can cause the distal tack 312 to move proximally, while the proximal tack 314 stays relatively stationary. In many cases, the former may be preferred, since the localized bulking or augmentation of the body 302 can be maintained closer to the sapheno-femoral junction H.

The pushrod 150 can further facilitate the bulking/augmentation of the implant 300 by holding the distal portion or end 306 of the implant 300, in addition to or instead of holding the distal tack 312, via the wire 168. The pushrod 150 and wire 168 thus prevent proximal movement of the distal portion or end 306 of the implant 300 as the tether 304 is pulled proximally. Thus, rather than simply moving the entire implant 300 proximally, the proximal pulling of the tether 304 takes up the "slack" in the tether forming the loop 316, resulting in augmentation of the body 302.

In various embodiments, the practitioner can grip the pushrod 150 (e.g., a portion proximal of the zone 318), to prevent proximal movement of the pushrod 150 and implant 300, while pulling the tether 304 proximally. Alternatively, the practitioner can push the pushrod 150 slightly in the distal direction while pulling the tether 304, or rely on non-manual means such as a clamp, or the inertia of and friction in the delivery system (e.g. the system 46/190), to prevent proximal movement of the implant 300 and pushrod 150 while pulling the tether 304 proximally to augment the implant 300. Alternatively, instead of being manually gripped by the practitioner, any of the above can be accomplished by a motorized or non-motorized drive system, gear train, mechanism, etc. that grips or engages the pushrod 150 and is operated by the practitioner.

One embodiment of a method of using of the implant 300 is described below. While the implant 300 can be employed in conjunction with any suitable HAS, the methods are described with respect to the greater saphenous vein B for illustrative purposes. It will be understood that the methods can be modified or adapted as necessary, if necessary, for use in other HASs. It will also be understood that while the implant 300 is described for use with the system 46, the methods can also be modified or adapted, as necessary, for use with embodiments of the system 46 other than the embodiment employed in the following description. Aspects of the method of use of the implant 300 that overlap with the method of use of the implant 10, described above, will be briefly summarized, but will not be described in detail. Generally, the method of use of the implant 300 can be similar to the use of the implant 10, except as further described herein. In the description of the method, the various steps are discussed in terms of being performed by the practitioner; however, it is understood that these steps may be performed by the practitioner manually or through the operation of a motorized or non-motorized drive system, etc.

In one embodiment of a method of use of the implant 300, the various stages of the method proceed as depicted for implant 10 as shown in FIGS. 15-22. Release of the implant 300 from the pushrod 150 proceeds generally as described above for implant 10 with respect to FIGS. 21 and 22, with the added step that the pushrod 150 slides through and out of the distal tack 312 as it is withdrawn. The distal tack 312 can encircle the pushrod 150 with sufficient clearance to allow the pushrod 150 to slide out of the distal tack 312 as it is retracted from the vein B.

Figure 44:
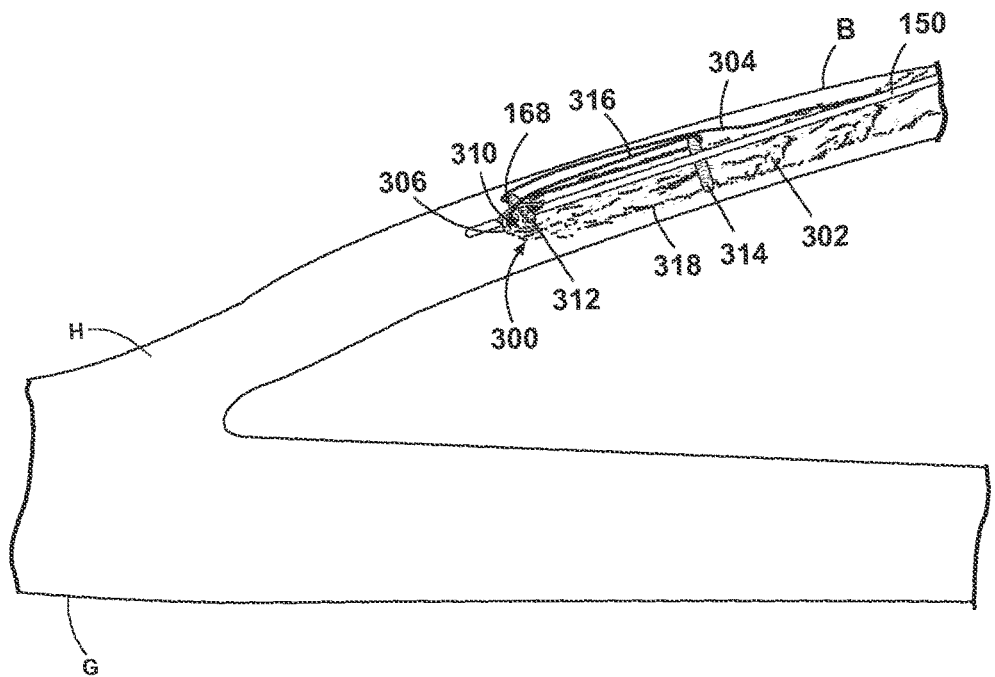
FIG. 44 illustrates the leg of FIG. 1 and the implant of FIG. 42 located in the greater saphenous vein, with the implant in the unaugmented configuration.
Figure 45:
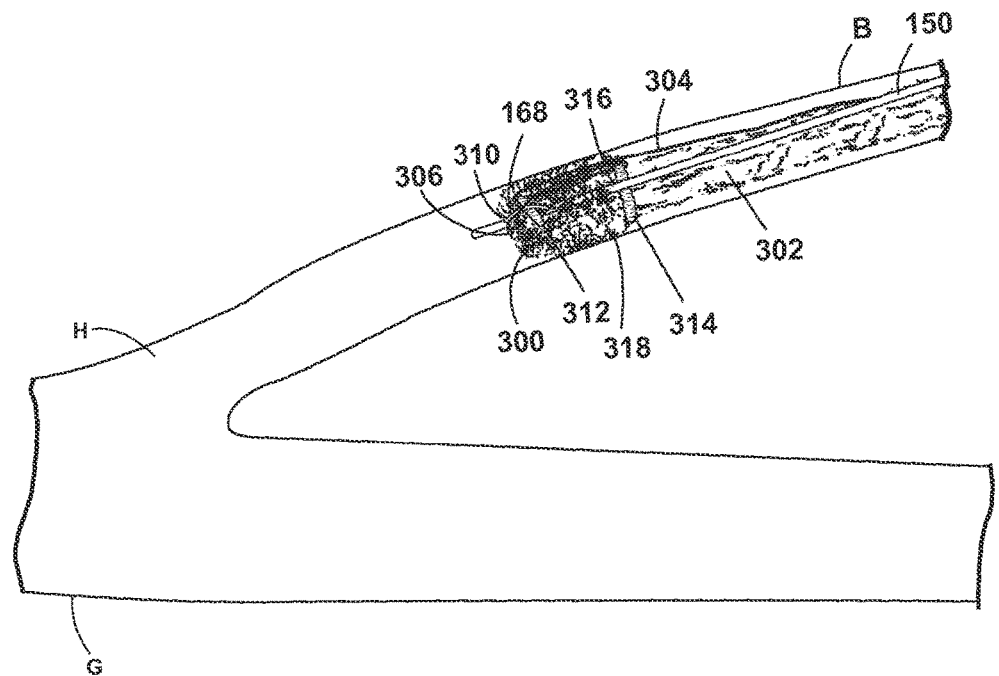
FIG. 45 is a view similar to FIG. 44 illustrating the implant in the augmented configuration.

FIG. 44 illustrates the implant 300 in the greater saphenous vein B before release of the implant 300 and removal of the pushrod 150 from the vein B. Initially, the augmentation zone 318 is in the unaugmented configuration, as shown in FIG. 44. The practitioner then applies a proximal force to the tether 304, such as by pulling on the proximal end of the tether 304, thereby reducing the size of the loop 316 and moving the distal and proximal tacks 312, 314 relative to each other such that the distance between the tacks 312, 314 is reduced. The pushrod 150 and wire 168, assisted by any force applied thereto or anchoring of a proximal portion of the pushrod, prevent proximal movement of the implant 10 as the proximal force 314 is applied to the tether 304. The pulling and loop-reduction action places the augmentation zone 318 in the augmented configuration, as shown in FIG. 45. With the augmentation zone 318 in the augmented configuration as shown in FIG. 45, the implant 300 prevents or at least reduces the potential for blood leakage around or through the implant 300 by locally bulking or augmenting the body 302 (e.g., radially expanding the body, increasing the density of material in the body, and/or increasing the radially outward force exerted by the body on the inner wall of the HAS or vein) within the vein B near the saphenofemoral junction H. The practitioner can then optionally secure the implant 300 to the leg A, as described above with respect to FIGS. 24 and 24A.

Figure 46:
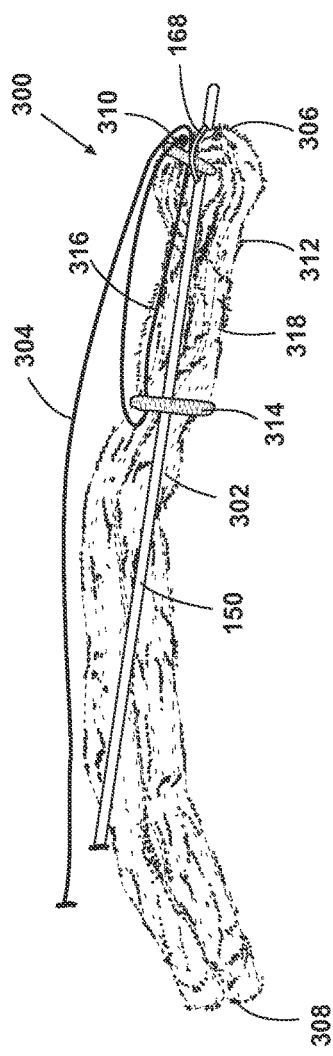
FIG. 46 is an elevation view of another embodiment of an implant for occluding a hollow anatomical structure, such as a vein in the venous systems shown in FIG. 1, showing the implant in an unaugmented configuration.

FIG. 46 depicts another embodiment of an implant 300 which can be similar in structure, function and method of use to the implant 300 of FIGS. 42-45, except as further described herein. As illustrated, the proximal tack 314 encircles the pushrod 150 as well as the body 302. Therefore, the proximal tack 314 can cooperate with the distal tack 312 to hold the body 302 against the pushrod 150. Detachment of the wire 168 from the distal plug 166 and its subsequent retraction through openings 160, 162 (see FIG. 11) is uninhibited by the tacks 312, 314. Release of the implant 300 from the pushrod 150 proceeds generally as described above for implant 10 with respect to FIGS. 21 and 22, with the added step that the pushrod 150 slides through and out of the tacks 312, 314 as it is withdrawn. The tacks 312, 314 can encircle the pushrod 150 with sufficient clearance to allow the pushrod 150 to slide out of the tacks 312, 314 as it is retracted from the vein B.

Figure 47:
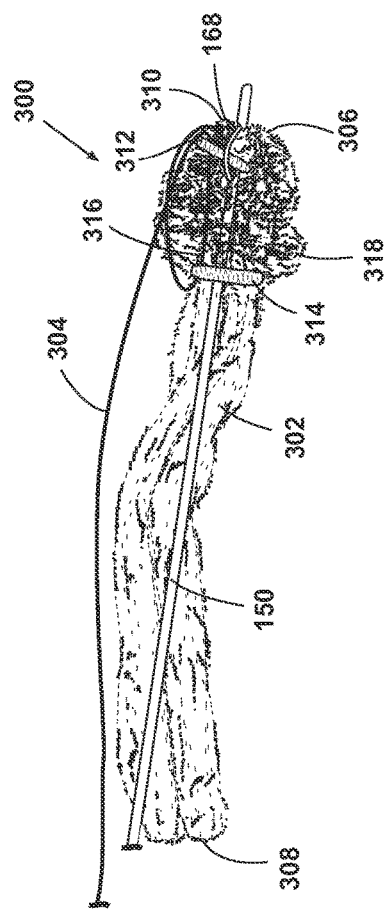
FIG. 47 is an elevation view of similar to FIG. 46, showing the implant in an augmented configuration.

The augmentation zone 318 can be actuated before the release of the implant 300 from the pushrod 150, as shown in FIG. 47, thereby placing the augmentation zone 318 in the augmented configuration. Applying a proximal force to the tether 304, such as by pulling, reduces the size of the loop 316, which causes the tacks 312, 314 to move relative to each other such that the distance between the tacks 312, 314 is reduced. At this time, the proximal tack 314 will also move relative to the pushrod 150, such as by sliding along the pushrod 150. Otherwise, the process can proceed generally as described above for the embodiment shown in FIGS. 42-45.

Figure 48:
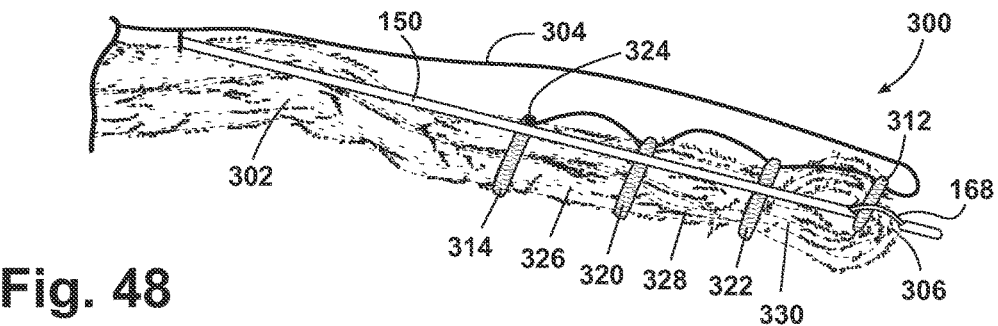
FIG. 48 is an elevation view of another embodiment of an implant for occluding a hollow anatomical structure, such as a vein in the venous systems shown in FIG. 1, showing the implant in an augmented configuration.

FIG. 48 depicts another embodiment of an implant 300 which can be similar in structure, function and method of use to the implant 300 of FIGS. 42-45, except as further described herein. The implant 300 includes at least one intermediate tack between the distal and proximal tacks 312, 314. As illustrated, implant 300 includes a first intermediate tack 320 and a second intermediate tack 322, with the second intermediate tack 322 adjacent to and spaced proximally from the distal tack 312, the first intermediate tack 320 adjacent to and spaced proximally from the second intermediate tack 322, and the proximal tack 314 adjacent to and spaced proximally from the first intermediate tack 320.

In this embodiment, the distal end 306 is at or near the coupling location of the distal tack 312 rather than the tie point of the tether 304. The distal tack 312 is coupled to the body 302 near a center of the length of the body 302, and the body 302 is bent or turned where the distal tack 312 is coupled to the body 302 such that the body 302 is folded upon itself. As a result of this configuration, the coupling location of the distal tack 312 forms the distal end 306 of the body 302, and the free ends of the body 302 folded upon each other form the proximal end 308 of the body 302.

The tether 304 is coupled to the proximal tack 314 at a tie point 324 and looped through the remaining tacks 312, 320, 322 to create three distinct augmentation zones; a first augmentation zone 326 generally between the proximal tack 314 and the first intermediate tack 320, a second augmentation zone 328 generally between the first and second intermediate tacks 320, 322, and a third augmentation zone 330 generally between the second intermediate tack 322 and the distal tack 312. The portion of the tether 304 extending from the tie point 324 extends generally distally from the proximal tack 314, sequentially through the first intermediate tack 320, the second intermediate tack 322, and the distal tack 312, and then generally proximally from the distal tack 312 along the body 302. As a result of this configuration, the tether 304 does not form a loop, but rather has an adjustable length between the tie point 324 and the distal tack 312. Applying a proximal force to the tether 304, such as by pulling the tether 304, reduces the length of the tether between the tie point 342 and the distal tack 312.

Figure 49:
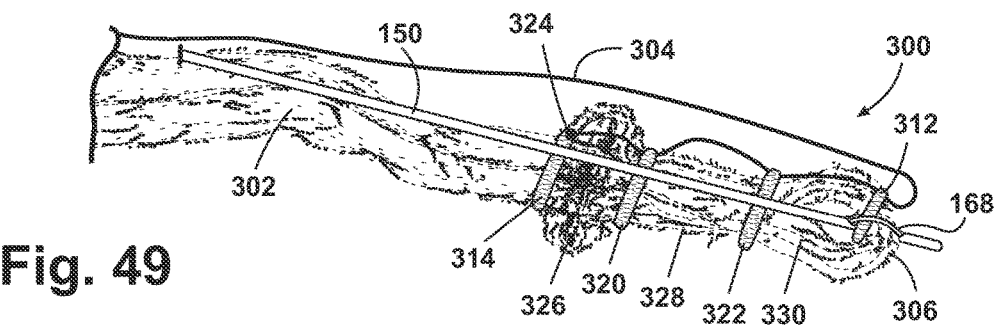
FIG. 49 is an elevation view of similar to FIG. 48, showing a first augmentation zone in an augmented configuration.
Figure 50:
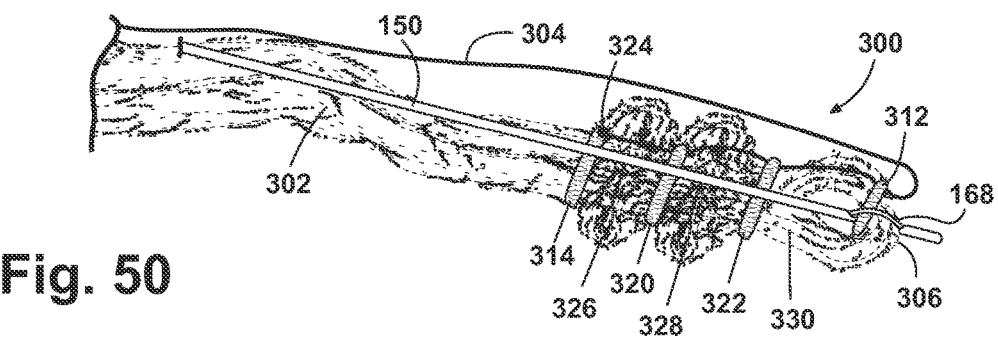
FIG. 50 is an elevation view of similar to FIG. 49, showing a second augmentation zone in an augmented configuration.
Figure 51:
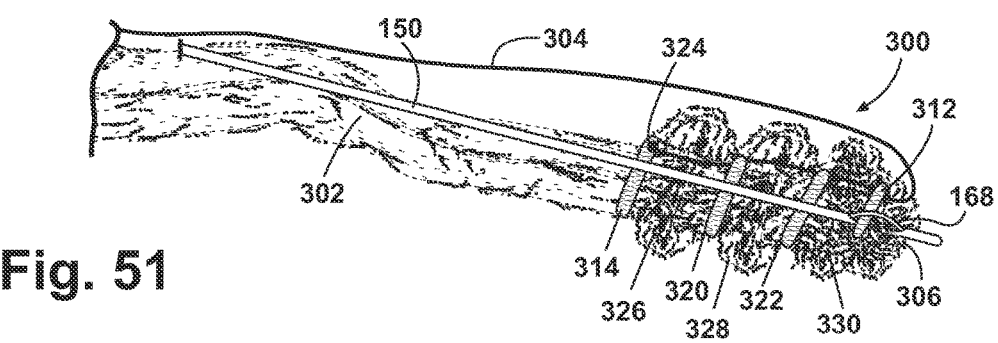
FIG. 51 is an elevation view of similar to FIG. 50, showing a third augmentation zone in an augmented configuration.

Each augmentation zone 326, 328, 330 is configurable in an unaugmented configuration, shown in FIG. 48, and an augmented configuration, shown variously in FIGS. 49-51. The tether 304 acts as an actuator for all three augmentation zones. As illustrated in FIG. 49, pulling the tether 304 initially causes at least the proximal tack 314 and the first intermediate tack 320 to move relative to each other; for example, the proximal tack 314 can be pulled distally toward the first intermediate tack 320. This action places the first augmentation zone 326 in the augmented configuration. As illustrated in FIG. 50, continued pulling of the tether 304 causes at least the first and second intermediate tacks 320, 322 to move relative to each other; for example, the first intermediate tack 320 can be pulled distally toward the second intermediate tack 322. This action places the second augmentation zone 328 in the augmented configuration. As illustrated in FIG. 51, continued pulling of the tether 304 causes at least the second intermediate tack 322 and distal tack 312 to move relative to each other; for example, the second intermediate tack 322 can be pulled distally toward the distal tack 312. This action places the third augmentation zone 330 in the augmented configuration.

While the drawings show the sequential actuation of the augmentation zones 326, 328, 330, it will be understood from the drawings and the description that there may be some overlap between the actuation of the augmentation zones, and that the augmentation zones may be actuated generally simultaneously with each other. Furthermore, less than all of the augmentation zones can be actuated by exerting less pulling action on the tether 304. For example by only pulling the tether 304 a short distance, the first augmentation zone 326 may be actuated, but not the second or third augmentation zones 328, 330. Further, while three augmentation zones are illustrated in the drawings, any number of zones can be provided by including additional tacks on the body 302 and following the tethering pattern shown in the figures.

In addition to the embodiment having multiple augmentation zones shown in FIGS. 48-51, the arrangement depicted (wherein the tether 304 is fixed to the proximal tack 314, extends distally and passes through the distal tack 312 coupled to the distal end of the implant body 302 before extending proximally along the body 302) can be employed in an implant 300 having a single augmentation zone, between the distal and proximal tacks 312, 314.

The use of multiple augmentation zones, as seen in FIGS. 48-57, advantageously facilitates the formation of an augmented region of the implant which is greater in overall length than in a single-zone implant, while controlling the radial expansion of the implant and the shape of the augmentation zone when expanded. Instead of a relatively short zone of very wide radial expansion, a relatively long zone of moderate radial expansion can be formed.

Figure 52:
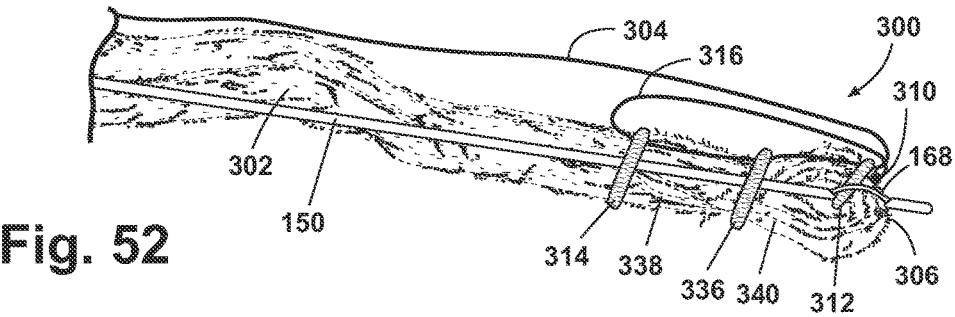
FIG. 52 is an elevation view of another embodiment of an implant for occluding a hollow anatomical structure, such as a vein in the venous systems shown in FIG. 1, showing the implant in an unaugmented configuration.

FIG. 52 depicts another embodiment of an implant 300 which can be similar in structure, function and method of use to the implants 300 of FIGS. 42-51, except as further described herein. The implant 300 includes at least one intermediate tack between the distal and proximal tacks 312, 314. As illustrated, implant 300 includes a single intermediate tack 336 between and spaced from the distal and proximal tacks 312, 314. Further, all of the tacks 312, 314, 336 are coupled to the pushrod 150 as well as the body 302, as described above with reference to FIG. 46.

The tether 304 is coupled to the body 302 at the distal tie point 310 and is looped through the tacks 312, 314, 336 to create two augmentation zones; a first augmentation zone 338 generally between the proximal tack 314 and the intermediate tack 336, and a second augmentation zone 340 generally between the intermediate tack 336 and the distal tack 312. The portion of the tether 304 extending from the tie point 310 sequentially extends generally proximally from the tie point 310, through the proximal tack 314, through the intermediate tack 336, through the distal tack 312, and generally proximally from the distal tack 312 along the body 302. As a result of this configuration, the tether 304 forms loop 316.

Figure 53:
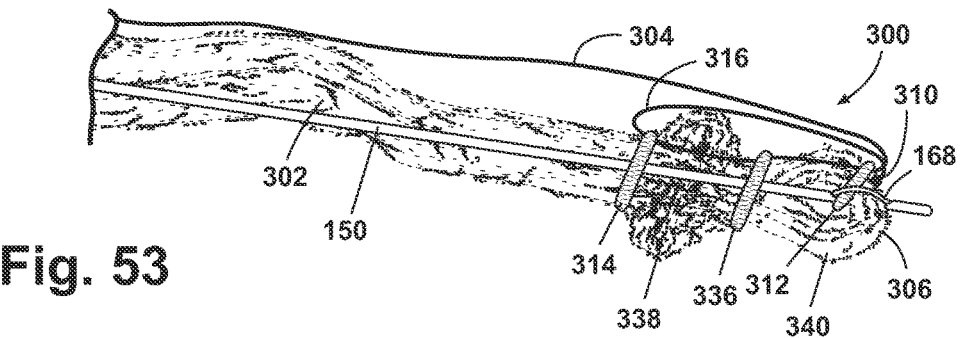
FIG. 53 is an elevation view of similar to FIG. 52, showing a first augmentation zone in an augmented configuration.
Figure 54:
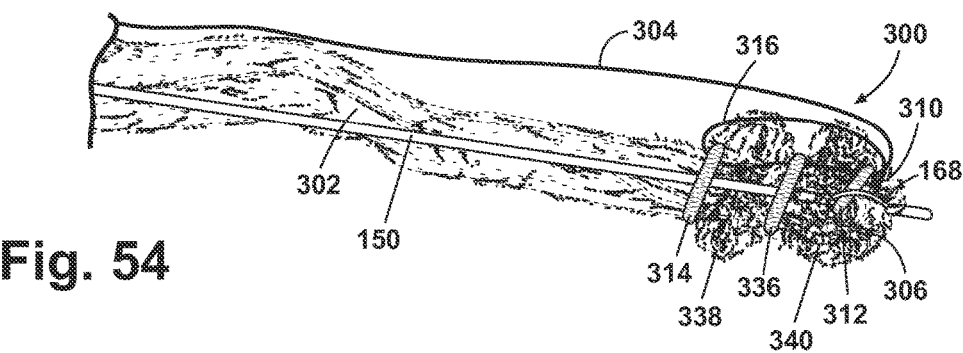
FIG. 54 is an elevation view of similar to FIG. 53, showing a second augmentation zone in an augmented configuration.

Each augmentation zone 338, 340 is configurable in an unaugmented configuration, shown in FIG. 52, and an augmented configuration, shown variously in FIGS. 53 and 54. The tether 304 acts as an actuator for both augmentation zones. As illustrated in FIG. 53, pulling the tether 304 initially begins to reduce the size of the loop 316, which causes at least the proximal tack 314 and the intermediate tack 336 to move relative to each other; for example, the proximal tack 314 can be pulled distally toward the intermediate tack 336. This action places the first augmentation zone 338 in the augmented configuration. At this time, at least one of the tacks 314, 336 will also move relative to the pushrod 150, such as by sliding along the pushrod 150. As illustrated in FIG. 54, continued pulling of the tether 304 further reduces the size of the loop, which causes at least the intermediate tack 336 and the distal tack 312 to move relative to each other; for example, the intermediate tack 336 can be pulled distally toward the distal tack 312. This action places the second augmentation zone 340 in the augmented configuration. At this time, the intermediate tack 336 will also move relative to the pushrod 150, such as by sliding along the pushrod 150.

While the drawings show the sequential actuation of the first and second augmentation zones 338, 340, it will be understood from the drawings and the description that there may be some overlap between the actuation of the augmentation zones, and that the augmentation zones may be actuated generally simultaneously with each other. Furthermore, less than all of the augmentation zones can be actuated by exerting less pulling action on the tether 304. For example by only pulling the tether 304 a short distance, the first augmentation zone 338 may be actuated, but not the second augmentation zone 340. Further, while two augmentation zones are illustrated in the drawings, any number of zones can be provided by including additional tacks on the body 302 and following the tethering pattern shown in the figures.

Figure 55:
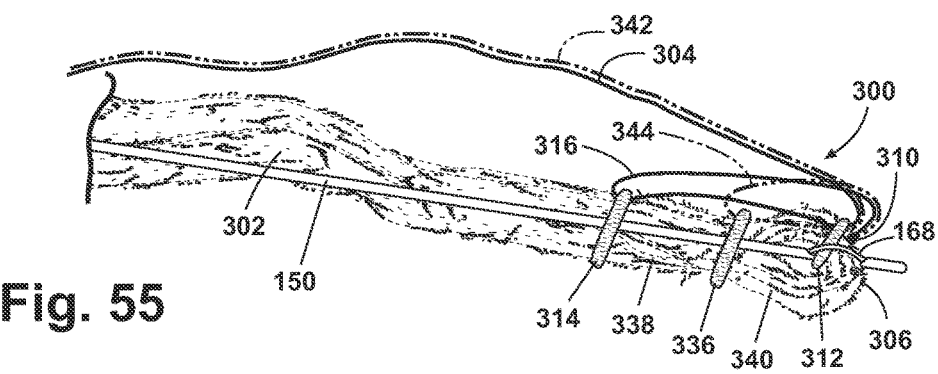
FIG. 55 is an elevation view of another embodiment of an implant for occluding a hollow anatomical structure, such as a vein in the venous systems shown in FIG. 1, showing the implant in an unaugmented configuration.
Figure 56:
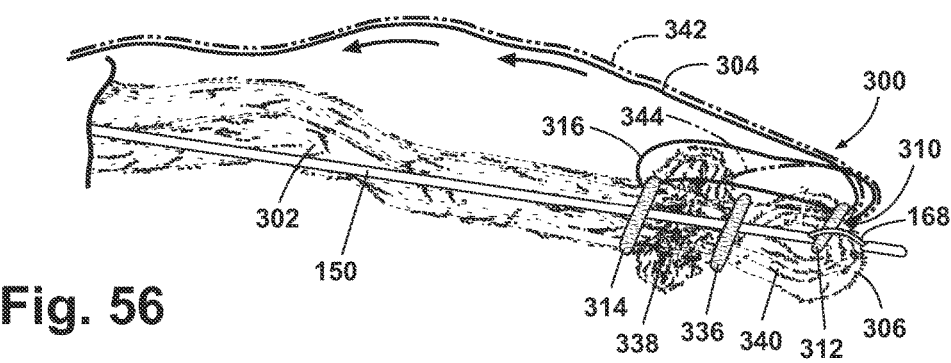
FIG. 56 is an elevation view of similar to FIG. 55, showing a first augmentation zone in an augmented configuration.
Figure 57:
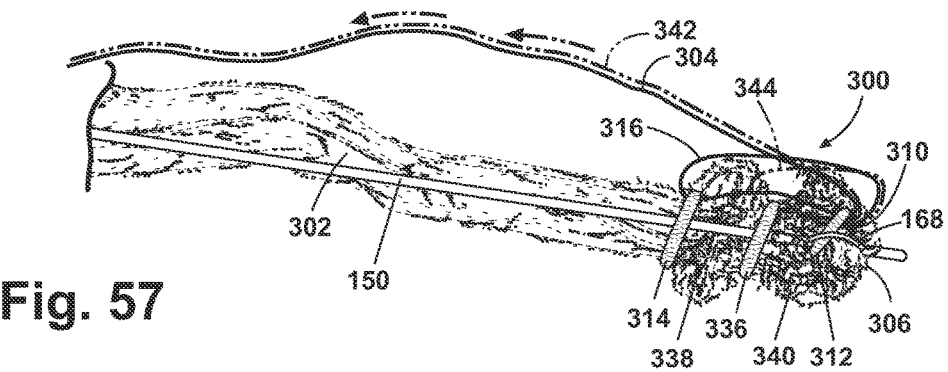
FIG. 57 is an elevation view of similar to FIG. 56, showing second augmentation zone in an augmented configuration.

FIG. 55 depicts another embodiment of an implant 300 which can be similar in structure, function and method of use to the implants 300 of FIGS. 42-54, except as further described herein. The implant 300 includes multiple tethers coupled to the body 302. As illustrated, the implant 300 includes two tethers 304, 342, each of which is coupled to the body 302 at the distal tie point 310. In FIGS. 55-57, the first tether 304 is drawn in solid line, while the second tether 342 is drawn in dotted line to help distinguish it from the first tether 304; however, the tethers 304, 342 can have the same structure and be made from the same material.

The tethers 304, 342 are looped through the tacks 312, 314, 336 to create the two augmentation zones 338, 340. The portion of the first tether 304 extending from the tie point 310 sequentially extends generally proximally from the tie point 310, through the proximal tack 314, generally distally back toward the distal end 306, through the distal tack 312, and generally proximally from the distal tack 312 along the body 302. As a result of this configuration, the first tether 304 forms a first loop 316 that is adjustably-sized. The portion of the second tether 342 extending from the tie point 310 sequentially extends generally proximally from the tie point 310, through the intermediate tack 336, generally distally back toward the distal end 306, through the distal tack 312, and generally proximally from the distal tack 312 along the body 302. As a result of this configuration, the second tether 342 forms a second loop 344 that is adjustably-sized. Pulling proximally on either tether 304, 342 reduces the size of the respective loop 316, 344.

The tethers 304, 342 act as actuators for their respective augmentation zones 338, 340, which can be actuated independently of each other with the illustrated embodiment of the implant 300. As illustrated in FIG. 56, pulling the first tether 304 reduces the size of the first loop 316, which causes the proximal tack 314 and the intermediate tack 336 to move relative to each other; for example, the proximal tack 314 can be pulled distally toward the intermediate tack 336. This action places the first augmentation zone 338 in the augmented configuration. At this time, at least one of the tacks 314, 336 will also move relative to the pushrod 150, such as by sliding along the pushrod 150. As illustrated in FIG. 57, pulling the second tether 342 reduces the size of the second loop 344, which causes the intermediate tack 336 and the distal tack 312 to move relative to each other; for example, the intermediate tack 336 can be pulled distally toward the distal tack 312. This action places the second augmentation zone 340 in the augmented configuration. At this time, the intermediate tack 336 will also move relative to the pushrod 150, such as by sliding along the pushrod 150.

While the drawings show the independent, sequential actuation of the first and second augmentation zones 338, 340, it will be understood from the drawings and the description that the zones can be actuated in any sequence, or that the zones may be actuated generally simultaneously with each other by pulling the tethers 304, 342 at the same time. Further, while two augmentation zones are illustrated in the drawings, any number of zones can be provided by including additional tacks and tethers on the body 302 following the tethering pattern shown in the figures.

Figure 58:
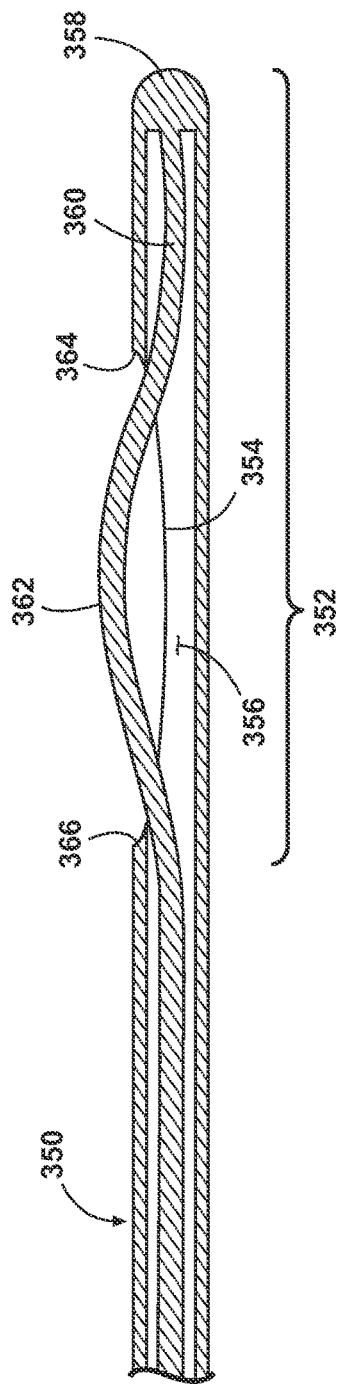
FIG. 58 is an enlarged sectional view of another embodiment of an introducer, particularly the proximal end of the introducer.
Figure 59:
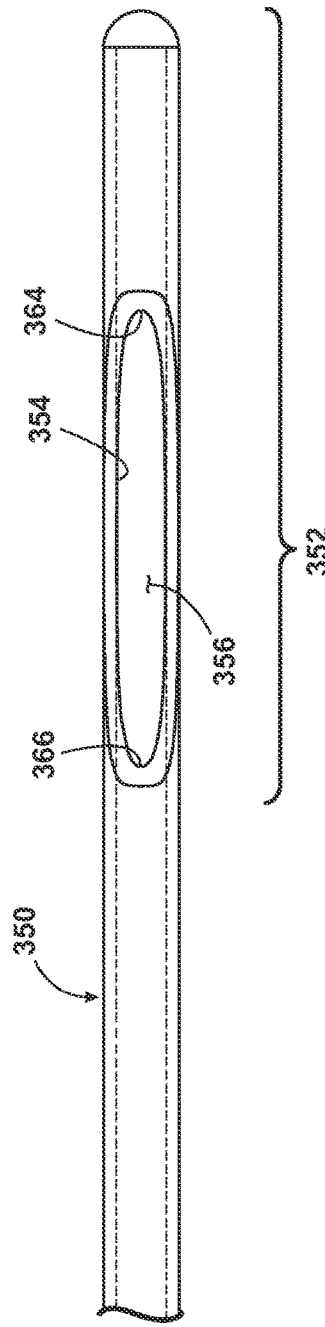
FIG. 59 is an enlarged top view of the introducer from FIG. 58.

FIGS. 58-61 illustrate another embodiment of an introducer or pushrod 350 for introducing an implant, such as implant 10 or implant 300, into a hollow anatomic structure. FIG. 58 is an enlarged sectional view of the proximal end of the pushrod 350. The pushrod 350 can be employed in place of pushrod 150 of FIG. 11 in the system 45 of FIG. 4, the system 190 of FIG. 26, or any other suitable system. The pushrod 350 can be similar in structure, function, and method of use to the pushrod 150, except as further described herein.

The pushrod 350 terminates at a distal tip region 352, which includes a single opening 354 that provides access to an internal lumen 356 that terminates at a distal plug 358. A wire 360 resides within the lumen 356 except for an implant retaining portion 362 located externally of the lumen 356 adjacent the opening 354. The wire 360 exits and enters the lumen 356 through the opening 354 to form the implant retaining portion 362.

The opening 354 is made by forming a cut in the side wall of the pushrod 350, and includes a distal end 364 and a proximal end 366. When viewed from the side, as shown in FIG. 58, the side profile of the opening 354 gradually rises toward the proximal and distal ends 364, 366 such that both ends 364, 366 are nearly flush with the side wall of the pushrod 350, and the pushrod 350 has its full sidewall thickness at either end 364, 366 of the opening 354. The opening 354 can further have an elliptical profile at both ends 364, 366; or, alternatively each end can have a "wedge" profile wherein the adjacent upper edge of the pushrod sidewall is straight but angled with respect to the longitudinal axis of the pushrod, giving the opening 354 a shallow or flat-bottomed "V" configuration when viewed from the side as in FIG. 58. Furthermore, the edges of the opening 354 can be deburred during manufacture of the pushrod 350 so that they are relatively smooth, with no rough or sharp corners. These features of the opening 354—flush ends, gently sloping (e.g. elliptical or double-wedge) profile, and deburred edges—reduce the possibility of snagging a portion of the implant on the pushrod 350 when withdrawing the pushrod 350 from the vein or other HAS.

The above-described profiles for the opening 354 provide a gently sloping and gradual transition from the deep central portion of the opening 354 to the shallow or flush distal or proximal end of the opening. This reduces the tendency of the pushrod to snag the implant after the wire 360 has been retracted to release the implant. As the pushrod is withdrawn, the sloping sidewall edge adjacent the opening 354 gently urges the implant material to the side of the pushrod, allowing the pushrod to pass in the proximal direction without snagging the implant at the distal end of the opening 354 and inadvertently pulling the implant in the proximal direction.

Figure 60:
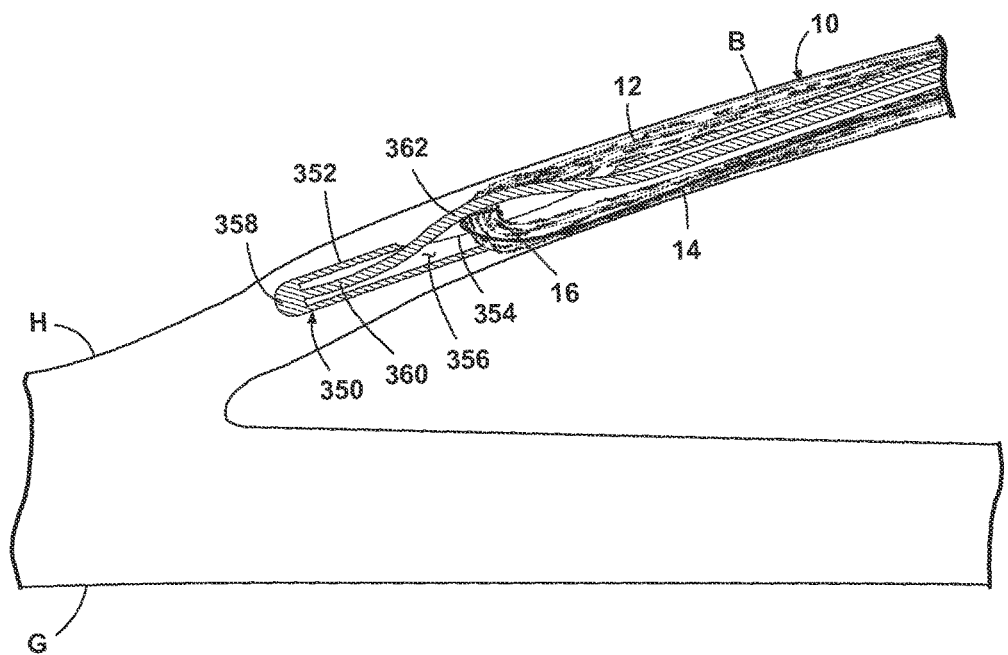
FIG. 60 is a sectional perspective view of the distal end of the introducer (in section) from FIG. 58 and the implant of FIG. 2 according to one embodiment.

With reference to FIG. 60, which illustrates the distal end of the pushrod 350 and the implant 10 within the greater saphenous vein B, the implant retaining portion 362 attaches the implant 10 to the pushrod 350 for cooperative movement during advancement of the pushrod 350. In the illustrated embodiment, the implant 10 attaches to the implant retaining portion 362 at the distal end 16 of the body 12 at or near where the tether 14 connects to the body 12. In particular, the distal end 16 is held between the implant retaining portion 362 of the wire 360 and the portion of the pushrod 350 defining the opening 354. In this configuration, the tether 14 and about half of the length of the body 12 are located on one side of the wire 360 and the other half of the length of the body 12 are located on the opposite side of the wire 360. The body 12 wraps around the wire 360 such that the free ends of the body 12 are folded upon each other form the proximal end 18 of the body 12, as described above. The implant retaining portion 362 thus forms a closed noose or snare around the implant 10 that permits the implant 10 to be retained whether the pushrod 350 is pushed distally or pulled proximally. This in turn facilitates use of the pushrod 350 either to push the implant 10 distally, or pull the implant 10 proximally, even when the implant is in a tightly confined space such as an HAS lumen or a sheath lumen. "Pull" functionality can be useful to longitudinally compress, radially expand, increase the density of, and increase the radial outward force applied by, the implant by slightly retracting the pushrod after insertion of the implant, as discussed above. The implant retaining portion 362 can further be configured to hold the implant 10 against the portion of the pushrod 350 adjacent the opening 354 tightly enough to prevent shifting of the implant 10. The above-described attachment of the implant 10 and the pushrod 350 provides an exemplary manner of attachment; the implant 10 and the pushrod 350 can be joined in any suitable manner and are not limited to that described above and shown in the figures.

One embodiment of a method of use of the pushrod 350 is described below. While the pushrod 350 can be employed in conjunction with any suitable HAS, the methods are described with respect to the greater saphenous vein B for illustrative purposes. It will be understood that the methods can be modified or adapted as necessary, if necessary, for use in other HASs. It will also be understood that while the pushrod 350 is described for use with the system 46, the methods can also be modified or adapted, as necessary, for use with embodiments of the system 46 other than the embodiment employed in the following description. Aspects of the method of use of the pushrod 350 that overlap with the method of use of the pushrod 150, described above, will be briefly summarized, but will not be described in detail. Generally, the method of use of the pushrod 350 can be similar to the use of pushrod 150, except as further described herein. In the description of the method, the various steps are discussed in terms of being performed by the practitioner; however, it is understood that these steps may be performed by the practitioner manually or through the operation of a motorized or non-motorized drive system, etc.

Figure 61:
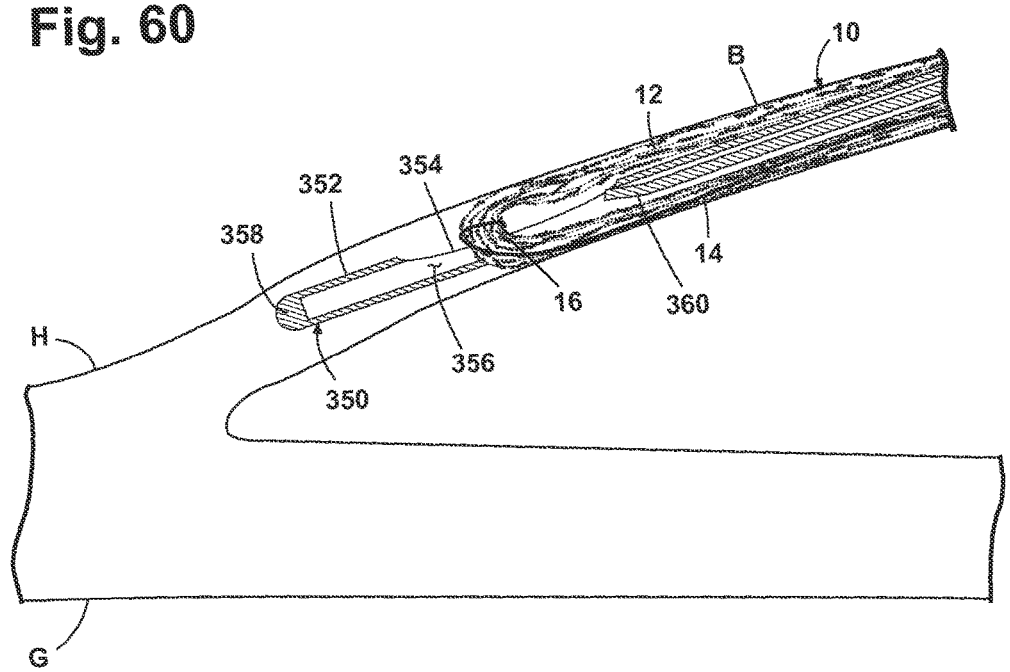
FIG. 61 is a view similar to FIG. 60 illustrating release of the implant from the introducer.

In one embodiment of a method of use of the pushrod 350, the various stages of the method can proceed as depicted for implant 10 as shown in FIGS. 15-20. FIG. 60 illustrates the pushrod 350 and implant 10 in the greater saphenous vein B after removal of the introducer sheath 20 from the vein B. The practitioner applies a proximal force to the wire 360, such as by pulling on the proximal end of the wire 360, thereby detaching the wire 360 from the distal plug 358. Continued application of the proximal force retracts the wire 360 through the opening 354 and releases the implant 10 from between the wire 360 and the pushrod 350, as illustrated in FIG. 61. The wire 360 can be retracted any desired distance corresponding to releasing the implant 10 from the pushrod 350. For example, the wire 360 need not be retracted past the proximal end 366 of the opening 354 if pulling the wire 360 only partly back from the distal end 364 of the opening 354 effects release of the implant 10. Retraction of the wire 360 removes the implant retaining portion 362 from the implant 10 and gives the pushrod 350 a lower profile for withdrawal since the wire 360 is contained within the circumferential profile of the pushrod 350. In other words, the pushrod 350 takes on a withdrawal profile upon retraction of the wire 360 into the pushrod lumen as seen in FIG. 61. The pushrod 350 (and the pushrods 150, 370, 390) advantageously achieves a withdrawal profile along its entire working length (the portion that enters, or is configured to enter, the sheath or HAS during use) which is no larger than the outer circumference (or other outer perimeter) of the pushrod sidewalls when viewed in cross-section (taken orthogonal to the longitudinal axis of the pushrod 350). This in turn reduces the chance of undesirably snagging and pulling the implant proximally when retracting the pushrod.

The practitioner follows release of the implant 10 with retraction of the pushrod 350 from the vein B and the remaining stages of the method proceed as shown in FIGS. 23-24A. Features of the pushrod 350, including the flush proximal and distal ends 364, 366 on the opening 354, the elliptical profile of the opening 354, the deburred edges of the opening 354, the removal of the implant retaining portion 362 when releasing the implant 10, and the lower profile during pushrod removal, reduce the possibility of snagging the implant 10 on the pushrod 350 as the pushrod 350 is retracted from the vein B.

Figure 62:
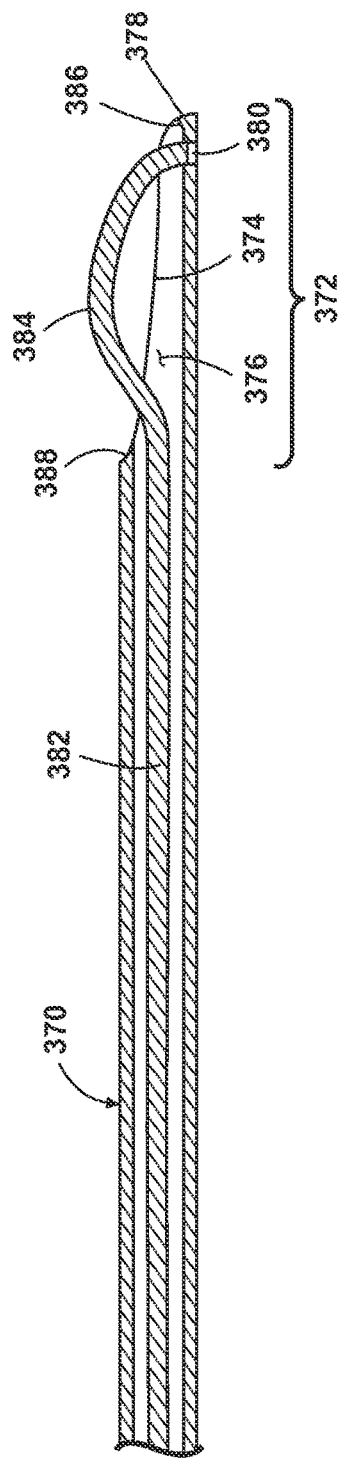
FIG. 62 is an enlarged sectional view of another embodiment of an introducer, particularly the proximal end of the introducer.

FIGS. 62-65 illustrate another embodiment of an introducer or pushrod 370 for introducing an implant, such as implant 10 or implant 300, into a hollow anatomic structure, and can be similar in structure, function and method of use to the pushrod 150 of FIG. 11 or the pushrod 350 of FIG. 58, except as further described herein. FIG. 62 is an enlarged sectional view of the proximal end of the pushrod 370. The pushrod 370 terminates at a distal tip region 372, which includes a single opening 374 that provides access to an internal lumen 376 that terminates at an open distal end 378. A through-hole 380 is formed in the sidewall of the pushrod 370 adjacent the open distal end 378. A wire 382 resides within the lumen 376 except for an implant retaining portion 384 located externally of the lumen 376 adjacent the opening 374. The wire 382 exits the lumen 376 through the opening 374 and is captured by the through-hole 380 to form the implant retaining portion 384. The implant retaining portion 384 is formed closer to the distal end of the pushrod 370 as compared with other embodiments of pushrods shown herein. This permits an implant to be held closer to the distal end of the pushrod 370, as discussed in further detail below.

The distal end of the wire 382 is removably retained by the through-hole 380 such that the wire 382 separates from the through-hole 380 upon application of a suitable proximal force to the wire 382. Continuation of the proximal force pulls the wire 382 through the opening such that the distal end of the wire 382 resides within the lumen 376 proximally of the opening 374. The proximal force can be applied by, for example, the practitioner pulling on the wire 382, in which case, a proximal end of the wire 382 can project from the pushrod 370, such as through the proximal end of the pushrod 370 (not shown). The type and degree of attachment between the wire 382 and the through-hole 380 can be selected according to a desired proximal force required to effect separation of the wire 382 from the through-hole 380. As an example, the wire 382 can be fit into to the through-hole 380 and retained by friction. Alternatively, the wire 382 can be attached to the through-hole 380 with an adhesive or by chemical joining processes, including various types of welding.

Figure 63:
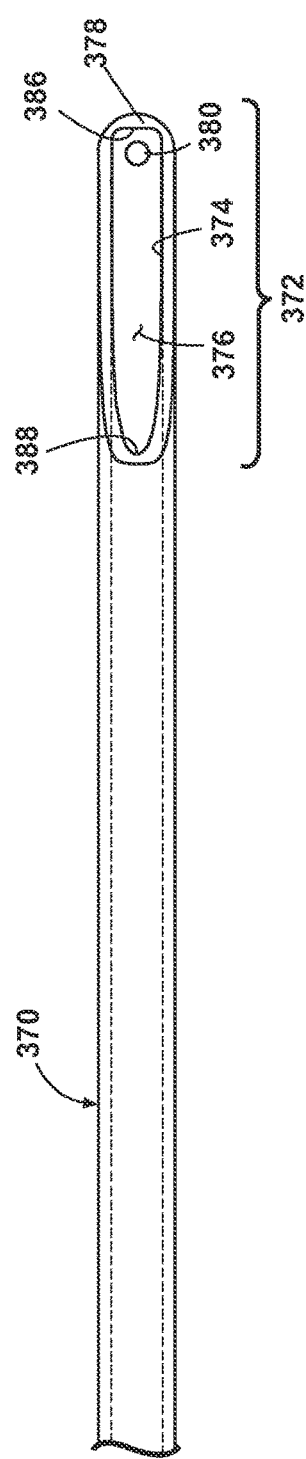
FIG. 63 is an enlarged top view of the introducer from FIG. 62.

The opening 374 is made by forming a cut in the side wall of the pushrod 370, and includes a distal end 386 and a proximal end 388. When viewed from the side, as shown in FIG. 62, the side profile of the opening 374 gradually rises from the distal end 386 toward the proximal end 388 such that the proximal end 388 is nearly flush with the side wall of the pushrod 370, and the pushrod 370 has its full sidewall thickness at the proximal end 388 of the opening 374. When viewed from the top, as shown in FIG. 63, which does not show the wire 382 for clarity purposes, the opening 374 further has an elliptical profile at the proximal end 388. Furthermore, the edges of the opening 374 can be deburred during manufacture of the pushrod 370 so that they are relatively smooth, with no rough or sharp corners. These features of the opening 375—flush proximal end 388, elliptical profile, and deburred edges—reduce the possibility of snagging an implant on the pushrod 370.

Figure 64:
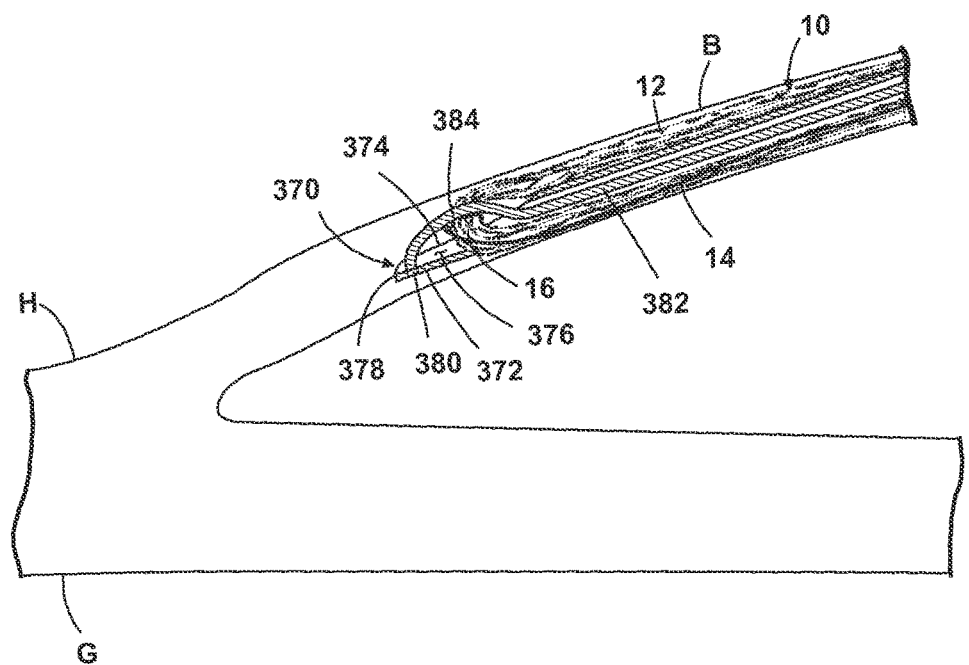
FIG. 64 is a sectional perspective view of the distal end of the introducer (in section) from FIG. 62 and the implant of FIG. 2 according to one embodiment.

With reference to FIG. 64, which illustrates the distal end of the pushrod 370 and the implant 10 within the greater saphenous vein B, the implant retaining portion 384 attaches the implant 10 to the pushrod 370 for cooperative movement during advancement of the pushrod 370. In the illustrated embodiment, the implant 10 attaches to the implant retaining portion 384 at the distal end 16 of the body 12 at or near where the tether 14 connects to the body 12. In particular, the distal end 16 is held between the implant retaining portion 384 of the wire 382 and the portion of the pushrod 370 defining the opening 374. In this configuration, the tether 14 and about half of the length of the body 12 are located on one side of the wire 382 and the other half of the length of the body 12 are located on the opposite side of the wire 382. The body 12 wraps around the wire 382 such that the free ends of the body 12 are folded upon each other form the proximal end 18 of the body 12, as described above. The implant retaining portion 384 forms a closed noose or snare around the implant 10 that permits the implant 10 to be retained whether the pushrod 370 is pushed distally or pulled proximally, thereby providing the push-pull functionality discussed above. The implant retaining portion 384 can further be configured to hold the implant 10 against the portion of the pushrod 370 adjacent the opening 374 tightly enough to prevent shifting of the implant 10. The above-described attachment of the implant 10 and the pushrod 370 provides an exemplary manner of attachment; the implant 10 and the pushrod 370 can be joined in any suitable manner and are not limited to that described above and shown in the figures.

The implant 10 attaches to the pushrod 370 closely to the distal end of the pushrod 370 due to the arrangement of the implant retaining portion 384 and the through-hole 380. This reduces the "dead space" associated with the pushrod 370, which is any portion of a pushrod that extends distally beyond an implant attached to the pushrod. For the present embodiment, the dead space can be approximately equivalent to the distance between the open distal end 378 and the implant retaining portion 384. Reduction of dead space is advantageous because it allows the practitioner to place an implant very close to the sapheno-femoral junction H without extending the pushrod 370 into the femoral vein G, which may carry a risk of abrading or puncturing the femoral vein G and injuring the patient, or of generating thrombosis within the femoral vein.

One embodiment of a method of use of the pushrod 370 is described below. While the pushrod 370 can be employed in conjunction with any suitable HAS, the methods are described with respect to the greater saphenous vein B for illustrative purposes. It will be understood that the methods can be modified or adapted as necessary, if necessary, for use in other HASs. It will also be understood that while the pushrod 370 is described for use with the system 46, the methods can also be modified or adapted, as necessary, for use with embodiments of the system 46 other than the embodiment employed in the following description. Aspects of the method of use of the pushrod 370 that overlap with the method of use of the pushrod 150, described above, will be briefly summarized, but will not be described in detail. In the description of the method, the various steps are discussed in terms of being performed by the practitioner; however, it is understood that these steps may be performed by the practitioner manually or through the operation of a motorized or non-motorized drive system, etc.

Figure 65:
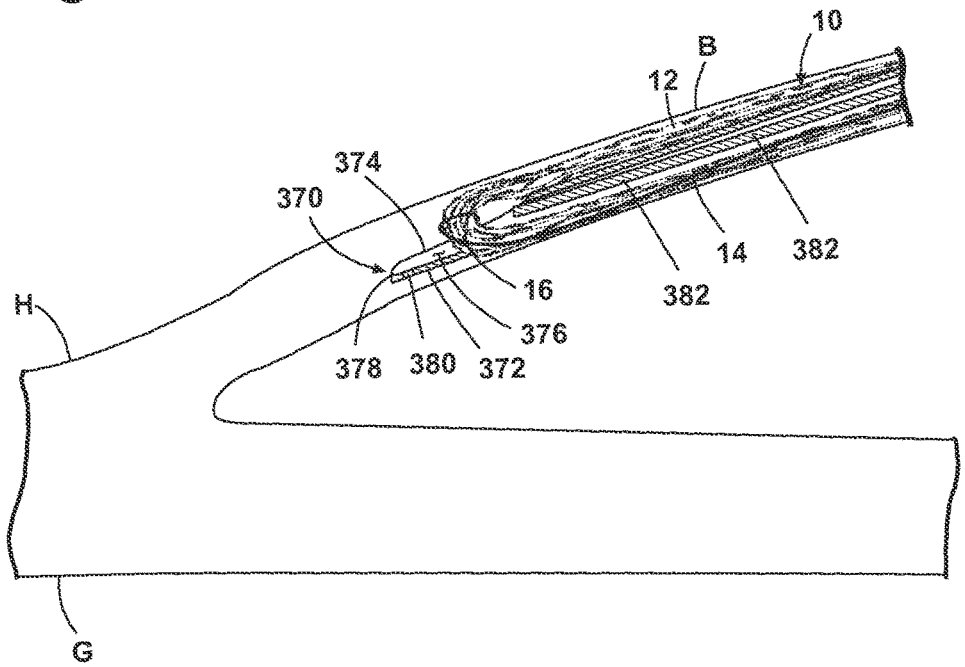
FIG. 65 is a view similar to FIG. 64 illustrating release of the implant from the introducer.

In one embodiment of a method of use of the pushrod 370, the various stages of the method can proceed as depicted for implant 10 as shown in FIGS. 15-20. FIG. 64 illustrates the pushrod 370 and implant 10 in the greater saphenous vein B after removal of the introducer sheath 20 from the vein B. The practitioner applies a proximal force to the wire 382, such as by pulling on the proximal end of the wire 382, thereby detaching the wire 382 from the through-hole 380. Continued application of the proximal force retracts the wire 382 through the opening 374 and releases the implant 10 from between the wire 382 and the pushrod 370, as illustrated in FIG. 65. The wire 382 can be retracted any desired distance corresponding to releasing the implant 10 from the pushrod 370. For example, the wire 382 need not be retracted past the proximal end 388 of the opening 374 if pulling the wire 384 only partly back from the distal end 386 of the opening 374 effects release of the implant 10. Retraction of the wire 382 removes the implant retaining portion 384 from the implant 10 and gives the pushrod 370 a lower profile since the wire 382 is contained within the circumferential profile of the pushrod 370. As discussed above with respect to the pushrods 350 and 150, a withdrawal profile is achieved with the pushrod 370 in which no portion of the pushrod protrudes radially beyond the outer circumference (or other outer perimeter) of the pushrod sidewall. This withdrawal profile advantageously prevails along the working length of the pushrod. The practitioner follows release of the implant 10 with retraction of the pushrod 370 from the vein B and the remaining stages of the method proceed as shown in FIGS. 23-24A. Features of the pushrod 370, including the flush proximal end 388 on the opening 374, the elliptical profile of the opening 374, the deburred edges of the opening 374, the removal of the implant retaining portion 384 when releasing the implant 10, and the low withdrawal profile during pushrod removal, reduce the possibility of snagging the implant 10 on the pushrod 370 as the pushrod 370 is retracted from the vein B. Furthermore, the dead space associated with the pushrod 370 is reduced by attaching the implant close to the distal end of the pushrod 370.

FIGS. 66-69 illustrate another embodiment of an introducer or pushrod 390 for introducing an implant, such as implant 10 or implant 300, into a hollow anatomic structure, and can be similar in structure, function and method of use to the pushrods 150, 350, 370, except as further described herein. FIG. 66 is an enlarged sectional view of the distal end of the pushrod 390. The pushrod 390 terminates at a distal tip region 392, which includes a single sidewall opening 394. A wire 400 resides within the lumen 396 and forms an implant retaining portion 402 adjacent the opening 394. The wire 400 is relatively straight, with little or no curvature in the implant retaining portion 402 or other portion of the wire 400. Employing the straight or only slightly curved wire 400 can afford greater flexibility in selecting a material for the wire 400. For example, stainless steel is a suitable material for the wire 400, whereas it may not be suitable for embodiments of the pushrod having a relatively highly curved wire (e.g. forming a highly curved implant retaining portion) since a curved stainless steel wire may plastically deform and may not straighten sufficiently to enable the wire to be retracted into the lumen 396 to release the implant. Stainless steel is also less expensive than other suitable wire materials, such as Nitinol. However, Nitinol is superelastic, and is suitable for embodiments of the pushrod having a relatively highly curved wire or retaining portion.

The opening 394 is made by forming a cut in the side wall of the pushrod 390, and includes a distal end 404 and a proximal end 406. When viewed from the side, as shown in FIG. 66, the proximal end 406 of the opening 394 is cut down deeper into the side wall of the pushrod 390 than the distal end 404. The side profile of the opening 394 gradually slopes or rises from the proximal end 406 to the distal end 404 such that the distal end 404 is flush or nearly flush with the side wall of the pushrod 390. In the depicted embodiment, the opening 394 has a curved or elliptical profile defined by the upper edge of the pushrod sidewall. Alternatively, the opening 394 can have a simpler "wedge" profile defined by a straight (but angled with respect to the longitudinal axis of the pushrod 390) upper edge of the pushrod sidewall. Furthermore, the edges of the opening 394 can be deburred during manufacture of the pushrod 390 so that they are relatively smooth, with no rough or sharp corners.

These features of the opening 394—flush distal end 404, sloping (e.g., curved/elliptical or wedge) profile of the opening 394, and deburred edges—reduce the possibility of snagging an implant on the pushrod 390. The above-described profiles for the opening 394 provide a gently sloping and gradual transition from the deep proximal portion of the opening 394 to the shallow or flush distal end of the opening. This reduces the tendency of the pushrod to snag the implant after the wire 400 has been retracted to release the implant. As the pushrod is withdrawn, the sloping sidewall edge adjacent the opening 394 (see, e.g., FIG. 69) gently urges the implant material to the side of the pushrod, allowing the pushrod to pass in the proximal direction without snagging the implant material at the distal end of the opening 394 and inadvertently pulling the implant in the proximal direction.

Figure 68:
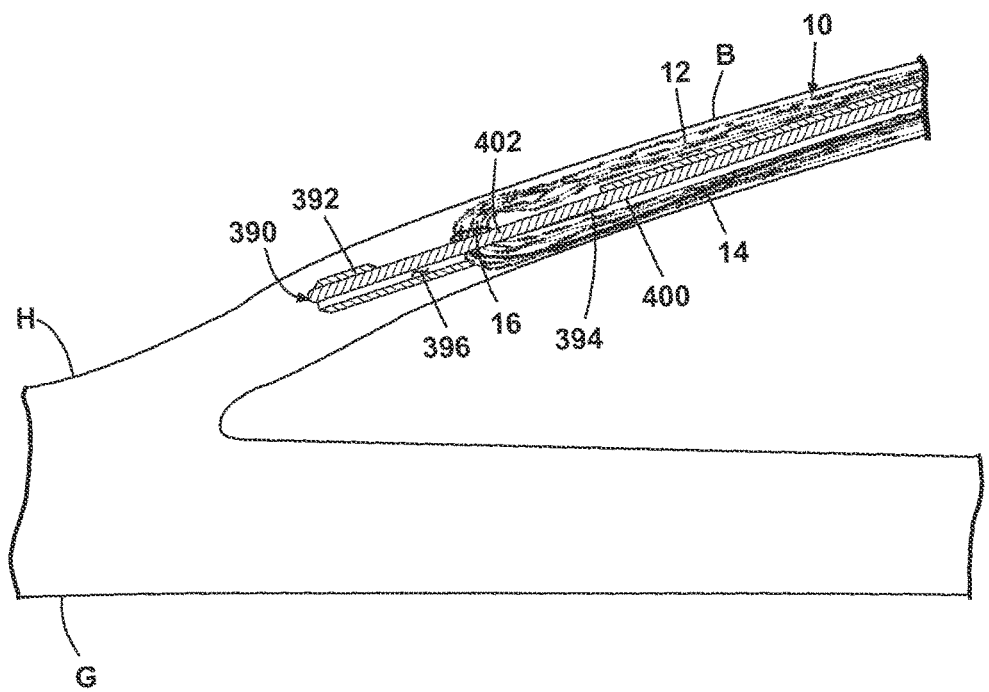
FIG. 68 is a sectional perspective view of the distal end of the introducer (in section) from FIG. 66 and the implant of FIG. 2 according to one embodiment.

With reference to FIG. 68, which illustrates the distal end of the pushrod 390 and the implant 10 within the greater saphenous vein B, the implant retaining portion 402 attaches the implant 10 to the pushrod 390 for cooperative movement during advancement of the pushrod 390. In the illustrated embodiment, the implant 10 attaches to or underlies the implant retaining portion 402 at the distal end 16 of the body 12 at or near where the tether 14 connects to the body 12. In particular, the distal end 16 is held between the implant retaining portion 402 of the wire 400 and the portion of the pushrod 390 defining the opening 394. In this configuration, the tether 14 and about half of the length of the body 12 are located on one side of the wire 400 and the other half of the length of the body 12 are located on the opposite side of the wire 400. The body 12 wraps around the wire 400 such that the free ends of the body 12 are folded upon each other and form the proximal end 18 of the body 12, as described above. The implant retaining portion 402 forms a closed noose or snare around the implant 10 that permits the implant 10 to be retained whether the pushrod 390 is pushed distally or pulled proximally. The implant retaining portion 402 can further be configured to hold the implant 10 against the portion of the pushrod 390 adjacent the opening 394 tightly enough to prevent shifting of the implant 10. The above-described attachment of the implant 10 and the pushrod 390 provides an exemplary manner of attachment; the implant 10 and the pushrod 390 can be joined in any suitable manner and are not limited to that described above and shown in the figures.

One embodiment of a method of use of the pushrod 390 is described below. While the pushrod 390 can be employed in conjunction with any suitable HAS, the methods are described with respect to the greater saphenous vein B for illustrative purposes. It will be understood that the methods can be modified or adapted as necessary, if necessary, for use in other HASs. It will also be understood that while the pushrod 390 is described for use with the system 46, the methods can also be modified or adapted, as necessary, for use with embodiments of the system 46 other than the embodiment employed in the following description. Aspects of the method of use of the pushrod 390 that overlap with the method of use of the pushrod 150, described above, will be briefly summarized, but will not be described in detail. Generally, the method of use of the pushrod 390 can be similar to the use of the pushrods 150, 350 or 370, except as further described herein. In the description of the method, the various steps are discussed in terms of being performed by the practitioner; however, it is understood that these steps may be performed by the practitioner manually or through the operation of a motorized or non-motorized drive system, etc.

In one embodiment of a method of use of the pushrod 390, the various stages of the method proceed as depicted for implant 10 as shown in FIGS. 15-20. FIG. 68 illustrates the pushrod 390 and implant 10 in the greater saphenous vein B after removal of the introducer sheath 20 from the vein B. The practitioner applies a proximal force to the wire 400, such as by pulling on the proximal end of the wire 400, thereby pulling the distal portion of the wire 400 into the pushrod lumen 396 proximal of the opening 394. In this embodiment, since the wire 400 is kept relatively straight and has little or no curvature at the implant retaining portion 402, a reduced proximal force can be applied to the wire 400 to pull it proximally along the lumen 396, since the force will be more closely aligned with the axis of the wire 400 as compared with previous pushrod embodiments having curved wires.

Figure 69:
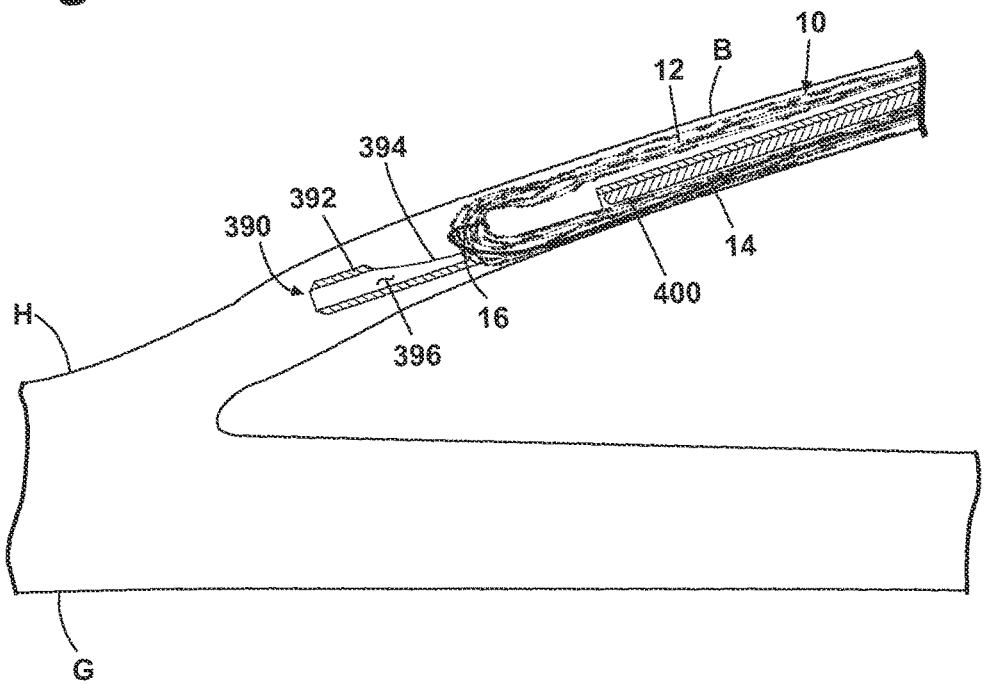
FIG. 69 is a view similar to FIG. 68 illustrating release of the implant from the introducer.

Continued application of the proximal force retracts the wire 400 through the opening 394 and releases the implant 10 from between the wire 400 and the pushrod 390, as illustrated in FIG. 69. The wire 400 can be retracted any desired distance corresponding to releasing the implant 10 from the pushrod 390. For example, the wire 400 need not be retracted past the proximal end 406 of the opening 394 if pulling the wire 400 only partly back from the distal end 404 of the opening 394 effects release of the implant 10. Retraction of the wire 400 removes the implant retaining portion 402 from the implant 10 and gives the pushrod 390 a low profile since the wire 400 is contained within the circumferential profile of the pushrod 390. The practitioner follows release of the implant 10 with retraction of the pushrod 390 from the vein B and the remaining stages of the method proceed as shown in FIGS. 23-24A. Features of the pushrod 390, including the flush distal end 404 of the opening 394, the sloping profile of the opening 394, the deburred edges of the opening 394, the removal of the implant retaining portion 402 when releasing the implant 10, and the lower profile during pushrod removal, reduce the possibility of snagging the implant 10 on the pushrod 390 as the pushrod 390 is retracted from the vein B. Furthermore, the pushrod 390 requires less force to operate by employing a relatively straight wire 400, and may cost less to manufacture since the wire 400 can be made from less expensive materials, such as stainless steel.

Despite the foregoing discussion of certain embodiments, only the following claims, and such other claims as may be presented in the future based on the disclosure herein (and not the present Detailed Description), are intended to define the invention(s) protected hereby.

What is claimed is:

1. An apparatus for introducing an implant into a hollow anatomical structure, the apparatus comprising:
    a storage unit having an exit opening and defining a chamber in communication with the exit opening;
    an elongate, self-expanding vascular implant having an expanded condition and stored within the chamber in the expanded condition, proximal of the exit opening;
    a removable cap configured to be on the storage unit, wherein the removable cap is configured to close an open proximal end of the storage unit to enclose the elongate, self-expanding vascular implant in the chamber; and
    a pushrod having a distal end aligned with and proximal of the exit opening;
    wherein the pushrod is pre-assembled to a distal end of the elongate, self-expanding vascular implant;
    further comprising an introducer sheath distal of the exit opening, wherein the introducer sheath comprises a shaft sized for insertion into the hollow anatomical structure;
    a guide proximal of the exit opening for facilitating compression of the elongate, self-expanding vascular implant as the pushrod is advanced toward and through the exit opening and into the introducer sheath; and
    a coupler assembly comprising mating proximal and distal couplers configured to couple the storage unit and a proximal end of the introducer sheath.

2. The apparatus of claim 1, wherein the pushrod and the elongate, self-expanding vascular implant have a common travel direction through the exit opening such that the elongate, self-expanding vascular implant is drawn toward and through the exit opening by the pushrod as the pushrod is advanced toward and through the exit opening.

3. The apparatus of claim 1, wherein the pushrod is stored within the chamber.

4. The apparatus of claim 1, wherein the chamber is generally shaped like a ring.

5. The apparatus of claim 1, wherein the pushrod is partially located exteriorly of the storage unit to expose a length of the pushrod for gripping, and wherein the pushrod re-enters the storage unit near a distal end of the storage unit.

6. The apparatus of claim 1, wherein the elongate, self-expanding vascular implant comprises an occluding implant.

7. The apparatus of claim 1, wherein the elongate, self-expanding vascular implant comprises a bioresorbable implant.

8. An apparatus for introducing an implant into a hollow anatomical structure (HAS), the apparatus comprising:
    a storage unit having an exit opening and defining a chamber in communication with the exit opening;
    an elongate vascular implant having an expanded condition that is larger than a size that would allow the elongate vascular implant to pass into and/or through the HAS;
    a removable cap configured to be on the storage unit, wherein the removable cap is configured to close an open proximal end of the storage unit to enclose the elongate, self-expanding vascular implant in the chamber; and
    a pushrod having a distal end aligned with and proximal of the exit opening;
    wherein the pushrod is pre-assembled to a distal end of the elongate vascular implant and the elongate vascular implant is stored within the chamber in the expanded condition proximal of the exit opening;
    further comprising an introducer sheath distal of the exit opening, wherein the introducer sheath comprises a shaft sized for insertion into the hollow anatomical structure;
    a guide proximal of the exit opening for facilitating compression of the elongate vascular implant as the pushrod is advanced toward and through the exit opening and into the introducer sheath; and
    a coupler assembly comprising mating proximal and distal couplers configured to couple the storage unit and a proximal end of the introducer sheath.

9. The apparatus of claim 8, wherein the pushrod and the elongate vascular implant have a common travel direction through the exit opening such that the elongate vascular implant is drawn toward and through the exit opening by the pushrod as the pushrod is advanced toward and through the exit opening.

10. The apparatus of claim 8, wherein the pushrod is stored within the chamber.

11. The apparatus of claim 8, wherein the chamber is generally shaped like a ring.

12. The apparatus of claim 8, wherein the pushrod is partially located exteriorly of the storage unit to expose a length of the pushrod for gripping, and wherein the pushrod re-enters the storage unit near a distal end of the storage unit.

13. The apparatus of claim 8, wherein the elongate vascular implant comprises an occluding implant.

14. The apparatus of claim 8, wherein the elongate vascular implant comprises a bioresorbable implant.

15. A method for introducing an implant into a hollow anatomical structure, the method comprising:

inserting an introducer sheath into the hollow anatomical structure, wherein the introducer sheath comprises a shaft sized for insertion into the hollow anatomical structure;

coupling a storage unit to a proximal end of the introducer sheath using a coupler assembly comprising mating proximal and distal couplers, the storage unit having an exit opening and defining a chamber in communication with the exit opening, the storage unit storing an elongate, self-expanding vascular implant in an expanded condition, proximally of the exit opening of the storage unit, wherein a pushrod has a distal end aligned with and proximal of the exit opening, and wherein the pushrod is pre-assembled to a distal end of the elongate, self-expanding vascular implant, and wherein a removable cap is configured to close an open proximal end of the storage unit to enclose the elongate, self-expanding vascular implant in the chamber; and advancing the pushrod through a guide proximal of the exit opening, wherein the guide facilitates compression of the elongate, self-expanding vascular implant as the pushrod is advanced toward and through the exit opening and into the introducer sheath.

16. The method of claim 15, wherein the implant comprises an occluding implant.

17. The method of claim 15, wherein advancing the pushrod through the guide causes compression of the implant to a size sufficient to fit in the introducer sheath.

18. The method of claim 15, wherein advancing the pushrod through the guide comprises gripping an exposed portion of the pushrod proximal of the pre-assembled pushrod and implant.

19. The method of claim 15, and further comprising expanding the implant after distally advancing the implant into the hollow anatomical structure by at least withdrawing the introducer sheath.

20. The method of claim 15, wherein the implant is radially larger than the exit opening in the expanded condition.

21. The method of claim 15, further comprising occluding a lumen of the blood vessel with the implant.

22. The method of claim 21, wherein the implant is bioresorbable.

23. The apparatus of claim 4, wherein the pushrod is stored in the chamber in a loop configuration generally corresponding to the ring shape of the chamber.

24. The apparatus of claim 2, wherein the storage unit defines a storage axis, and wherein the storage axis is angularly offset relative to the common travel direction.

25. The apparatus of claim 1, wherein the elongate, self-expanding vascular implant is anchored to a proximal end of the storage unit by the removable cap.

26. The apparatus of claim 11, wherein the pushrod is stored in the chamber in a loop configuration generally corresponding to the ring shape of the chamber.

27. The apparatus of claim 9, wherein the storage unit defines a storage axis, and wherein the storage axis is angularly offset relative to the common travel direction.

28. The apparatus of claim 8, wherein the elongate vascular implant is anchored to a proximal end of the storage unit by the removable cap.

* * * * *